US012595267B2

(12) United States Patent
Xu et al.

(10) Patent No.: US 12,595,267 B2
(45) Date of Patent: Apr. 7, 2026

(54) PREPARATION METHOD FOR AMIDE COMPOUND AND APPLICATION THEREOF IN FIELD OF MEDICINE

(71) Applicants: Shanghai Synergy Pharmaceutical Sciences Co., Ltd., Shanghai (CN); Zhejiang Huahai Pharmaceutical Co., Ltd., Zhejiang (CN)

(72) Inventors: Xin Xu, Shanghai (CN); Jia Chen, Shanghai (CN); Zhen Zhang, Shanghai (CN); Liming Zhang, Shanghai (CN); Qimei Wu, Shanghai (CN); Qingyun Jiang, Shanghai (CN); Fengying Guo, Shanghai (CN); Yuyun Zhang, Shanghai (CN); Hao Yu, Shanghai (CN); Ying Wang, Shanghai (CN); Kang Sun, Shanghai (CN); Chengxu Zang, Shanghai (CN); Chenggang Qin, Shanghai (CN); Xiaobo Zhou, Shanghai (CN); Xiaojuan Zhang, Shanghai (CN); Yijin Wang, Shanghai (CN); Xiaoer Xia, Shanghai (CN); Yunfei Li, Shanghai (CN); Jian Ge, Shanghai (CN)

(73) Assignees: SHANGHAI SYNERGY PHARMACEUTICAL SCIENCES CO., LTD., Shanghai (CN); ZHEJIANG HUAHAI PHARMACEUTICAL CO., LTD., Zhejiang (CN)

( * ) Notice: Subject to any disclaimer, the term of this patent is extended or adjusted under 35 U.S.C. 154(b) by 1178 days.

(21) Appl. No.: 17/442,899

(22) PCT Filed: Mar. 24, 2020

(86) PCT No.: PCT/CN2020/080870

§ 371 (c)(1),
(2) Date: Sep. 24, 2021

(87) PCT Pub. No.: WO2020/192650

PCT Pub. Date: Oct. 1, 2020

(65) Prior Publication Data

US 2022/0098178 A1 Mar. 31, 2022

(30) Foreign Application Priority Data

Mar. 25, 2019 (CN) ......................... 201910228244.8
Jul. 29, 2019 (CN) ......................... 201910687575.8

(51) Int. Cl.

| | |
|---|---|
| ***C07D 491/107*** | (2006.01) |
| ***A61P 35/00*** | (2006.01) |
| ***C07D 405/12*** | (2006.01) |
| ***C07D 405/14*** | (2006.01) |
| ***C07D 471/10*** | (2006.01) |
| ***C07D 487/04*** | (2006.01) |
| ***C07D 495/10*** | (2006.01) |

(52) U.S. Cl.

CPC .......... *C07D 491/107* (2013.01); *A61P 35/00* (2018.01); *C07D 405/12* (2013.01); *C07D 405/14* (2013.01); *C07D 471/10* (2013.01); *C07D 487/04* (2013.01); *C07D 495/10* (2013.01)

(58) Field of Classification Search

CPC .............. C07D 491/107; C07D 405/12; C07D 405/14; C07D 487/04; A61P 35/00
See application file for complete search history.

(56) References Cited

U.S. PATENT DOCUMENTS

2017/0217941 A1 8/2017 Campbell

FOREIGN PATENT DOCUMENTS

| | | | | |
|---|---|---|---|---|
| CN | 104080769 A | 10/2014 | | |
| CN | 105307683 A | 2/2016 | | |
| CN | 108314677 A | 7/2018 | | |
| JP | 2014513084 A | 5/2014 | | |
| JP | 2014516931 A | 7/2014 | | |
| JP | 2015531366 A | 11/2015 | | |
| JP | 2022528042 A | 6/2022 | | |
| JP | 2022528337 A | 6/2022 | | |
| WO | WO-2012142504 A1 | * 10/2012 | ......... | A61K 31/4412 |
| WO | 2013155464 A1 | 10/2013 | | |
| WO | 2013173441 A2 | 11/2013 | | |
| WO | 2014172044 A1 | 10/2014 | | |
| WO | 2015010049 A1 | 1/2015 | | |
| WO | 2015110999 A1 | 7/2015 | | |
| WO | 2017139404 A1 | 8/2017 | | |

(Continued)

OTHER PUBLICATIONS

Extended European Search Report for European Patent Application No. 20779835.6; Date of Mailing Mar. 31, 2022, 13 pages.
Christofides, A., et al., "Epigenetic regulation of cancer biology and anti-tumor immunity by EZH2," Oncotarget, 2016, vol. 7, No. 51, pp. 85264-85640.
Klein, J., "Can a person prevent multiple sclerosis?" Medical News Today, Apr. 29, 2020, pp. 1-9.

*Primary Examiner* — John S Kenyon
*Assistant Examiner* — Sara Elizabeth Bell
(74) *Attorney, Agent, or Firm* — CANTOR COLBURN LLP

(57) ABSTRACT

The present invention relates to a preparation method for an amide compound and an application thereof in the field of medicine. Specifically, provided by the present invention is an amide small molecule compound which is an inhibitor of Zeste gene enhancer homolog 2 (EZH2) and which may be used to prevent and/or treat EZH2-mediated related diseases, comprising tumors, myeloproliferative diseases or autoimmune diseases.

11 Claims, No Drawings

(56) References Cited

FOREIGN PATENT DOCUMENTS

| | | | | | |
|---|---|---|---|---|---|
| WO | 2018137639 | A1 | | 8/2018 | |
| WO | WO-2020192650 | A1 | * | 10/2020 | ......... A61K 31/4439 |
| WO | WO-2020192652 | A1 | * | 10/2020 | ......... A61K 31/4439 |

* cited by examiner

PREPARATION METHOD FOR AMIDE COMPOUND AND APPLICATION THEREOF IN FIELD OF MEDICINE

This application claims the priorities of both Chinese patent application filed before CNIPA on Mar. 25, 2019, application number 201910228244.8, entitled "PREPARATION METHOD FOR AMIDE COMPOUND AND APPLICATION THEREOF IN FIELD OF MEDICINE"; and Chinese patent application filed before CNIPA on Jul. 29, 2019, application number 201910687575.8, entitled "PREPARATION METHOD FOR AMIDE COMPOUND AND APPLICATION THEREOF IN FIELD OF MEDICINE". All of their disclosures are incorporated in this application by reference.

FIELD OF THE INVENTION

The invention belongs to the field of medicine, and relates to an amide small molecular compound, a preparation method thereof, a pharmaceutical composition containing the compound and use thereof in medicine. The present invention discloses that it is used as an inhibitor of Zeste gene enhancer homolog 2 (EZH2) for the prevention and/or treatment of diseases related to EZH2, such as malignant tumors.

BACKGROUND OF THE INVENTION

Malignant tumors are diseases that seriously threaten human health. In recent years, morbidity and mortality of malignant tumors have been on the rise, which have become a serious health problem facing the world. The occurrence and development of tumors is a multi-factor and multi-stage evolutionary process involving multiple gene mutations and epigenetic changes. Epigenetics refers to a genetic phenomenon in which the expression level and function of a gene are changed resulting in a heritable phenotype without any change in the DNA sequence of the gene. Polycomb group protein (PcG) is an important protein factor involved in the epigenetic negative regulation of chromatin genes. The PcG family includes two polymeric complexes, polycomb inhibitory complex 1 (PRC1) and polycomb inhibitory complex 2 (PRC2). Zeste gene enhancer homolog 2 (EZH2) is a core member of the polycomb group protein (PcG) family. EZH2 is a catalytic subunit that composes the PRC2 protein complex and plays a central role in the function of the PRC2 protein complex. EZH2 contains a highly conserved SET domain with histone methyl transferase (HMT) activity, which catalyzes the trimethylation of lysine 27 of histone H3 (H3K27me3), and then triggers the aggregation of PCR1 complex components at specific gene sites leading to the silencing of downstream target genes. These target genes are involved in the regulation of a variety of basic biological processes, such as apoptosis, cell cycle regulation, cell aging and differentiation. Current studies have shown that EZH2 is highly expressed in a variety of tumor tissues, and is closely related to the malignant progression, invasiveness and metastatic ability of tumors.

The high expression of EZH2 often relates to the progression and poor prognosis of human cancers [5], such as prostate cancer, breast cancer, bladder cancer, lung cancer, rectal cancer, lymphoma, etc. The mutation or deletion of EZH2 relates to tumors, such as diffuse large B cell lymphoma, follicular lymphoma, bone marrow proliferative abnormalities, and bone marrow proliferative diseases. At present, the Y641 and A677 mutations of EZH2 increase the activity of the encoded protein, leading to an increase in the level of H3K27me3, thereby promoting the proliferation of lymphoma cells.

In summary, EZH2 as an epigenetic enzyme is involved in the occurrence and development of tumors, and EZH2 inhibitors have good application prospects as drugs in the pharmaceutical industry.

The disclosed selective EZH2 inhibitors include those disclosed in WO2012005805, WO2012050532, WO2012118812, WO2015143424A2, WO2016102493A1, WO2017084494A1 and WO2018045971A1, etc. A series of patents for EZH2 inhibitors have been disclosed. However, there is still need to develop new EZH2 inhibitors to meet market demand.

A class of EZH2 inhibitors is redesigned and synthesized in the present invention. After experimental research, this class of compounds has high selectivity for EZH2 targets and exhibits excellent pharmacological effects in in vivo animal experiments.

SUMMARY OF THE INVENTION

The object of the present invention is to provide a compound represented by general formula (I), and a tautomer, mesomer, racemate, enantiomer, diastereomer or mixture thereof, pharmaceutically acceptable salt, polymorph, solvate or isotopic derivative thereof.

(I)

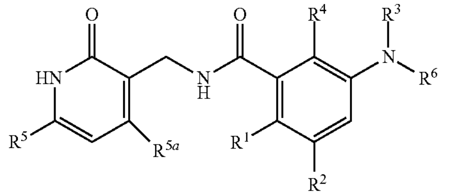

wherein, $R^1$ is hydrogen or halogen, and $R^1$ is more preferably hydrogen, —F or —Cl;

$R^2$ is selected from the group consisting of phenyl, 5-6 membered heteroaryl, and 8-11 membered bicyclic ring; in the bicyclic ring, the rings are connected by fusion or bridged by a carbon atom to form a spirocyclic compound. In the bicyclic ring, at least one ring is an aromatic ring, if one ring in the bicyclic ring is a heterocyclic ring containing a nitrogen atom, the nitrogen atom is not substituted or is substituted by $R^e$; a methylene on the bicyclic ring is not substituted, or is oxo to form a keto group, or is substituted by one $R^f$, or is substituted by both $R^f$ and $R^g$ at the same time. The phenyl or the 5-6 membered heteroaryl is substituted by $R^j$. The aromatic ring in the bicyclic ring is not substituted or is substituted by one $R^g$;

$R^2$ is further preferably selected from the group consisting of

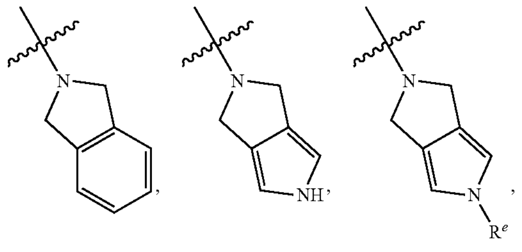

-continued

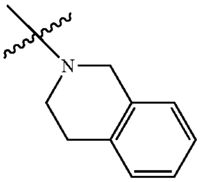,
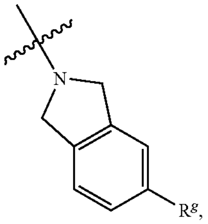

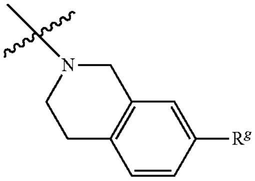,
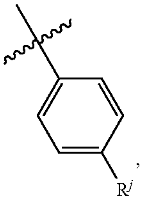,

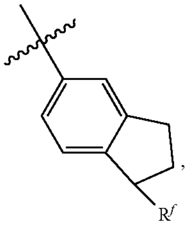, and
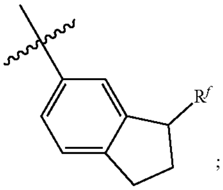;

$R^e$ is selected from the group consisting of —$C_{1-4}$ alkyl, —$C_{2-4}$ alkyl substituted by —$C_{1-3}$ alkyl, —$C_{2-4}$ alkyl substituted by hydroxyl, —$C_{1-4}$ alkylene-OH, -$T^0$, —$C_{1-4}$ alkylene-$T^0$, —$(CH_2)_n$—$CF_3$, —$(CH_2)_n$—$CF_2$—$CF_3$, —$(CH_2)_n$—$CHF_2$, —$(CH_2)_n$—$CH_2F$, —$(CH_2)_n$—O—$C_{1-3}$ alkyl, —C(O)—$C_{1-3}$ alkyl, —$(CH_2)_n$—C(O)—$C_{1-3}$ alkyl, —C(O)—$C_{2-4}$ alkenyl, —C(O)—$CF_3$, —C(O)—$(CH_2)_n$—$CF_3$, —C(O)—$(CH_2)_n$—$CF_2$—$CF_3$, —C(O)—$(CH_2)_n$—$CHF_2$, —C(O)—$(CH_2)_n$—$CH_2F$, —C(O)-$T^0$, —C(O)—$C_{1-3}$ alkylene-$T^0$, tert-butoxycarbonyl, —C(O)—O—$C_{1-3}$ alkyl, —C(O)—O—$(CH_2)_n$—$CF_3$, —C(O)—O—$(CH_2)_n$—$CHF_2$, —C(O)—O—$(CH_2)_n CH_2F$, —C(O)—O-$T^0$, —C(O)—O—$C_{1-3}$ alkylene-$T^0$, —$S(O)_2$—$C_{1-3}$ alkyl, —$S(O)_2$—$(CH_2)_n$—$CF_3$, —$S(O)_2$—$(CH_2)_n$—$CHF_2$, —$S(O)_2$—$(CH_2)_n$—$CH_2F$, —$S(O)_2$-$T^0$, and —$S(O)_2$—$C_{1-3}$ alkylene-$T^0$;

$R^e$ is further preferably selected from the group consisting of methyl, ethyl, propyl, —$CH(CH_3)$—$CH_3$, —$CH(CH_3)$—$(CH_2)$ $CH_3$, —$CH(CH_3)$—$CH(CH_3)_2$, —$CH_2$—$C(CH_3)_3$, $T^0$, —$(CH_2)_n$-$T^0$, —$(CH_2)_n$—$CF_3$, —$CH_2$—CH(OH)—$CH_3$, —$(CH_2)_n$—$CF_2$—$CF_3$, —$(CH_2)_2$—O—$C_{1-3}$ alkyl, —C(O)—$C_{1-3}$ alkyl, —$(CH_2)_n$—C(O)—$C_{1-3}$ alkyl, —C(O)—$C_{2-4}$ alkenyl, —C(O)—$CF_3$, —C(O)—$(CH_2)_n$—$CF_3$, —C(O)-morpholinyl, —C(O)$C_{3-6}$ cycloalkyl, tert-butoxycarbonyl, —C(O)—O—$C_{1-3}$ alkyl and —$S(O)_2$—$C_{1-3}$ alkyl;

$R^f$ and $R^g$ are each independently selected from the group consisting of halogen, —OH, —$C_{1-4}$ alkylene-OH, —$CF_3$, —$CHF_2$, —$CH_2F$, —$C_{1-4}$ alkyl, —$C_{2-4}$ alkyl substituted by —$C_{1-3}$ alkyl, —$(CH_2)_n$—$CF_3$, —$(CH_2)_n$—$CHF_2$, —$(CH_2)_n$—$CH_2F$, -$T^0$, —$C_{1-3}$ alkylene-$T^0$, —$NR^aR^b$, —$C_{1-3}$ alkylene-$NR^aR^b$, —O—$C_{1-4}$ alkyl, —O—$C_{2-4}$ alkenyl, —O—$C_{1-4}$ alkylene-OH, —O—$(CH_2)_n$—$CF_3$, —O—$(CH_2)_n$—$CHF_2$, O—$(CH_2)_n$—$CH_2F$, —O-$T^0$, —O—$C_{1-3}$ alkylene-$T^0$, —NH—C(O)—$C_{2-4}$ alkenyl, C(O)—$C_{1-3}$ alkyl, —$(CH_2)_n$—C(O)—$C_{1-3}$ alkyl, —C(O)—$C_{2-4}$ alkenyl, —C(O)—$(CH_2)_n$—$CF_3$, —C(O)—$(CH_2)_n$—$CHF_2$, —C(O)—$(CH_2)_n$—$CH_2F$, —C(O)-$T^0$, —C(O)—$C_{1-3}$ alkylene-$T^0$, tert-butoxycarbonyl, —C(O)—O—$C_{1-3}$ alkyl, —C(O)—O—$(CH_2)_n$—$CF_3$, —C(O)—O—$(CH_2)_n$—$CHF_2$, —C(O)—O—$(CH_2)_n$—$CH_2F$, —C(O)—O-$T^0$, —C(O)—O—$C_{1-3}$ alkylene-$T^0$, —$S(O)_2$—$C_{1-3}$ alkyl, —$S(O)_2$—$(CH_2)_n$—$CF_3$, —$S(O)_2$—$(CH_2)_n$—$CHF_2$, —$S(O)_2$—$(CH_2)_n$—$CH_2F$, —$S(O)_2$-$T^0$, and —$S(O)_2$—$C_{1-3}$ alkylene-$T^4$;

$R^f$ and $R^g$ are each further preferably selected from the group consisting of fluorine, —OH, —$CF_3$, methyl, ethyl, propyl, —$C_{2-3}$ alkyl substituted by —$C_{1-2}$ alkyl, —$(CH_2)_n$—$CF_3$, -$T^0$, —$C_{1-3}$ alkylene-$T^0$, —$NR^aR^b$, —$C_{1-3}$ alkylene-$NR^aR^b$, —O—$C_{1-4}$ alkyl, —O—$C_{2-4}$ alkenyl, —O-$T^0$, —NH—C(O)—$C_{2-4}$ alkenyl, —C(O)—$C_{1-3}$ alkyl —C(O)—$C_{2-4}$ alkenyl, —C(O)—$(CH_2)_n$—$CF_3$, —C(O)-$T^0$, tert-butoxycarbonyl, —C(O)—O—$C_{1-3}$ alkyl, and —C(O)—O-$T^0$;

$R^f$ is further preferably selected from the group consisting of methyl, ethyl, propyl, —F, —Cl, —OH, $T^0$, and —$C_{1-3}$ alkylene-$T^0$;

$R^g$ is further preferably selected from the group consisting of $T^0$, —$C_{1-3}$ alkylene-$T^0$, —NH—C(O)—$C_{2-3}$ alkenyl, —$NR^aR^b$ and —F;

when the methylene on the bicyclic ring is substituted by both $R^f$ and $R^g$ at the same time, $R^f$ and $R^g$ are each independently halogen, —OH or —$C_{1-3}$ alkyl;

$R^j$ is

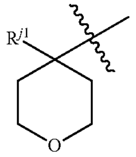 or 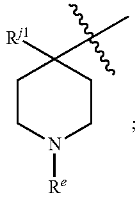;

$R^{j1}$ is —CN, —COOH, —C(O)O—$C_{1-3}$ alkyl, —$(CH_2)_n$—OH, or —$(CH_2)_n$—O—$C_{1-3}$ alkyl;

$R^a$ and $R^b$ are each independently selected from the group consisting of hydrogen, —$C_{1-3}$ alkyl, —$C_{1-4}$ alkylene-OH, -$T^0$, —$C_{1-3}$ alkylene-$T^0$, —$(CH_2)_n$—$CF_3$, —$(CH_2)_n$—$CHF_2$, —$(CH_2)_n$—$CH_2F$, —C(O)—$C_{1-3}$ alkyl, —C(O)—$C_{2-4}$ alkenyl, —C(O)—$(CH_2)_n$—$CF_3$, —C(O)—$(CH_2)_n$—$CHF_2$, —C(O)—$(CH_2)_n$—$CH_2F$, —C(O)-$T^0$, —C(O)—$C_{1-3}$ alkylene-$T^0$, —$C_{2-4}$ alkylene-$OCH_3$ and —$C_{2-6}$ alkylene-$CH_3$, wherein the $C_{2-6}$ alkylene is optionally interrupted by an oxygen atom and/or is optionally substituted by one or more $C_{1-3}$ alkyl;

or $R^a$ and $R^b$ together with the nitrogen atom to which they are attached form an unsubstituted or substituted 4-6 membered heterocycloalkyl, wherein the 4-6 membered heterocycloalkyl is a heterocycloalkane with one nitrogen as heteroatom, a heterocycloalkane with two nitrogens as heteroatoms, or a heterocycloalkane with one nitrogen and one oxygen as heteroatoms;

$R^a$ and $R^b$ are each further preferably selected from the group consisting of methyl, ethyl, propyl, —$C_{1-4}$ alkylene-OH, —$C_{2-4}$ alkylene-$OCH_3$ and

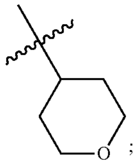 [SMILES: *C1CCOCC1] ;

$R^a$ and $R^b$ are each further preferably selected from the group consisting of methyl, ethyl, propyl, and

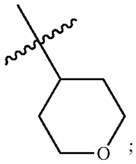 [SMILES: *C1CCOCC1] ;

$T^0$ is —$C_{3-8}$ cycloalkyl, 4-6 membered heterocycloalkyl, phenyl or 5-6 membered heteroaryl unsubstituted or substituted by $T^1$; when $T^0$ is a 4-6 membered heterocycloalkyl and a 5-6 membered heteroaryl, if the heteroatom is a nitrogen atom, the nitrogen atom is not substituted or substituted by $T^2$; $T^0$ is further preferably selected from the group consisting of

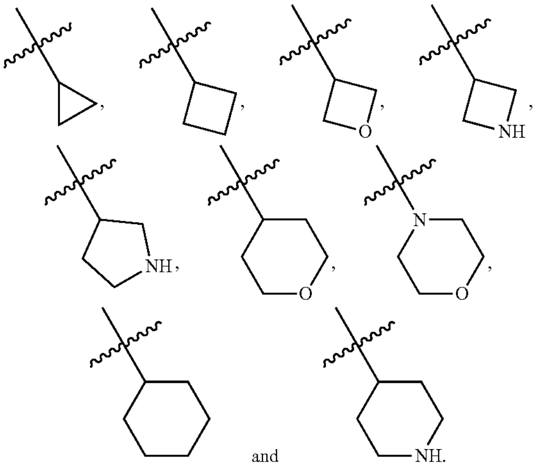

, , , , , , , and $T^1$ is selected from the group consisting of halogen, —$C_{1-6}$ alkyl, —$C_{1-3}$ alkoxyl, —$C_{1-6}$ alkyl substituted by —$C_{1-3}$ alkyl and —$NR^cR^d$; $T^1$ is further preferably selected from the group consisting of fluorine, methyl, ethyl, propyl, —$C_{1-3}$ alkoxyl, —$C_{2-3}$ alkyl substituted by —$C_{1-2}$ alkyl and —$NR^cR^d$;

$T^2$ is selected from the group consisting of —$C_{1-4}$ alkyl, —$C_{2-4}$ alkyl substituted by —$C_{1-3}$ alkyl, —$C_{1-4}$ alkylene-OH, —$C_{3-6}$ cycloalkyl, 4-6 membered heterocycloalkyl, —$(CH_2)_n$—$CF_3$, —$(CH_2)_n$—$CHF_2$, —$(CH_2)_n$—$CH_2F$, —C(O)—$C_{1-3}$ alkyl, —C(O)—$C_{2-4}$ alkenyl, —C(O)—$(CH_2)_n$—$CF_3$, —C(O)—$(CH_2)_n$—$CHF_2$, —C(O)—$(CH_2)_n$—$CH_2F$, tert-butoxycarbonyl, —$S(O)_2$—$C_{1-3}$ alkyl, —$S(O)_2$—$(CH_2)_n$—$CF_3$, and —$S(O)_2$—$(CH_2)_n$—$CHF_2$;

n is 1, 2, 3, or 4;

$R^3$ is hydrogen, —$C_{1-4}$ alkyl or substituted —$C_{1-4}$ alkyl, wherein the substituted —$C_{1-4}$ alkyl is optionally substituted by one or more of the following substituents: hydroxyl, carboxyl or —C(O)O—R'; $R^3$ is preferably hydrogen or —$C_{1-4}$ alkyl;

$R^3$ is further preferably hydrogen or —$C_{1-4}$ alkyl;

R' is selected from the group consisting of —$C_{1-6}$ alkyl, —$C_{2-6}$ alkenyl, —$C_{2-6}$ alkynyl, —$C_{3-8}$ cycloalkyl and —$C_{4-10}$ heterocycloalkyl;

$R^4$ and $R^5$ are each independently —$C_{1-6}$ alkyl;

$R^{5a}$ is —$C_{1-6}$ alkyl or —$C_{1-6}$ alkoxyl, and $R^{5a}$ is further preferably —$C_{1-2}$ alkyl or —$C_{1-2}$ alkoxyl;

$R^6$ is selected from the group consisting of —$C_{1-6}$ alkyl, 4-6 membered cycloalkyl, 4-6 membered heterocycloalkyl and a bicyclic ring having 8 to 10 carbon atoms; in the 5-6 membered heterocycloalkyl, the heteroatom is nitrogen, sulfur or oxygen; both rings in the bicyclic ring are connected by fusion, and any ring in the bicyclic ring is saturated, unsaturated or aromatic; the cycloalkyl, heterocycloalkyl or bicyclic ring with 8 to 10 carbon atoms is unsubstituted or substituted by one or more $R^{6a}$, wherein $R^{6a}$ is selected from the group consisting of halogen, hydroxyl, —$C_{1-3}$ alkyl, —$C_{1-3}$ alkoxyl, 3-6 membered cycloalkyl, 4-6 membered heterocyclic group, —$NR^hR^k$, —C(O)—$C_{1-3}$ alkyl, —C(O)—$C_{3-6}$ cycloalkyl, —$S(O)_2$—$C_{1-3}$ alkyl, —$(CH_2)_n$—$CF_3$, and —$S(O)_2$—$C_{3-6}$ cycloalkyl;

when $R^6$ is a sulfur heterocyclic group containing one sulfur atom, the sulfur heteroatom is not oxidized or is oxidized by two oxy groups to form a sulfone group;

when $R^6$ is a nitrogen heterocyclic group containing one nitrogen atom, the nitrogen atom is unsubstituted or is substituted by $R^{6b}$, and $R^{6b}$ is selected from the group consisting of —$C_{1-4}$ alkyl, —$C_{2-4}$ alkyl substituted by —$C_{1-3}$ alkyl, —$C_{1-4}$ alkylene-OH, —$C_{3-8}$ cycloalkyl, 4-6 membered heterocycloalkyl, —C(O)—$C_{1-3}$ alkyl, —C(O)—$C_{3-6}$ cycloalkyl, —$(CH_2)_n$—$CF_3$, —$S(O)_2$—$C_{1-3}$ alkyl, and —$S(O)_2$—$C_{3-6}$ alkyl;

$R^{6b}$ is further preferably selected from the group consisting of —$C_{1-3}$ alkyl, —$C_{2-3}$ alkyl substituted by —$C_{1-2}$ alkyl, —$C_{3-6}$ cycloalkyl, 4-6 membered heterocycloalkyl, —C(O)—$C_{1-3}$ alkyl, —C(O)—$C_{3-6}$ cycloalkyl, —$(CH_2)_n$—$CF_3$, —$S(O)_2$—$C_{1-3}$ alkyl, and —$S(O)_2$—$C_{3-6}$ cycloalkyl, wherein the heteroatom in the 4-6 membered heterocycloalkyl group is nitrogen or oxygen;

$R^6$ is further preferably selected from the group consisting of methyl, ethyl, propyl,

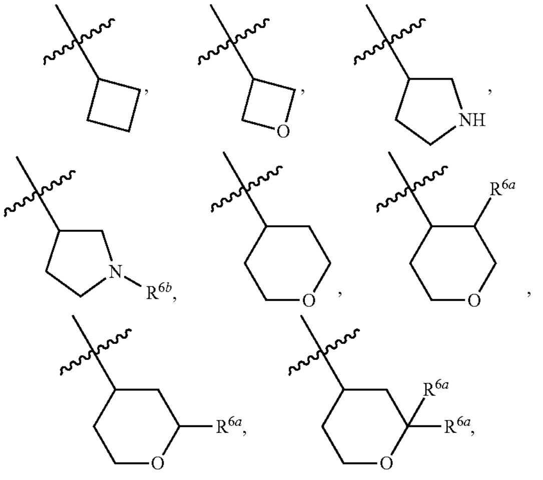

-continued

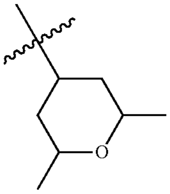, 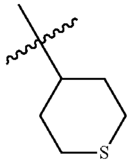, 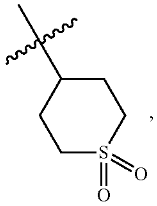,

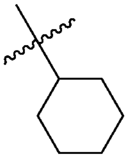, 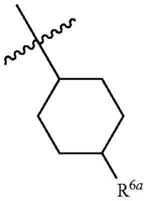, 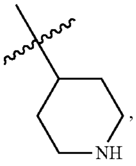,

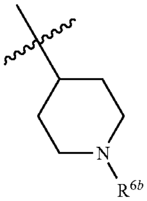, 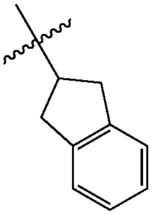, 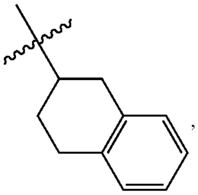,

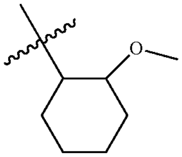 and 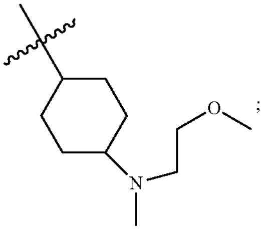;

$R^6$ is further selected from the group consisting of methyl, ethyl, propyl,

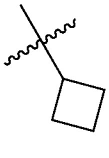, 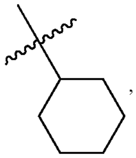, 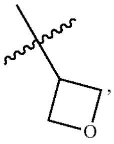,

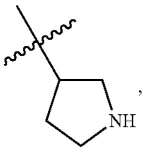, 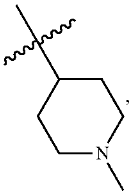,

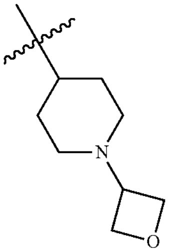, 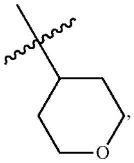, 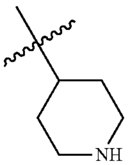,

-continued

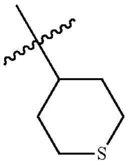, 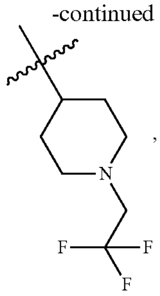, 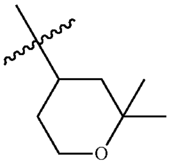,

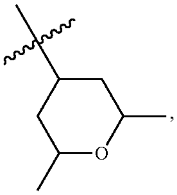, 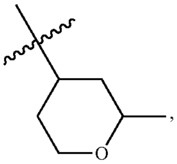, 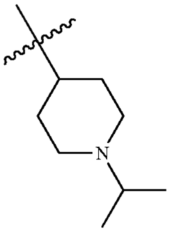,

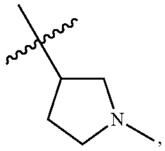, 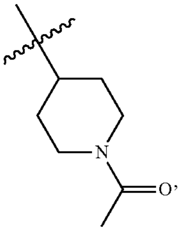, 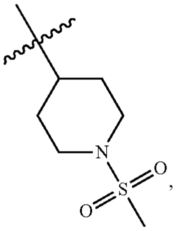,

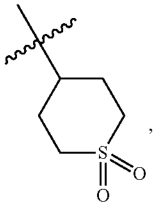, 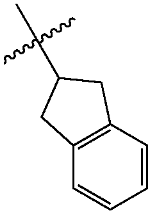, 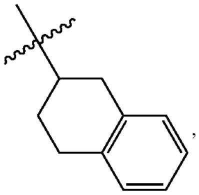,

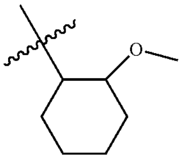 and 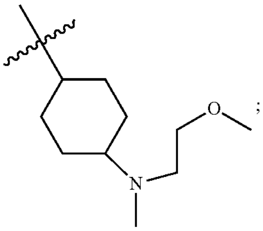;

$R^h$ and $R^k$ are each independently selected from the group consisting of hydrogen, $-C_{1-3}$ alkyl, $-C_{1-4}$ alkylene-OH, $-T^0$, $-C_{1-3}$ alkylene-$T^0$, $-(CH_2)_n-CF_3$, $-(CH_2)_n-CHF_2$, $-(CH_2)_n-CH_2F$, $-C(O)-C_{1-3}$ alkyl, $-C(O)-C_{2-4}$ alkenyl, $-C(O)-(CH_2)_n-CF_3$, $-C(O)-(CH_2)_n-CHF_2$, $-C(O)-(CH_2)_n-CH_2F$, $-C(O)-T^0$, $-C(O)-C_{1-3}$ alkylene-$T^0$, $-C_{2-4}$ alkylene-$OCH_3$ and $-C_{2-6}$ alkylene-$CH_3$, wherein the $C_{2-6}$ alkylene is optionally interrupted by an oxygen atom and/or is optionally substituted by one or more $C_{1-3}$ alkyl;

or $R^h$ and $R^k$ together with the nitrogen atom to which they are attached form a 4-6 membered heterocycloalkyl which is unsubstituted or is substituted by one or two T groups, wherein T is selected from the group consisting of halogen, $-C_{1-4}$ alkyl, $-C_{2-4}$ alkyl substituted by $-C_{1-3}$ alkyl and $-NR^cR^d$, wherein $R^c$ and $R^d$ are each independently selected from the group consisting of hydrogen, $-C_{1-3}$ alkyl, $-C_{1-4}$ alkylene-OH, $-C_{2-4}$ alkylene-$OCH_3$ and $-C_{2-6}$ alkylene-$CH_3$, wherein the $C_{2-6}$ alkylene is optionally interrupted by an oxygen atom and/or is optionally substituted by one or more $C_{1-3}$ alkyl;

$R^h$ and $R^k$ are further preferably selected from the group consisting of hydrogen, —$C_{1-3}$ alkyl, —$C_{2-3}$ alkylene-$OCH_3$ and —$C_{2-6}$ alkylene-$CH_3$, wherein the $C_{2-6}$ alkylene is optionally interrupted by an oxygen atom and/or is optionally substituted by one or more $C_{1-3}$ alkyl.

The Synthetic Process of the Compound Provided in the Present Invention:

The compounds represented by the general formulae of the present invention can be synthesized according to a variety of reaction schemes, and those skilled in the art can easily design reaction schemes for other compounds through some of the preparation methods provided in the examples herein.

The present invention relates to a method for preparing a compound represented by general formula (1) or a pharmaceutically acceptable salt thereof, scheme 1

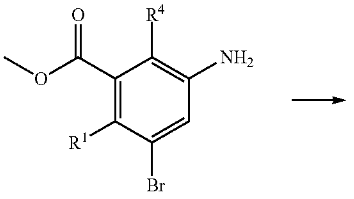

I-1

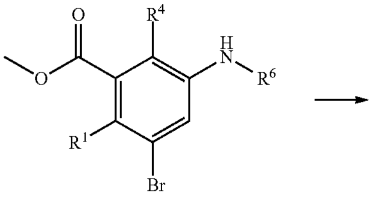

I-2

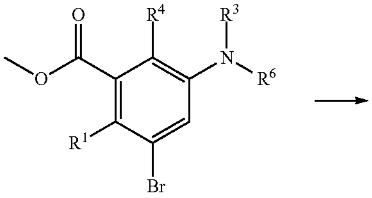

I-3

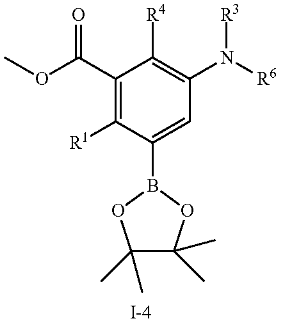

I-4

-continued

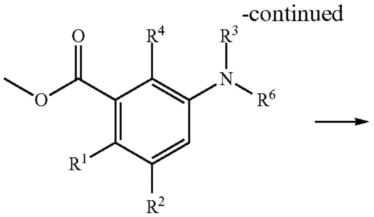

I-5

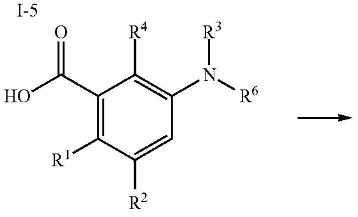

I-6

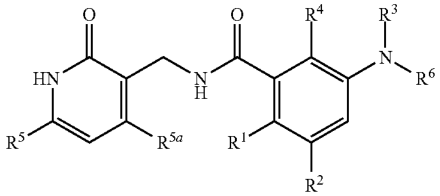

I-7 the compound of the general formula (I-2) is obtained through the reductive animation reaction between the compound of the general formula (I-1) and the ketone compound K1, wherein K1 includes —C(O)—$C_{1-6}$ alkyl, oxo substituted 4-6 membered cycloalkyl, oxo substituted 4-6 membered heterocycloalkyl or oxo substituted bicyclic ring with 8 to 10 carbon atoms; in the 4-6 membered heterocycloalkyl, the heteroatom is nitrogen, sulfur or oxygen; both rings in the bicyclic ring is connected by fusion, and any one ring in the bicyclic rings is saturated, unsaturated or aromatic; the oxo substituted cycloalkyl, oxo substituted heterocycloalkyl or oxo substituted bicyclic ring with 8 to 10 carbon atoms is unsubstituted or is substituted by one or more $R^{6a}$, wherein $R^{6a}$ is selected from the group consisting of halogen, hydroxyl, —$C_{1-3}$ alkyl, —$C_{1-3}$ alkoxyl, 3-6 membered cycloalkyl, 4-6 membered heterocyclic group, —$NR^hR^k$, —C(O)—$C_{1-3}$ alkyl, —C(O)—$C_{3-6}$ cycloalkyl, —$S(O)_2$—$C_{1-3}$ alkyl, —$(CH_2)_n$—$CF_3$, and —$S(O)_2$—$C_{3-6}$ cycloalkyl; K1 is further preferably selected from the group consisting of $C_{1-3}$ alkyl-C(O)—$C_{1-3}$alkyl,

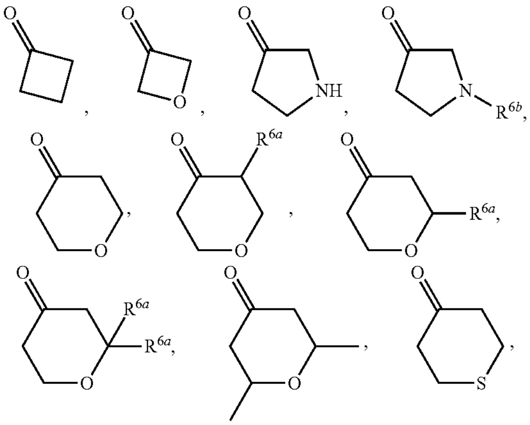

-continued

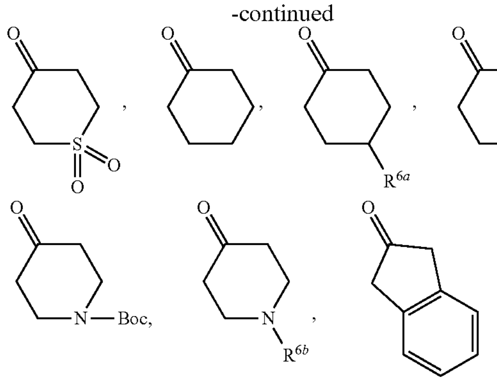

and

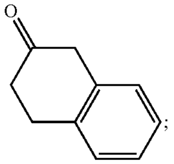

the compound of the general formula (I-3) is obtained by the reductive animation reaction of the compound of the general formula (I-2) with an aldehyde compound $R^7$—CHO under the presence of a reducing agent, wherein the reducing agent is optionally sodium triacetoxyborohydride in acetic acid, wherein $R^7$ is hydrogen, —$C_{1-4}$ alkyl or substituted —$C_{1-4}$ alkyl, wherein the substituted —$C_{1-4}$ alkyl is optionally substituted by one or more of the following substituents: hydroxyl, carboxyl or —C(O)O—$R^1$; $R^7$ is further preferably —H or —$C_{1-3}$ alkyl;

the compound of the general formula (I-4) is obtained by reacting the compound of the general formula (I-3) with a pinacol diborate compound under heating and alkaline conditions and the presence of a catalyst, wherein the reagent that provides alkaline condition is optionally potassium acetate, and the catalyst is optionally [1,1'-bis(diphenylphosphino)ferrocene]palladium dichloride;

the compound of the general formula (I-5) is obtained by reacting the compound of the general formula (I-4) with the corresponding halogenated aryl ($R^2$—Z) under heating and alkaline conditions and the presence of a catalyst, wherein the reagent that provides alkaline conditions is optionally selected from the group consisting of potassium carbonate, cesium carbonate, potassium hydroxide, sodium hydroxide, and cesium fluoride; the catalyst is optionally selected from the group consisting of [1,1'-bis(diphenylphosphino)ferrocene]palladium dichloride, palladium acetate, tetrakistriphenylphosphine palladium, and tris(dibenzylideneacetone)dipalladium, wherein Z is halogen;

the compound of general formula (I-5) is hydrolyzed under alkaline condition to obtain a compound of general formula (I-6), wherein the reagent that provides alkaline conditions is optionally sodium hydroxide;

the compound of the general formula (I-7) is obtained by the condensation reaction of the compound of the general formula (I-6) with the corresponding amine

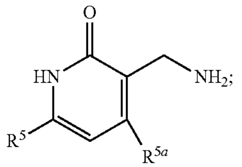

scheme 2

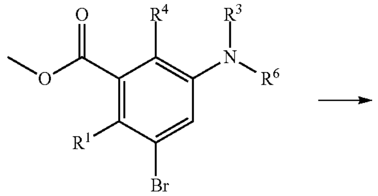

I-3

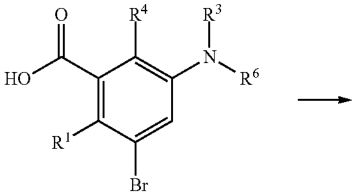

II-1

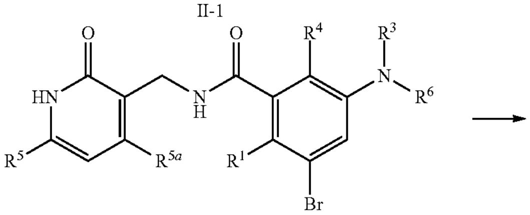

II-2

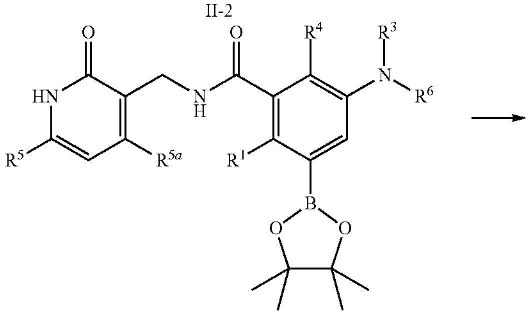

II-3

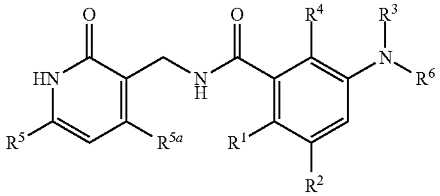

I the compound of general formula (II-1) is obtained by the hydrolysis reaction of compound of general formula (I-3) under heating and alkaline conditions, wherein the reagent that provides alkaline conditions is optionally selected from the group consisting of sodium hydroxide, potassium hydroxide, potassium carbonate, sodium carbonate, and cesium carbonate; the compound of general formula (II-2) is obtained by the condensation reaction of the compound of general formula (II-1) with the corresponding amine

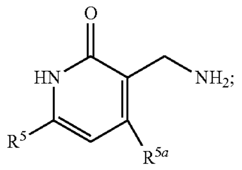

the compound of the general formula (II-3) is obtained by reacting the compound of the general formula (II-2) with a pinacol diborate compound under heating and alkaline conditions and the presence of a catalyst, wherein the reagent that provides alkaline conditions is optionally potassium acetate, and the catalyst is optionally [1,1'-bis(diphenylphosphino)ferrocene]palladium dichloride;

the compound of the general formula (I) is obtained by reacting the compound of the general formula (II-3) with the corresponding halogenated aryl ($R^2$—Z) under heating and alkaline conditions and the presence of a catalyst, wherein the reagent that provides alkaline conditions is optionally selected from the group consisting of potassium carbonate, cesium carbonate, potassium hydroxide, sodium hydroxide, and cesium fluoride; the catalyst is preferably selected from the group consisting of [1,1'-bis(diphenylphosphino)ferrocene]palladium dichloride, palladium acetate, tetrakistriphenylphosphine palladium, and tris(dibenzylideneacetone)dipalladium, wherein Z is halogen; or scheme 3

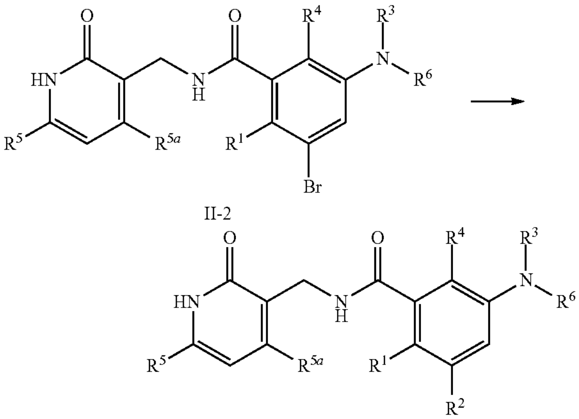

II-2

I the compound of the general formula (I) is obtained by reacting the compound of the general formula (II-2) with the corresponding aryl boronic ester

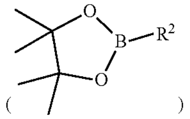

under heating and alkaline conditions and the presence of a catalyst, wherein the reagent that provides alkaline conditions is optionally selected from the group consisting of potassium carbonate, cesium carbonate, potassium hydroxide, sodium hydroxide, and cesium fluoride; the catalyst is optionally selected from the group consisting of [1,1'-bis(diphenylphosphino)ferrocene]palladium dichloride, palladium acetate, tetrakistriphenylphosphine palladium, and tris(dibenzylideneacetone)dipalladium; wherein the reagents that provide alkaline conditions include organic bases and inorganic bases; the organic bases include, but are not limited to, triethylamine, 4-dimethylaminopyridine, N,N-diisopropylethylamine, pyridine, potassium acetate, sodium tert-butoxide or potassium tert-butoxide; the inorganic bases include, but are not limited to, sodium hydride, potassium phosphate, sodium carbonate, potassium carbonate, cesium carbonate, calcium carbonate, and cesium fluoride. The catalysts involved include, but are not limited to, tris(dibenzylideneacetone) dipalladium, 4,5-bisdiphenylphosphine-9,9-dimethylxanthene, palladium acetate, tetra(triphenylphosphine)palladium, [1,1'-bis(diphenylphosphino) ferrocene]palladium dichloride, 2-dicyclohexylphosphorus-2,4,6-triisopropylbiphenyl, 1,10-phenanthroline, and cuprous iodide.

According to the compound represented by the general formula (I) and the pharmaceutically acceptable salt thereof in the present invention, the compound is specifically:

4'-(4-cyanotetrahydro-2H-pyran-4-yl)-N-((4,6-dimethyl-2-carbonyl-1,2-dihydro pyridin-3-yl)methyl)-5-(ethyl(tetrahydro-2H-pyran-4-yl)amino)-4-methyl-[1,1'-biphenyl]-3-formamide 4-(3'-(((4,6-dimethyl-2-carbonyl-1,2-dihydropyridin-3-yl) methyl)carbamoyl)-5'-(ethyl(tetrahydro-2H-pyran-4-yl) amino)-4'-methyl-[1,1'-biphenyl]-4-yl)tetrahydro-2H-pyran-4-carboxylic acid N-((4,6-dimethyl-2-carbonyl-1,2-dihydropyridin-3-yl) methyl)-5-(ethyl(tetrahydro-2H-pyran-4-yl)amino)-4'-(4-(hydroxymethyl)tetrahydro-2H-pyran-4-yl)-4-methyl-[1,1'-biphenyl]-3-carboxamide N-((4,6-dimethyl-2-carbonyl-1,2-dihydropyridin-3-yl) methyl)-3-(ethyl(tetrahydro-2H-pyran-4-yl)amino)-2-methyl-5-(1-morpholino-2,3-dihydro-1H-inden-5-yl) benzamide N-((4,6-dimethyl-2-carbonyl-1,2-dihydropyridin-3-yl) methyl)-5-(ethyl(tetrahydro-2H-pyran-4-yl)amino)-4'-(4-(methoxymethyl)tetrahydro-2H-pyran-4-yl)-4-methyl-[1,1'-biphenyl]-3-carboxamide 3-(ethyl(tetrahydro-2H-pyran-4-yl)amino)-N-((4-methoxy-6-methyl-2-oxo-1,2-dihydropyridin-3-yl)methyl)-2-methyl-5-(1-morpholino-2,3-dihydro-1H-inden-5-yl)benzamide N-((4,6-dimethyl-2-oxo-1,2-dihydropyridin-3-yl)methyl)-3-(ethyl(tetrahydro-2H-pyran-4-yl)amino)-2-methyl-5-(1-neopentyl 2',3',5',6'-tetrahydrospiro [indoline-3,4'-pyran]-6-yl)benzamide 2-chloro-4'-(4-cyanotetrahydro-2H-pyran-4-yl)-N-((4,6-dimethyl-2-oxo-1,2-dihydropyridin-3-yl)methyl)-5-(ethyl (tetrahydro-2H-pyran-4-yl)amino)-4-methyl-[1,1'-biphenyl]-3-formamide 2-chloro-N-((4,6-dimethyl-2-oxo-1,2-dihydropyridin-3-yl) methyl)-5-(ethyl (tetrahydro-2H-pyran-4-yl)amino)-6-methyl-3-(1-morpholino-2,3-dihydro-1H-inden-5-yl)benzamide N-((4,6-dimethyl-2-oxo-1,2-dihydropyridin-3-yl)methyl)-3-(ethyl(tetrahydro-2H-pyran-4-yl)amino)-6-fluoro-2-methyl-5-(1-morpholino-2,3-dihydro-1H-inden-5-yl) benzamide 2-chloro-5-(ethyl(tetrahydro-2H-pyran-4-yl)amino)-N-((4-methoxy-6-methyl-2-carbonyl-1,2-dihydropyridin-3-yl) methyl)-6-methyl-3-(1-morpholino-2,3-dihydro-1H-inden-5-yl)benzamide N-((4,6-dimethyl-2-oxo-1,2-dihydropyridin-3-yl)methyl)-3-((2,6-dimethyltetra hydro-2H-pyran-4-yl)(ethyl)amino)-2-methyl-5-(1-morpholino-2,3-dihydro-1H-inden-5-yl) benzamide N-((4,6-dimethyl-2-oxo-1,2-dihydropyridin-3-yl)methyl)-3-((2-methyltetrahydro-2H-pyran-4-yl)(ethyl)amino)-2-methyl-5-(1-morpholino-2,3-dihydro-1H-inden-5-yl)benzamide N-4,6-((dimethyl-2-oxo-1,2-dihydropyridin-3-yl)methyl)-3-(ethyl(tetrahydro-2H-pyran-4-yl)amino)-5-(5-isoindolin-2-yl)-2-methylbenzamide 5-(3,4-dihydroisoquinoline-2(1H)-yl)-N-((4,6-dimethyl-2-oxo-1,2-dihydropyridin-3-yl)methyl)-3-(ethyl(tetrahydro-2H-pyran-4-yl)amino)-2-methylbenzamide N-((4,6-dimethyl-2-oxo-1,2-dihydropyridin-3-yl)methyl)-3-(ethyl(tetrahydro-2H-pyran-4-yl)amino)-2-methyl-5-(5-morpholinoisoindolin-2-yl)benzamide 5-(5-acrylamidoisoindolin-2-yl)-N-((4,6-dimethyl-2-oxo-1,2-dihydropyridin-3-yl) methyl)-3-(ethyl(tetrahydro-2H-pyran-4-yl)amino)-2-methylbenzamide N-((4,6-dimethyl-2-oxo-1,2-dihydropyridin-3-yl)methyl)-3-(ethyl(tetrahydro-2H-pyran-4-yl)amino)-2-methyl-5-((5-morpholinomethyl)isoindolin-2-yl)benzamide N-((4,6-dimethyl-2-oxo-1,2-dihydropyridin-3-yl)methyl)-3-(ethyl(tetrahydro-2H-pyran-4-yl)amino)-2-methyl-5-(5-methyl-3,5-dihydropyrrolo[3,4-c]pyrrole-2(1H)-yl)benzamide N-((4,6-dimethyl-2-oxo-1,2-dihydropyridin-3-yl)methyl)-3-(ethyl(tetrahydro-2H-pyran-4-yl)amino)-5-(5-(ethyl(tetrahydro-2H-pyran-4-yl)amino)isoindolin-2-yl)-2-methylbenzamide N-((4,6-dimethyl-2-oxo-1,2-dihydropyridin-3-yl)methyl)-3-(ethyl(tetrahydro-2H-pyran-4-yl)amino)-5-(5-(ethyl(tetrahydro-2H-pyran-4-yl)amino)isoindolin-2-yl)-2-methylbenzamide N-(((4,6-dimethyl-2-oxo-1,2-dihydropyridin-3-yl)methyl)-3-(ethyl(tetrahydro-2H-pyran-4-yl)amino)-5-(6-fluoro-1-morpholino-2,3-dihydro-1H-inden-5-yl)-2-methyl benzamide 5-(6-chloro-1-morpholino-2,3-dihydro-1H-indan-5-yl)-N-(((4,6-dimethyl-2-oxo-1,2-dihydropyridin-3-yl)methyl)-3-(ethyl(tetrahydro-2H-pyran-4-yl)amino)-2-methylbenzamide N-(((4,6-dimethyl-2-oxo-1,2-dihydropyridin-3-yl)methyl)-3-(ethyl(tetrahydro-2H-pyran-4-yl)amino)-5-(7-fluoro-1-morpholino-2,3-dihydro-1H-inden-5-yl)-2-methyl benzamide 5-(3,3-dimethyl-1-morpholino-2,3-dihydro-1H-indan-5-yl)-N-(((4,6-dimethyl-2-oxo-1,2-dihydropyridin-3-yl) methyl)-3-(ethyl(tetrahydro-2H-pyran-4-yl)amino)-2-methylbenzamide N-(((4,6-dimethyl-2-oxo-1,2-dihydropyridin-3-yl)methyl)-3-(ethyl(tetrahydro-2H-pyran-4-yl)amino)-6-fluoro-5-(6-fluoro-1-morpholino-2,3-dihydro-1H-inden-5-yl)-2-methylbenzamide N-((4,6-dimethyl-2-oxo-1,2-dihydropyridin-3-yl)methyl)-3-(ethyl(tetrahydro-2H-pyran-4-yl)amino)-2-methyl-5-(1-(1-tetrahydro-2H-pyran-4-yl)indolin-5-yl) benzamide N-(((4,6-dimethyl-2-oxo-1,2-dihydropyridin-3-yl)methyl)-3-(ethyl(tetrahydro-2H-pyran-4-yl)amino)-2-methyl-5-(2-morpholino-2,3-dihydro-1H-inden-5-yl) benzamide.

In the present invention, the term "alkyl" includes saturated aliphatic groups, including linear alkyl groups (e.g., methyl, ethyl, propyl, butyl, pentyl, hexyl, heptyl, octyl, nonyl, decyl, etc.), branched alkyl groups (isopropyl, t-butyl, isobutyl, etc.), cycloalkyl groups (e.g. cyclopropyl, cyclobutyl, cyclopentyl, cyclohexyl, cycloheptyl, cyclooctyl, cyclopentenyl, cyclohexenyl, cycloheptenyl and adamantyl), alkyl substituted cycloalkyl, and cycloalkyl substituted alkyl.

In some embodiments, preferred cycloalkyl groups have 3-8 carbon atoms in their ring structure, and more preferably have 5 or 6 carbons in their ring structure.

The term "$C_{1-6}$ alkyl" includes alkyl groups containing 1 to 6 carbon atoms, such as methyl, ethyl, n-propyl, isopropyl, n-butyl, sec-butyl, t-butyl, n-pentyl, sec-pentyl, or n-hexyl. The term "$C_{1-3}$ alkyl" includes alkyl groups containing 1 to 3 carbon atoms, specifically methyl, ethyl, n-propyl and isopropyl.

In addition, the term "alkyl" also includes "unsubstituted alkyl" and "substituted alkyl", and the latter refers to an alkyl group in which hydrogen on one or more carbons in the hydrocarbon backbone is replaced by a substituent. The substituent include alkenyl, alkynyl, halogen, hydroxyl, alkylcarbonyloxyl, arylcarbonyloxyl, alkoxycarbonyloxyl, aryloxycarbonyloxyl, hydroxycarbonyl, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonate, cyano, amino (including alkylamino, dialkylamino, arylamino, diarylamino and alkylarylamino), acylamino (including alkylcarbonylamino, arylcarbonylamino, carbamoyl and ureido), amidino, imino, mercapto, alkylthio, arylthio, hydroxythiocarbonyl, sulfate, alkylsulfinyl, sulfonic acid, sulfamoyl, sulfonamido, nitro, trifluoromethyl, cyano, azido, heterocyclic, alkylaryl or aromatic group or heteroaromatic group.

As used herein, "heterocyclic" or "heterocyclic group" includes any ring structure (saturated, unsaturated or aromatic) that contains at least one ring heteroatom (e.g., a nitrogen atom, an oxygen atom, or a sulfur atom). Heterocyclic groups include heterocycloalkyl and heteroaryl, and examples of heterocyclic groups include, but are not limited to, furyl, pyridazinyl, imidazolidinyl, imidazolinyl, imidazolyl, isoquinolinyl, thiazolyl, isothiazolyl, isoxazolyl, methylenedioxyphenyl, morpholinyl, oxazolidinyl, oxazolyl, oxadiazolyl, 1,2,3-oxadiazolyl, 1,2,4-oxadiazolyl, 1,2,5-oxadiazolyl, 1,3,4-oxadiazolyl, 1,2,4-oxadiazole 5(4H)-one, piperazinyl, piperidinyl, piperidinone, 4-piperidinone, pyranyl, tetrahydropyran, pyrazinyl, pyrazolidinyl, pyrazolinyl, pyrazolyl, pyridazinyl, pyridyl, pyrimidinyl, pyrrolidinyl, pyrrolinyl, 2H-pyrrolyl, pyrrolyl, tetrahydrofuryl, tetrazolyl, thiazolyl, thienyl, tetrahydrothiophene, 1,2,3-triazolyl, 1,2,4-triazolyl, 1,2,5-triazolyl, 1,3,4-triazolyl, oxetane, and azetidine.

The term "aryl" or "aromatic ring" includes 5- and 6-membered monocyclic aromatic groups, which may contain 0-4 heteroatoms, such as benzene, phenyl, pyrrole, furan, thiophene, thiazole, isothiazole, imidazole, triazole, tetrazole, pyrazole, oxazole, isoxazole, pyridine, pyrazine, pyridazine and pyrimidine, etc. In addition, the term "aryl" also includes polycyclic aryl groups, such as tricyclic aryl groups, bicyclic aryl groups, such as naphthalene, benzoxazole, benzodiazole, benzothiazole, benzimidazole, benzothiophene, methylenedioxyphenyl, quinoline, isoquinoline, naphthyridine, indole, benzofuran, purine, benzofuran, deazapurine or indolizine.

Aryl groups with heteroatoms are also called "aromatic heterocyclic groups", "heterocyclic groups", "heteroaryls" or "heteroaromatic groups", wherein the heteroatoms are independently nitrogen, oxygen or sulfur, nitrogen atoms can be substituted or unsubstituted, nitrogen and sulfur heteroatoms can be optionally oxidized (i.e., N→O and $S(O)_p$, wherein p=1 or 2), and the total number of sulfur and oxygen atoms in the aromatic heterocycle is not more than 1.

Typical heteroaryl groups include 2- or 3-thienyl; 2- or 3-furyl; 2- or 3-pyrrolyl; 2-, 4- or 5-imidazolyl; 3-, 4- or 5-pyrazolyl; 2-, 4- or 5-thiazolyl; 3-, 4- or 5-isothiazolyl; 2-, 4- or 5-azolyl; 3-, 4- or 5-isozolyl; 3- or 5-1,2,4-triazolyl; 4- or 5-1,2,3-triazolyl; tetrazolyl; 2-, 3- or 4-pyridyl; 3- or 4-pyridazinyl; 3-, 4- or 5-pyrazinyl; 2-pyrazinyl; 2-, 4- or 5-pyrimidinyl.

The aromatic ring of "aryl" or "heteroaryl" may be substituted at one or more ring positions by the above-mentioned substituents, such as halogen, hydroxyl, alkoxyl, alkylcarbonyloxyl, arylcarbonyloxyl, alkoxycarbonyloxyl, aryloxycarbonyloxyl, hydroxycarbonyl, alkylcarbonyl, alkylaminocarbonyl, arylalkylaminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonate, cyano, amino (including alkylamino, dialkylamino, arylamino, diarylamino and alkylarylamino), acylamino (including alkylcarbonylamino, arylcarbonylamino, carbamoyl and ureido), amidino, imino, mercapto, alkylthio, arylthio, hydroxythiocarbonyl, sulfate, alkylsulfinyl, sulfonic acid, sulfamoyl, sulfonamido, nitro, trifluoromethyl, cyano, azido, heterocyclic, alkylaryl or aromatic group or heteroaromatic group, wherein the aryl group can also be fused or bridged with a non-aromatic alicyclic or heterocyclic ring to form a polycyclic ring (such as tetrahydronaphthalene).

As used herein, "bicyclic" or "tricyclic" refers to any stable bicyclic or tricyclic ring with a specified number of carbon atoms, any of which can be saturated, unsaturated or aromatic, the ring can be cycloalkyl, heteroalkyl, heteroaryl and aryl, and the rings can be connected to form bridged ring, fused ring and spiro ring.

The term "alkenyl" includes unsaturated aliphatic groups similar in length and possible substitution to the aforementioned alkyl groups, but contain at least one double bond.

For example, the term "alkenyl" includes straight chain alkenyl groups (e.g.: vinyl, propenyl, butenyl, pentenyl, hexenyl, heptenyl, octenyl, nonenyl, decenyl, etc.), branched alkenyl, cycloalkenyl (such as: cyclopropenyl, cyclopentenyl, cyclohexenyl, cycloheptenyl, cyclooctenyl), alkyl or alkenyl substituted cycloalkenyl and cycloalkyl or cycloalkenyl substituted alkenyl. The term "alkenyl" also includes alkenyl groups containing oxygen, nitrogen, sulfur, or phosphorus atoms that replace one or more carbons of the hydrocarbon backbone. In some embodiments, the straight or branched alkenyl group has 6 or fewer carbon atoms in its backbone (e.g.: $C_{2-6}$ straight alkenyl group, $C_{3-6}$ branched alkenyl group). The term $C_{2-6}$ alkenyl includes alkenyl groups containing 2-6 carbon atoms.

In addition, the term "alkenyl" also includes "unsubstituted alkenyl" and "substituted alkenyl", the latter refers to an alkenyl group in which hydrogen on one or more carbons in the hydrocarbon backbone is replaced by a substituent. The substituent include alkyl, alkynyl, halogen, hydroxyl, alkylcarbonyloxyl, arylcarbonyloxyl, alkoxycarbonyloxyl, aryloxycarbonyloxyl, hydroxycarbonyl, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonate, cyano, amino (including alkylamino, dialkylamino, arylamino, diarylamino and alkylarylamino), acylamino (including alkylcarbonylamino, arylcarbonylamino, carbamoyl and ureido), amidino, imino, mercapto, alkylthio, arylthio, hydroxythiocarbonyl, sulfate, alkylsulfinyl, sulfonic acid, sulfamoyl, sulfonamido, nitro, trifluoromethyl, cyano, azido, heterocyclic, alkylaryl or aromatic group.

The term "alkoxy" includes substituted and unsubstituted alkyl groups covalently linked to an oxygen atom. Examples of alkoxy include methoxyl, ethoxyl, isopropyloxyl, propoxyl, butoxyl, and pentoxy. Examples of substituted alkoxy groups include halogenated alkoxy groups. Alkoxy groups can be substituted by the following groups: alkenyl, alkynyl, halogen, hydroxyl, alkylcarbonyloxyl, arylcarbonyloxyl, alkoxycarbonyloxyl, aryloxycarbonyloxyl, hydroxycarbonyl, alkylcarbonyl, arylcarbonyl, alkoxycarbonyl, aminocarbonyl, alkylaminocarbonyl, dialkylaminocarbonyl, alkylthiocarbonyl, phosphate ester group, cyano, amino (including alkylamino, dialkylamino, arylamino, diarylamino and alkylarylamino), acylamino (including alkylcarbonylamino, arylcarbonylamino, carbamoyl and ureido), amidino, imino, mercapto, alkylthio, arylthio, hydroxythiocarbonyl, alkylsulfinyl, sulfonic acid group, sulfamoyl, sulfonamido, nitro, trifluoromethyl, cyano, azido, heterocyclic, alkylaryl or aromatic group.

The term "substituted" as used in the present invention means that any one or more hydrogen atoms on the specified atom is substituted by a substituent selected from the specified group, and the result of the substitution is to produce a stable compound. When the substituent is an oxo group or a keto group (i.e., =O), two hydrogen atoms on the atom are substituted, and the ketone substituent does not exist on the aromatic ring.

The pharmaceutically acceptable salt in the present invention refers to an inorganic base salt, such as sodium salt, potassium salt, calcium salt, magnesium salt, zinc salt, ammonium salt, quaternary ammonium salt or aluminum salt; an organic base salt, such as lysine salt, arginine salt, diethylamine salt, triethylamine salt, ethanolamine salt, trimethylamine salt, dicyclohexylamine salt, choline salt, dibenzylamine salt, piperidine salt and other pharmaceutically acceptable organic amine salts.

When the compound of the present invention contains at least one salt-forming nitrogen atom, it can be converted into the corresponding salt by reacting with the corresponding organic acid or inorganic acid in an organic solvent such as acetonitrile and tetrahydrofuran. Typical organic acids are oxalic acid, tartaric acid, maleic acid, succinic acid, methanesulfonic acid, benzoic acid, benzenesulfonic acid, toluenesulfonic acid, sulfamic acid, citric acid, glutamic acid, pyroglutamic acid, aspartic acid, glucuronic acid, naphthalenesulfonic acid, glutaric acid, acetic acid, trifluoroacetic acid, malic acid, fumaric acid, salicylic acid, 4-aminosalicylic acid, lactic acid, palmitic acid, stearic acid, lauric acid, cinnamic acid, alginic acid or ascorbic acid; typical inorganic acids are nitric acid, hydrochloric acid, sulfuric acid, or phosphoric acid.

When the compound of the present invention has one or more asymmetric carbon atoms, they can exist in the following forms: optically pure enantiomers, pure diastereomers, mixture of enantiomers, mixtures of diastereomers, racemic mixtures of enantiomers, racemates or mixtures of racemates. All possible isomers and stereoisomers of the compound of formula (II) and mixtures thereof are also within the scope of the present invention.

The present invention also provides a pharmaceutical composition comprising at least one of the above-mentioned compounds and optionally one or more pharmaceutically acceptable carriers and/or diluents.

The pharmaceutical composition provided by the present invention can be prepared in any form, such as granules, powders, tablets, coated tablets, capsules, pills, syrups, drops, solutions, suspensions and emulsions, or active ingredient sustained-release preparations, wherein examples of capsules include hard or soft gelatin capsules, and granules and powders may be in non-effervescent or effervescent forms.

The pharmaceutical composition of the present invention may further include one or more pharmaceutically or physiologically acceptable carriers, and these carriers will be appropriately formulated to facilitate application. For example, the pharmaceutically or physiologically acceptable carrier can be saline, hot-pressed water, Ringer's solution, buffered saline, dextrose, maltodextrin, glycerol, ethanol and mixtures thereof. The pharmaceutical composition of the present invention may also include pharmaceutically or physiologically acceptable additives, such as diluents, lubricants, binders, glidants, disintegrants, sweeteners, flavoring agents, wetting agents, dispersing agents, surfactants, solvents, coating agents, foaming agents, or fragrances.

Examples of diluents that can be used include, but are not limited to, lactose, sucrose, starch, kaolin, salt, mannitol, and dicalcium phosphate; examples of lubricants include, but are not limited to, talc, starch, magnesium or calcium stearates, lycopodium and stearic acid; examples of binders include, but are not limited to, microcrystalline cellulose, tragacanth, glucose solution, arabic gum syrup, gelatin solution, sucrose and starch paste; examples of glidants include, but are not limited to, colloidal silica; examples of disintegrants include, but are not limited to, croscarmellose sodium, sodium starch glycolate, alginic acid, corn starch, potato starch, bentonite, methyl cellulose, agar, and carboxymethyl cellulose; examples of sweeteners include, but are not limited to, sucrose, lactose, mannitol, and artificial sweeteners, such as sodium cyclamate and saccharin, and any number of spray-dried flavors; examples of flavoring agents include, but are not limited to, natural flavoring agents extracted from plants, such as fruits, and better-tasting compounds, such as, but not limited to, peppermint and methyl salicylate; examples of humectants include, but are not limited to, propylene glycol monostearate, sorbitan monooleate, diethylene glycol monolaurate, and polyoxyethylene lauryl ether.

The pharmaceutical composition of the present invention can be applied via various routes according to traditional methods, including oral, intravenous, intraarterial, intraperitoneal, intrathoracic, transdermal, nasal, inhalation, rectal, ocular and subcutaneous introduction.

The pharmaceutically acceptable carriers optionally added to the pharmaceutical composition of the present invention are: one or more of water, alcohol, honey, mannitol, sorbitol, dextrin, lactose, caramel, gelatin, calcium sulfate, magnesium stearate, talcum powder, kaolin, glycerin, tween, agar, calcium carbonate, calcium bicarbonate, surfactants, cyclodextrin and its derivatives, phospholipids, phosphates, starches and derivatives thereof, silicon derivatives, celluloses and derivatives thereof, pyrrolidones, polyethylene glycols, acrylic resins, phthalic acid esters, acrylic copolymers, and trimellitic acid esters.

It has been verified by pharmacological experiments that the compound or pharmaceutical composition provided by the present invention can treat tumors, myeloproliferative diseases or autoimmune diseases through EZH2, wherein said tumor is lymphoma, melanoma, glioma, gastrointestinal stromal tumor, prostate cancer, breast cancer, ovarian cancer, bladder cancer, lung cancer, rectal cancer, skin cancer, epithelial cell carcinoma, nasopharyngeal carcinoma, bone cancer, esophageal cancer or leukemia, and the autoimmune disease is inflammatory enteritis, autoimmune encephalomyelitis or multiple sclerosis.

The general dosage range of the compound provided by the present invention is about 0.001 mg/kg to 1000 mg/kg, preferably about 0.01 mg/kg to 100 mg/kg, more preferably about 0.1 to 20 mg/kg per day, wherein the dosage range of the pharmaceutical composition is calculated based on the amount of the above-mentioned compound contained in it.

DETAILED DESCRIPTION OF THE INVENTION

Example 1 4'-(4-cyanotetrahydro-2H-pyran-4-yl)-N-((4,6-dimethyl-2-carbonyl-1,2-dihydropyridin-3-yl)methyl)-5-(ethyl(tetrahydro-2H-pyran-4-yl)amino)-4-methyl-[1,1'-biphenyl]-3-formamide

1

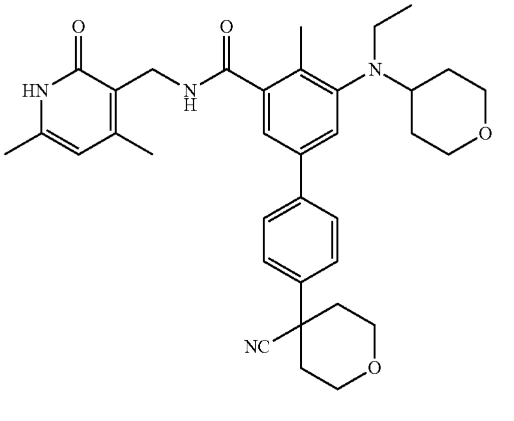

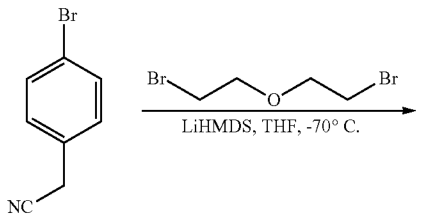

1a

-continued

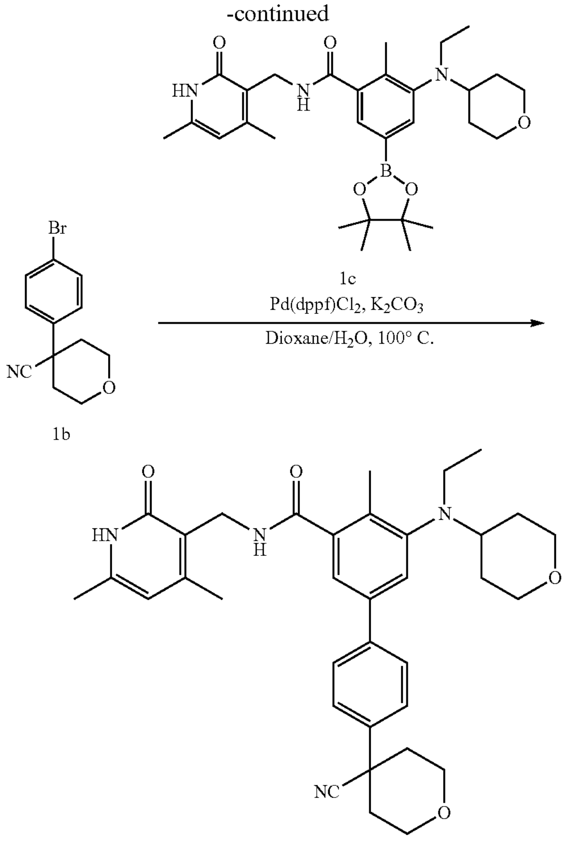

1c

1b

1

Step 1 4-(4-bromophenyl)tetrahydro-2H-pyran-4-carbonitrile 1b

Compound 1a (1.0 g, 5.1 mmol) and 1-bromo-2-(2-bromoethoxy)ethane (278 mg, 6.1 mmol) were dissolved in dry THF (20 mL) under the protection of nitrogen, which was cooled to −78° C. in a dry ice acetone bath, and LiHMDS (10.2 ml, 20.4 mmol) was slowly added dropwise. After the addition was completed, the dry ice acetone bath was removed, and the reaction solution was slowly warmed to room temperature and then heated to 70° C. and stirred for 2 hours. The reaction was quenched with saturated aqueous ammonium chloride solution, extracted with EA (10 ml×3). The organic phases were combined, dried over anhydrous sodium sulfate, concentrated and sampled, and purified by column chromatography (petroleum ether:ethyl acetate=0%-30%) to obtain the title compound 1b (700 mg, 2.63 mmol) as a white solid with a yield of 51.6%.

MS m/z (ESI): 268.1 [M+H]$^+$.

Step 2 4'-(4-cyanotetrahydro-2H-pyran-4-yl)-N-((4,6-dimethyl-2-carbonyl-1,2-dihydropyridin-3-yl)methyl)-5-(ethyl(tetrahydro-2H-pyran-4-yl)amino)-4-methyl-[1,1'-biphenyl]-3-formamide 1

Compound 1b (100 mg, 0.377 mmol) was dissolved in 3 ml of 1,4-dioxane, and compound 1c (197 mg, 0.377 mmol), Pd(dppf)Cl$_2$ (28 mg, 0.0377 mmol), potassium carbonate (104 mg, 0.754 mmol) and 1 ml of water were added in sequence, which were heated to 100° C. for 3 hours under nitrogen protection. After cooling to room temperature, 3 ml of water was added to dilute, which was extracted with EA (5 ml×3). The organic phases were combined, washed with saturated brine, dried and sampled, purified by column chromatography (methanol/dichloromethane=0%-10%) to obtain the title compound 1 (60 mg, 0.103 mmol), white solid, yield 27.3%.

$^1$H NMR (400 MHz, Methanol-d4) δ 7.68-7.62 (m, 2H), 7.62-7.55 (m, 2H), 7.46 (d, J=1.9 Hz, 1H), 7.32 (d, J=1.8 Hz, 1H), 6.09 (s, 1H), 4.47 (s, 2H), 4.10-4.02 (m, 2H), 3.94-3.79 (m, 4H), 3.34 (td, J=11.6, 2.1 Hz, 2H), 3.18-3.04 (m, 3H), 2.37 (s, 3H), 2.31 (s, 3H), 2.22 (d, J=0.8 Hz, 3H), 2.16 (ddd, J=13.6, 11.7, 4.4 Hz, 2H), 2.07 (dd, J=13.8, 2.1 Hz, 2H), 1.77-1.57 (m, 4H), 0.8 (t, J=7.0 Hz, 3H).

MS m/z (ESI): 583.7 [M+H]$^+$.

Example 2 4-(3'-(((4,6-dimethyl-2-carbonyl-1,2-dihydropyridin-3-yl)methyl) carbamoyl)-5'-(ethyl (tetrahydro-2H-pyran-4-yl)amino)-4'-methyl-[1,1'-biphenyl]-4-yl)tetrahydro-2H-pyran-4-carboxylic Acid

2

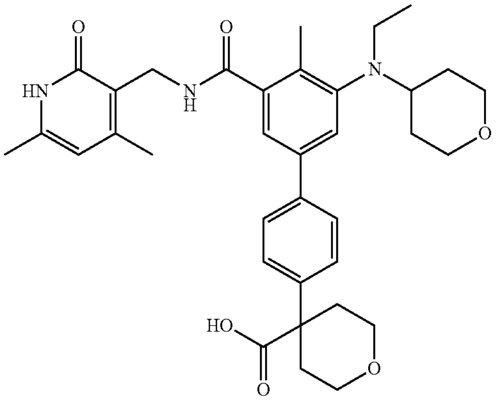

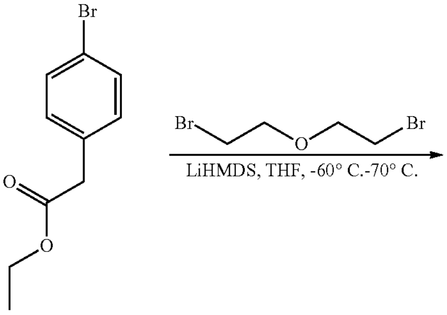

2a

-continued

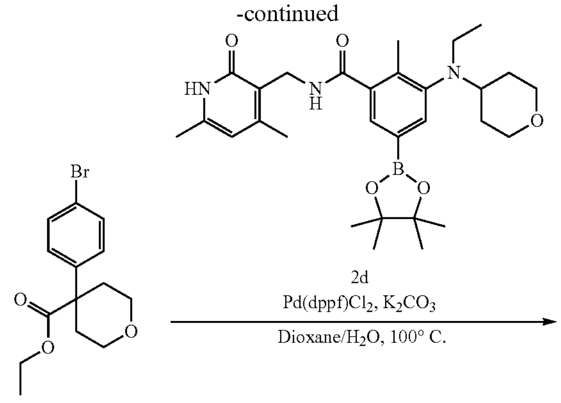

2d

2b

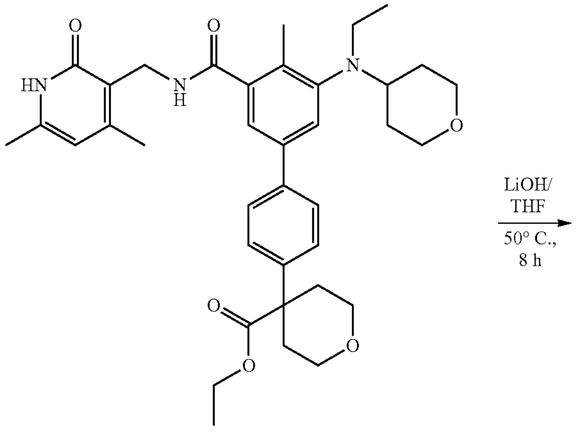

2
c

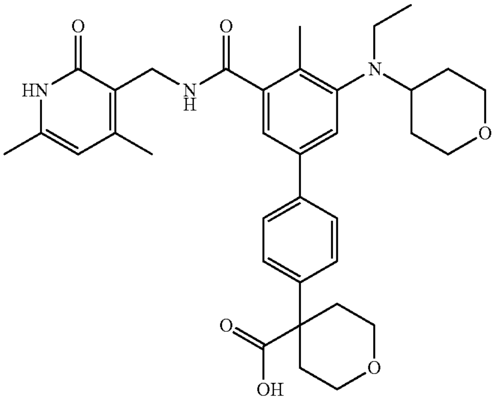

2

Step 1

4-(4-bromophenyl)tetrahydro-2H-pyran-4-carboxylic Acid Ethyl Ester 2b

Compound 2a (3 g, 12.35 mmol) and 1-bromo-2-(2-bromoethoxy)ethane (5.73 g, 24.70 mmol) were dissolved in dry THF (50 mL) under the protection of nitrogen, which was cooled to −78° C. in a dry ice acetone bath, and LiHMDS (49.4 ml, 49.4 mmol) was slowly added dropwise. After the addition was completed, the dry ice acetone bath was removed, and the reaction solution was slowly warmed to room temperature and then heated to 70° C. and stirred for 2 hours. The reaction was quenched with saturated aqueous ammonium chloride solution, which was extracted with EA (30 ml×3). The organic phases were combined, dried over anhydrous sodium sulfate, concentrated and sampled, and purified by column chromatography (petroleum ether:ethyl acetate=0%-40%) to obtain the title compound 2b (2.0 g, 6.39 mmol) as a white solid with a yield of 51.7%.

MS m/z (ESI): 313.1 $[M+H]^+$.

Step 2 Ethyl 4-(3'-(((4,6-dimethyl-2-carbonyl-1,2-dihydropyridin-3-yl)methyl) carbamoyl)-5'-(ethyl (tetrahydro-2H-pyran-4-yl)amino)-4'-methyl-[1,1'-biphenyl]-4-yl)tetrahydro-2H-pyran-4-carboxylic Acid 2c Compound 2b (85 mg, 0.287 mmol) was dissolved in 3 ml of 1,4-dioxane, and compound 2d (150 mg, 0.287 mmol), Pd(dppf)Cl$_2$ (21 mg, 0.0287 mmol), potassium carbonate (79 mg, 0.574 mmol) and 1 ml of water were added in sequence under nitrogen protection, which were heated to 100° C. for 3 hours. After cooling to room temperature, 3 ml of water was added to dilute, which was extracted with EA (5 ml×3). The organic phases were combined, washed with saturated brine, dried and sampled, purified by column chromatography (methanol/dichloromethane=0%-10%) to obtain the title compound 2c (100 mg, 0.159 mmol), white solid, yield 55.30%.

MS m/z (ESI): 630.8 $[M+H]^+$.

Step 3 4-(3'-(((4,6-dimethyl-2-carbonyl-1,2-dihydro-pyridin-3-yl)methyl) carbamoyl)-5'-(ethyl(tetra-hydro-2H-pyran-4-yl)amino)-4'-methyl-[1,1'-biphe-nyl]-4-yl)tetrahydro-2H-pyran-4-carboxylic Acid 2

Compound 2c (80 mg, 0.127 mmol) was dissolved in MeOH/H$_2$O (3 ml/3 ml), and LiOH (30 mg, 1.27 mmol) was added, which was heated to 50° C. and stirred for 8 h. Acetic acid was used to adjust pH=7, and the target compound 2 (50 mg, 0.0832 mmol) was obtained by reverse phase separation and purification (MeCN/water=0%-90%) with a yield of 65.5%.

$^1$H NMR (400 MHz, Methanol-d4) δ 7.58-7.52 (m, 2H), 7.48 (d, J=8.6 Hz, 2H), 7.44 (d, J=1.9 Hz, 1H), 7.30 (d, J=1.8 Hz, 1H), 6.09 (d, J=1.0 Hz, 1H), 4.46 (s, 2H), 3.89 (dd, J=11.9, 3.9 Hz, 4H), 3.67-3.57 (m, 2H), 3.38-3.30 (m, 2H), 3.18-3.04 (m, 3H), 2.50 (d, J=12.8 Hz, 2H), 2.37 (s, 3H), 2.30 (s, 3H), 2.22 (d, J=0.9 Hz, 3H), 2.00-1.90 (m, 2H), 1.73 (d, J=12.6 Hz, 2H), 1.62 (dd, J=12.2, 4.4 Hz, 2H), 0.88 (t, J=7.0 Hz, 3H).

MS m/z (ESI): 602.6 $[M+H]^+$.

Example 3 N-((4,6-dimethyl-2-carbonyl-1,2-dihydropyridin-3-yl)methyl)-5-(ethyl(tetrahydro-2H-pyran-4-yl)amino)-4'-(4-(hydroxymethyl)tetrahydro-2H-pyran-4-yl)-4-methyl-[1,1'-biphenyl]-3-carboxamide

3

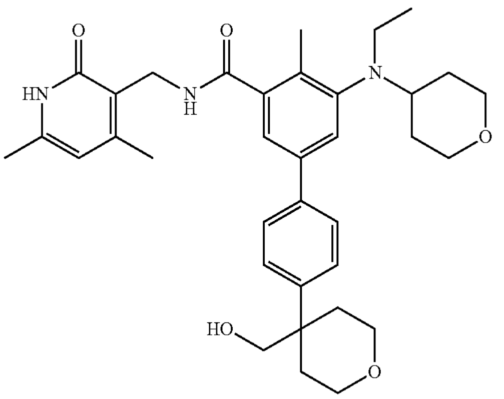

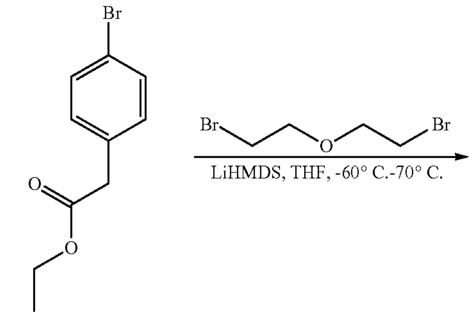

3a

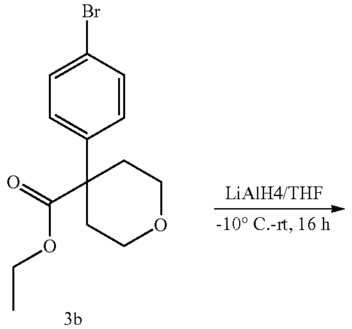

3b

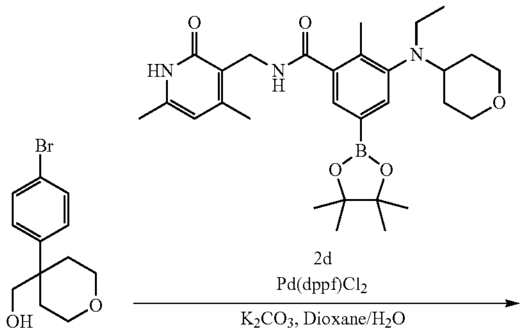

3c

-continued

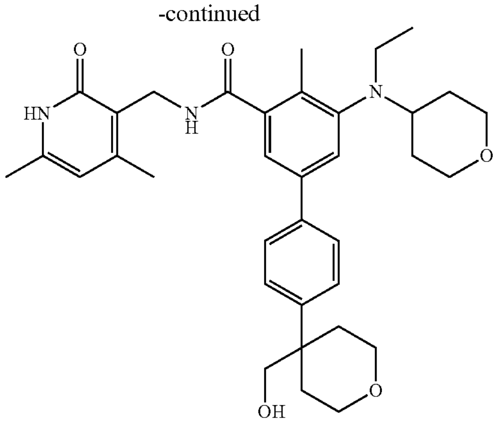

3

Step 1 4-(4-bromophenyl)tetrahydro-2H-pyran-4-carboxylic Acid Ethyl Ester 3b Compound 3a (3 g, 12.35 mmol) and 1-bromo-2-(2-bromoethoxy)ethane (5.73 g, 24.70 mmol) were dissolved in dry THF (50 mL) under the protection of nitrogen, which was cooled to −78° C. in a dry ice acetone bath, and LiHMDS (49.4 ml, 49.4 mmol) was slowly added dropwise. After the addition was completed, the dry ice acetone bath was removed, and the reaction solution was slowly warmed to room temperature and then heated to 70° C. and stirred for 2 hours. The reaction was quenched with saturated aqueous ammonium chloride solution, which was extracted with EA (30 ml×3). The organic phases were combined, dried over anhydrous sodium sulfate, concentrated and sampled, and purified by column chromatography (petroleum ether:ethyl acetate=0%-40%) to obtain the title compound 3b (2.0 g, 6.39 mmol) as a white solid with a yield of 51.7%.

MS m/z (ESI): 313.1 $[M+H]^+$.

Step 2 (4-(4-bromophenyl)tetrahydro-2H-pyran-4-yl)methanol 3c

Compound 3b (500 mg, 1.68 mmol) was dissolved in dry THF (20 mL) under the protection of nitrogen, which was cooled to −5° C. with ice salt and stirred for 10 min, and $LiAlH_4$ (2 ml, 2.5M in THF) was slowly added dropwise. After the addition was completed, it was naturally warmed to room temperature and then stirred overnight. Water (1 ml) was slowly dropped to quench the reaction. Citric acid aqueous solution (10 ml) was added and stirred for 5 minutes, which was then extracted with EA (15 ml×3). The organic phases were combined, washed once with saturated sodium chloride aqueous solution, dried over anhydrous sodium sulfate, concentrated and sampled, and purified by column chromatography (petroleum ether:ethyl acetate=0%-40%) to obtain the title compound 3c (300 mg, 1.11 mmol) as a white solid with a yield of 65.9%.

MS m/z (ESI): 294.9 $[M+Na]^+$.

Step 3 N-((4,6-dimethyl-2-carbonyl-1,2-dihydropyridin-3-yl)methyl)-5-(ethyl (tetrahydro-2H-pyran-4-yl)amino)-4'-(4-(hydroxymethyl)tetrahydro-2H-pyran-4-yl)-4-methyl-[1,1'-biphenyl]-3-carboxamide 3

Compound 3c (100 mg, 0.369 mmol) was dissolved in 3 ml of 1,4-dioxane, and compound 2d (193 mg, 0.369 mmol), Pd(dppf)$Cl_2$ (27 mg, 0.0369 mmol), potassium carbonate (102 mg, 0.738 mmol) and 1 ml of water were added in sequence under nitrogen protection, which was heated to 100° C. for 3 hours. After cooling to room temperature, 3 ml of water was added to dilute, which was extracted with EA (5 ml×3). The organic phases were combined, washed with saturated brine, dried and sampled, purified by column chromatography (methanol/dichloromethane=0%-10%) to obtain the title compound 3 (65 mg, 0.111 mmol), white solid, yield 30%.

$^1$H NMR (400 MHz, Methanol-d4) δ 7.56 (d, J=8.4 Hz, 2H), 7.43 (d, J=8.2 Hz, 3H), 7.31 (d, J=1.9 Hz, 1H), 6.09 (s, 1H), 4.47 (s, 2H), 3.90 (d, J=11.4 Hz, 2H), 3.79 (dt, J=11.6, 4.0 Hz, 2H), 3.58-3.45 (m, 4H), 3.34 (dd, J=12.4, 10.2 Hz, 2H), 3.17-3.04 (m, 3H), 2.37 (s, 3H), 2.30 (s, 3H), 2.22 (s, 3H), 2.15 (d, J=13.9 Hz, 2H), 2.00-1.91 (m, 2H), 1.74 (d, J=12.8 Hz, 2H), 1.63 (tt, J=11.9, 6.0 Hz, 2H), 0.88 (t, J=7.0 Hz, 3H).

MS m/z (ESI): 588.4 [M+H]$^+$.

Example 4 N-((4,6-dimethyl-2-carbonyl-1,2-dihydropyridin-3-yl)methyl)-3-(ethyl(tetrahydro-2H-pyran-4-yl)amino)-2-methyl-5-(1-morpholino-2,3-dihydro-1H-inden-5-yl)benzamide

4

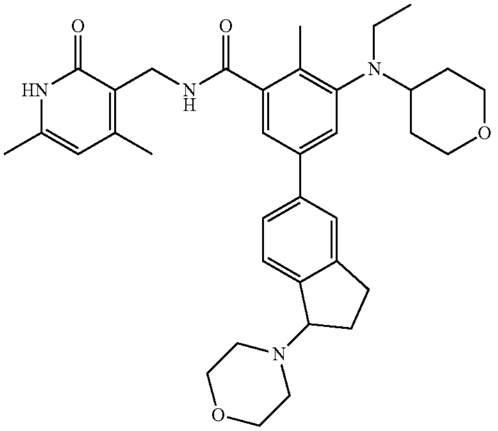

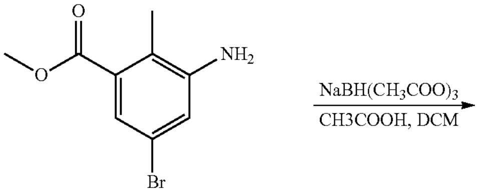

4a

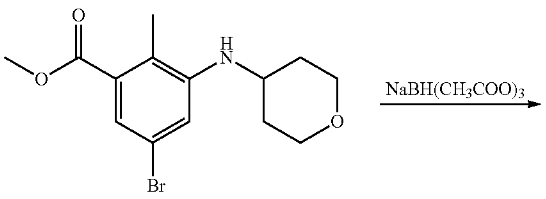

4b

-continued

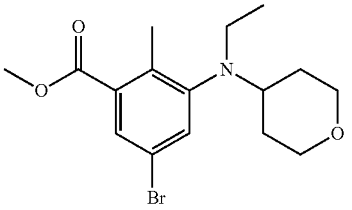

4c

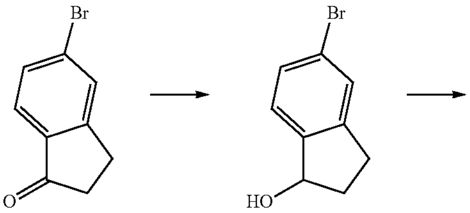

4d

4e

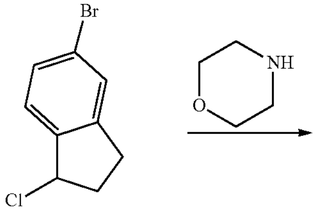

4f

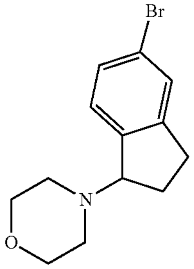

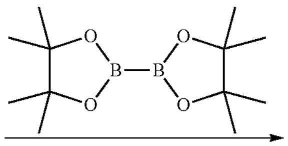

4g

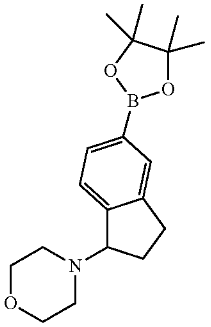

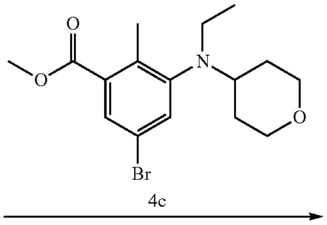

4c

4h

-continued

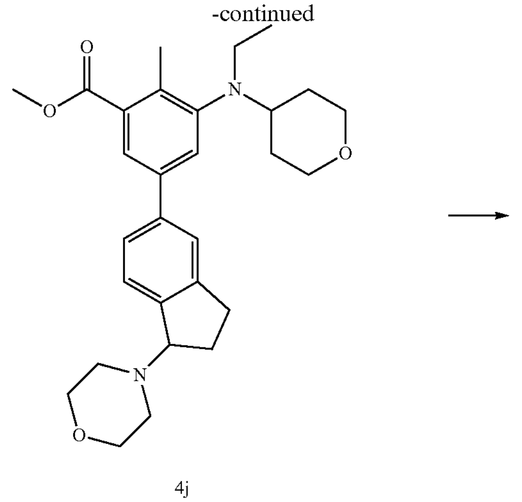

4j

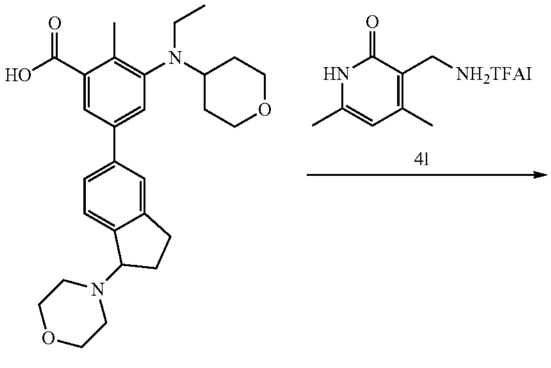

4l

4k

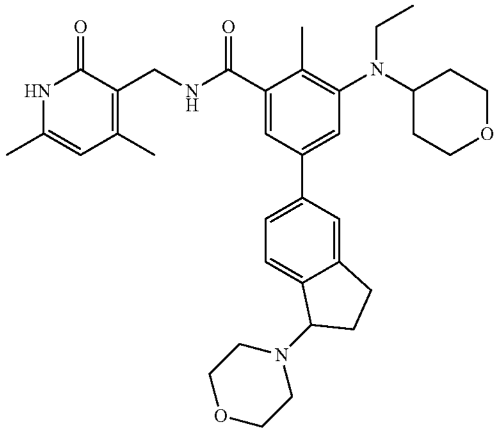

4

Step 1 methyl 5-bromo-2-methyl-3-((tetrahydro-2H-pyran-4-yl)amino)benzoate 4b

Compound 4a (20 g, 81.9 mmol) was dissolved in dichloromethane (200 mL), acetic acid (14.7 g, 245.0 mmol) and tetrahydropyrone (16.3 g, 163.9 mmol) were added. After the reaction was stirred at room temperature for 30 minutes, sodium triacetoxyborohydride (52 g, 245.8 mmol) was added, and stirring at room temperature for 4 h. The reaction was completed. The reaction solution was quenched with water, which was extracted with dichloromethane three times. The organic phases were washed with saturated brine, dried over anhydrous sodium sulfate, filtered, and concentrated to obtain the title compound 4b (26.7 g, 81.9 mmol) with a yield of 100%.

MS m/z (ESI): 328 $[M+H]^+$.

Step 2 methyl 5-bromo-3-(ethyl(tetrahydro-2H-pyran-4-yl)amino)-2-methylbenzoate 4c Compound 4b (26.7 g, 81.9 mmol) was dissolved in dichloromethane (200 mL), acetic acid (14.7 g, 245 mmol) and acetaldehyde (18 g, 410 mmol) were added. After the reaction was stirred at room temperature for 30 minutes, sodium triacetoxyborohydride (52 g, 246 mmol) was added, and stirring at room temperature for 4 h. The reaction was completed. The reaction solution was quenched with water, which was extracted with dichloromethane three times. The organic phases were washed with saturated brine, dried over anhydrous sodium sulfate, filtered, concentrated and purified by column chromatography to obtain the title compound 4c (27 g, 75 mmol) with a yield of 91%.

MS m/z (ESI): 356 $[M+H]^+$.

Step 3 5-bromo-2,3-dihydro-1H-inden-1-ol 4e

In a 1 L three-necked flask, compound 4d (75 g, 355 mmol) and MeOH (500 mL) were added, and $NaBH_4$ (27 g, 711 mmol) was slowly added under ice bath, which was heated to 15° C., and the reaction was carried out for 1.5 h. TLC monitoring showed that the raw material was completely reacted and new spots were formed. The reaction solution was quenched with $H_2O$, concentrated, filtered, washed with water, and drained until dried to obtain a white solid compound 4e (72 g, 338 mmol) with a yield of 95%.

Step 4 5-bromo-1-chloro-2,3-dihydro-1H-indene 4f

Compound 4e (72 g, 338 mmol) was dissolved in DCM (400 mL), and $SOCl_2$ (196 mL, 2.7 mol) was slowly added in an ice bath. After the ice bath was removed, the reaction was carried out at room temperature for 4 h. TLC detection showed that the raw material was completely reacted. The reaction solution was concentrated to remove the solvent and dried in vacuo to obtain compound 4f (81 g, 350 mmol) as a brown oil.

Step 5 4-(5-bromo-2,3-dihydro-1H-inden-1-yl)morpholine 4g

In a 100 mL single-neck flask, compound 4f (76 g, 328 mmol), $K_2CO_3$ (227 g, 1.6 mmol), NaI (49 g, 328 mmol), $CH_3CN$ (800 mL), and morpholine (72 g, 821 mmol) were added under the protection of $N_2$, which was slowly heated to 70° C. and reacted for 4 h. TLC detection showed that the raw material was completely reacted. The reaction solution was cooled to room temperature, diluted with EA (300 mL), and filtered to remove the solids. The liquid was concentrated and mixed, and purified by column chromatography (EA/PE=0%-40%) to obtain a pale red solid compound 4g (65 g, 230 mmol) with a yield of 70%. In a 100 mL single-neck flask, compound 4f (76 g, 328 mmol), $K_2CO_3$ (227 g, 1.6 mmol), NaI (49 g, 328 mmol), $CH_3CN$ (800 mL), and morpholine (72 g, 821 mmol) were added under the protection of nitrogen, which was slowly heated to 70° C. and reacted for 4 h. TLC detection showed that the raw material was completely reacted. The reaction solution was cooled to room temperature, diluted with EA (300 mL), and filtered to remove the solids. The liquid was concentrated and mixed, and purified by column chromatography (EA/PE=0%-40%) to obtain a pale red solid compound 4g (65 g, 230 mmol) with a yield of 70%.

Step 6 4-(5-(4,4,5,5-tetramethyl-1,3,2-dioxaborolan-2-yl)-2,3-dihydro-1H-inden-1-yl)morpholine 4h Compound 4g (30 g, 106.3 mmol) was dissolved in dry dioxane (300 mL), and then pinacol diborate (35 g, 138 mmol), KOAc (26 g, 265.8 mmol) and Pd(dppf)$Cl_2$ (5.45 g, 7.44 mmol) were added in sequence under the protection of nitrogen, which was heated to 100° C. and reacted for 3 hours. After cooling to room temperature, the resultant was diluted with EA (200 mL), filtered through celite to remove the solids. The filtrate was concentrated and sampled, and purified by Flash column. A pale red solid compound 4h (25 g, 76 mmol) was obtained with a yield of 71%.

Step 7 methyl 3-(ethyl(tetrahydro-2H-pyran-4-yl)amino)-2-methyl-5-(1-morpholino-2,3-dihydro-1H-inden-5-yl)benzoate 4j Compound 4h (15 g, 45.56 mmol) was dissolved in a mixed solvent of dioxane/$H_2O$ (200 mL/60 mL), and then compound 28c (16.23 g, 45.56 mmol), $K_2CO_3$ (18.89 g, 136.68 mmol) and Pd(dppf)$Cl_2$ (3.33 g, 4.56 mmol) were added in sequence under argon protection, which was heated to 100° C. and reacted for 1 h. The reaction solution was concentrated, diluted with EA (200 mL), and filtered through celite. The filtrate was concentrated and sampled, and purified by Flash column. A pale red solid compound 4j (13 g, 27.16 mmol) was obtained.

Step 8 3-(ethyl(tetrahydro-2H-pyran-4-yl)amino)-2-methyl-5-(1-morpholino-2,3-dihydro-1H-inden-5-yl)benzoic Acid 4k Compound 4j (13 g, 27 mmol) was dissolved in a mixed solvent of MeOH/$H_2O$ (200 mL/50 mL), and then NaOH (10.86 g, 271.6 mmol) was added, which was heated to 60° C. and stirred for 1.5 h. LCMS detection showed that the raw material was completely reacted. The reaction solution was concentrated to remove most of the methanol, diluted with water, adjusted to a weakly acidic pH with dilute hydrochloric acid, and extracted with DCM. The organic phase was dried over anhydrous sodium sulfate, and concentrated to obtain a pale red solid compound 4k (11 g, 23.68 mmol) with a yield of 87%.

Step 9 N-((4,6-dimethyl-2-carbonyl-1,2-dihydropyridin-3-yl)methyl)-3-(ethyl (tetrahydro-2H-pyran-4-yl)amino)-2-methyl-5-(1-morpholino-2,3-dihydro-1H-inden-5-yl)benzamide 4

In a 250 mL single-neck flask, compound 4k (5.5 g, 11.84 mmol), compound 41 (2.95 g, 11.84 mmol), EDCI (3.4 g, 17.76 mmol), HOBt (1.28 g, 9.47 mmol), DMF (60 mL), and DIPEA (12 mL, 0.75 g/mL, 71 mmol) were added in sequence, which was heated to 50° C. and stirred for 2 h. LCMS detection showed that the raw material was completely reacted. The reaction solution was poured into a large amount of water, and a large amount of solids precipitated, which was filtered. The solids were dissolved with DCM, washed with water, and the organic phase was concentrated, which was mixed with silica gel, and purified by Flash column to obtain a pale yellow solid 4 (4.2 g, 7 mmol) with a yield of 59%.

$^1H$ NMR (400 MHz, Methanol-d4) δ 7.47-736 (m, 4H), 7.29 (d, J=1.9 Hz, 1H), 6.10 (s, 1H), 4.48 (s, 2H), 4.30 (dd, J=7.7, 5.2 Hz, 1H), 3.96-3.85 (m, 2H), 3.68 (dt, J=6.6, 3.4 Hz, 4H), 3.39-3.32 (m, 2H), 3.18-3.04 (m, 3H), 2.94 (ddd, J=38.7, 8.6, 6.4 Hz, 2H), 2.64-2.45 (m, 4H), 2.38 (s, 3H), 2.31 (s, 3H), 2.27-2.11 (m, 5H), 1.74 (d, J=12.9 Hz, 2H), 1.64 (td, J=11.7, 4.0 Hz, 2H), 0.89 (t, J=6.9 Hz, 3H).

MS m/z (ESI): 599.5 [M+H]+.

Example 5 N-((4,6-dimethyl-2-carbonyl-1,2-dihydropyridin-3-yl)methyl)-5-(ethyl(tetrahydro-2H-pyran-4-yl)amino)-4'-(4-(methoxymethyl)tetrahydro-2H-pyran-4-yl)-4-methyl-[1,1'-biphenyl]-3-carboxamide

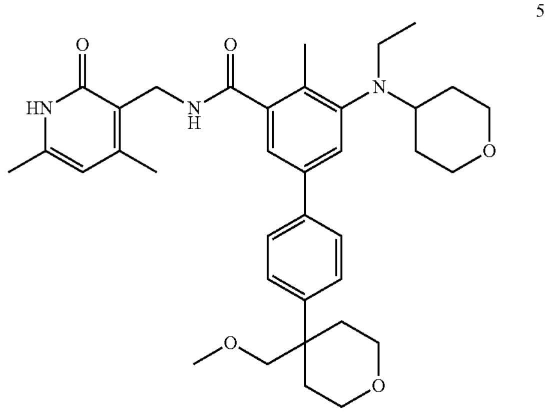

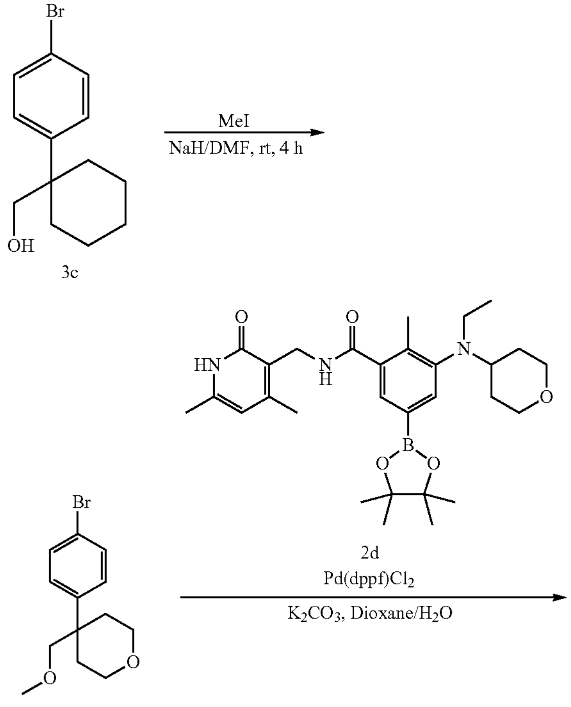

-continued

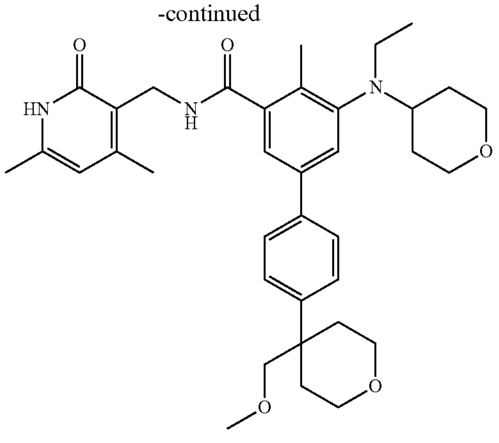

5

Step 1: 4-(4-bromophenyl)-4-(methoxymethyl)tetrahydro-2H-pyran 5a

Compound 3c (300 mg, 1.11 mmol) was dissolved in DMF (5 mL), and NaH (107 mg, 4.44 mmol) was added under ice bath conditions. After the reaction solution was stirred at room temperature for 30 min, Mel (316 mg, 2.22 mmol) was added, and stirring was continued overnight. Water/EA (10 ml/10 ml) was added, stirred for 5 min and then separated. The water phase was extracted with EA (10 ml×3). The organic phases were combined, washed with saturated sodium chloride aqueous solution (15 ml×3), dried over anhydrous sodium sulfate, concentrated and sampled, and purified by column chromatography (petroleum ether: ethyl acetate=0%-40%) to obtain the title compound 5a (200 mg, 0.702 mmol) as a white solid with a yield of 63.2%.

MS m/z (ESI): 287 $[M+H]^+$.

Step 2 N-((4,6-dimethyl-2-carbonyl-1,2-dihydropyridin-3-yl)methyl)-5-(ethyl (tetrahydro-2H-pyran-4-yl)amino)-4'-(4-(methoxymethy)tetrahydro-2H-pyran-4-yl)-4-methyl-[1,1'-biphenyl]-3-carboxamide 5

Compound 5a (100 mg, 0.351 mmol) was dissolved in 3 ml of 1,4-dioxane, and compound 2d (184 mg, 0.351 mmol), $Pd(dppf)Cl_5$ (26 mg, 0.0351 mmol), potassium carbonate (97 mg, 0.702 mmol) and 1 ml of water were added in sequence under nitrogen protection, which was heated to 100° C. for 3 hours. After cooling to room temperature, 3 ml of water was added to dilute, which was extracted with EA (5 ml×3). The organic phases were combined, washed with saturated brine, dried and sampled, purified by column chromatography (methanol/dichloromethane=0%-10%) to obtain the title compound 5 (45 mg, 0.0748 mmol), white solid, yield 21.3%.

$^1H$ NMR (400 MHz, Methanol-d4) δ 7.59-7.51 (m, 2H), 7.48-7.40 (m, 3H), 7.31 (d, J=1.8 Hz, 1H), 6.09 (s, 1H), 4.47 (s, 2H), 3.90 (d, J=11.4 Hz, 2H), 3.77 (dt, J=11.6, 4.2 Hz, 2H), 3.52 (ddd, J=12.1, 9.9, 2.6 Hz, 2H), 3.40-3.30 (m, 4H), 3.22-3.02 (m, 6H), 2.38 (s, 3H), 2.30 (s, 3H), 2.22 (d, J=0.9 Hz, 3H), 2.15 (d, J=14.0 Hz, 2H), 1.98 (ddd, J=13.9, 9.9, 3.9 Hz, 2H). 1.74 (d, J=13.1 Hz, 2H), 1.63 (tt, J=1.9, 5.9 Hz, 2H), 0.88 (t, J=7.0 Hz, 3H).

MS m/z (ESI): 602.7 $[M+H]^+$.

Example 6 3-(ethyl(tetrahydro-2H-pyran-4-yl)amino)-N-((4-methoxy-6-methyl-2-oxo-1,2-dihydropyridin-3-yl)methyl)-2-methyl-5-(1-morpholino-2,3-dihydro-1H-inden-5-yl)benzamide

6

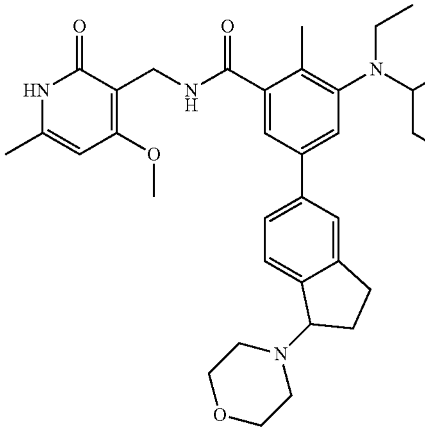

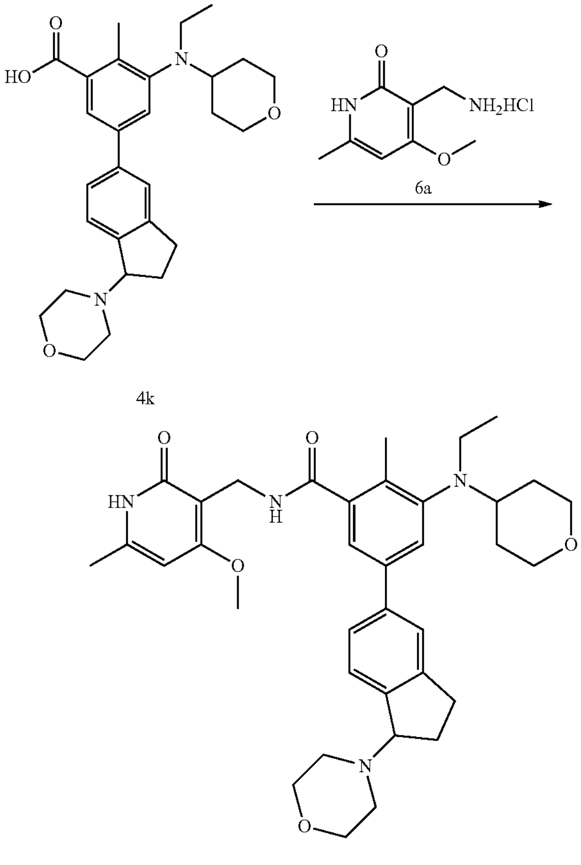

4k

6a

6

Step 1 3-(ethyl(tetrahydro-2H-pyran-4-yl)amino)-N-((4-methoxy-6-methyl-2-oxo-1,2-dihydropyridin-3-yl)methyl)-2-methyl-5-(1-morpholino-2,3-dihydro-1H-inden-5-yl)benzamide 6

In a 250 mL single-neck flask, compound 4k (5.5 g, 11.84 mmol), compound 6a (2.95 g, 11.84 mmol), EDCI (3.4 g, 17.76 mmol), HOBt (1.28 mg, 9.47 mmol), DMF (80 mL), and DIPEA (14.28 mL, 0.75 g/mL, 82.87 mmol) were added, which was heated to 50° C. and stirred for 2 h. TLC detection showed that the raw material was completely reacted. The reaction solution was poured into water and a solid precipitated out, which was stirred for 5 minutes, and filtered. The solid was dissolved with DCM, washed with saturated brine, concentrated, mixed with silica gel, and purified by Flash column to obtain a pale yellow solid 45 (3.9 g, 6.5 mmol) with a yield of 55%.

$^1$H NMR (400 MHz, Methanol-d4) δ 7.40 (dd, J=6.6, 1.9 Hz, 4H), 7.29 (d, J=1.8 Hz, 1H), 6.24 (s, 1H), 4.45 (s, 2H), 4.30 (dd, J=7.6, 5.2 Hz, 1H), 3.91 (s, 5H), 3.67 (dt, J=65, 3.4 Hz, 4H), 3.34 (dd, J=12.3, 10.2 Hz, 2H), 3.18-2.95 (m, 4H), 2.86 (ddd, J=15.7, 8.7, 5.8 Hz, 1H), 2.59 (dt, J=9.6, 4.4 Hz, 2H), 2.54-2.45 (m, 2H), 2.30 (d, J=13.0 Hz, 6H), 2.23-2.07 (m, 2H), 1.78-1.56 (m, 4H), 0.88 (t, J=7.0 Hz, 31H).

MS m/z (ESI): 615.5 [M+H]$^+$.

Example 7 N-((4,6-dimethyl-2-oxo-1,2-dihydropyridin-3-yl)methyl)-3-(ethyl (tetrahydro-2H-pyran-4-yl)amino)-2-methyl-5-(1-neopentyl 2',3',5',6'-tetrahydro spiro[indoline-3,4'-pyran]-6-yl)benzamide

7

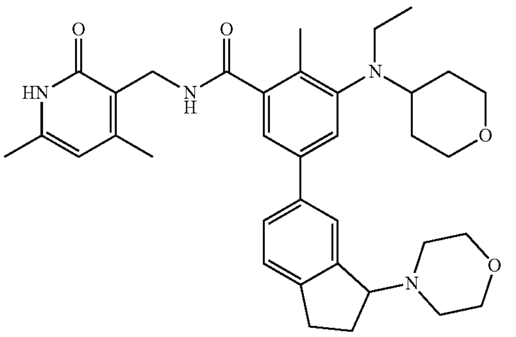

Using a synthesis method similar to that in Example 4, replacing 5-bromo-2,3-dihydro-1H-inden-1-one with 6-bromo-2,3-dihydro-1H-inden-1-one, the title product 7 was obtained with a yield of 14.7%.

MS m/z (ESI): 599 [M+H]$^+$.

Example 8 3-(ethyl(tetrahydro-2H-pyran-4-yl) amino)-N-((4-methoxy-6-methyl-2-carbonyl-1,2-dihydropyridin-3-yl)methyl)-2-methyl-5-(3-morpholino-2,3-dihydro-1H-inden-5-yl)benzamide

8

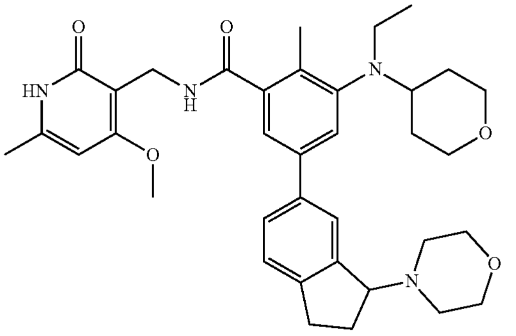

Using a synthesis method similar to that of Example 4, replacing 5-bromo-2,3-dihydro-1H-inden-1-one with 6-bromo-2,3-dihydro-1H-inden-1-one, and replacing 3-(aminomethyl)-4,6-dimethyl-1H-pyridin-2-one hydrochloride with 3-(aminomethyl)-4-methoxy-6-methyl-1H-pyridin-2-one hydrochloride, the title product 8 was obtained with a yield of 14.7%.

$^1$H NMR (400 MHz, DMSO-$d_6$) δ 11.38 (s, 1H), 7.97 (t, J=4.5 Hz, 1H), 7.41 (d, J=9.5 Hz, 2H), 7.34-7.23 (m, 2H), 7.13 (d, J=1.8 Hz, 1H), 6.06 (s, 1H), 4.34-4.13 (m, 3H), 3.81 (s, 4H), 3.62-3.38 (m, 4H), 3.22 (t, J=11.5 Hz, 2H), 3.16-3.08 (m, 1H), 3.10-2.69 (m, 5H), 2.46 (s, 2H), 2.34 (d, J=8.0 Hz, 2H), 2.28-1.88 (m, 8H), 1.67-1.39 (m, 4H), 0.81 (t, J=6.9 Hz, 3H).

MS m/z (ESI): 615 [M+H]$^+$.

Example 9 2-chloro-4'-(4-cyanotetrahydro-2H-pyran-4-yl)-N-((4,6-dimethyl-2-oxo-1,2-dihydropyridin-3-yl)methyl)-5-(ethyl(tetrahydro-2H-pyran-4-yl)amino)-4-methyl-[1,1'-biphenyl]-3-formamide

9

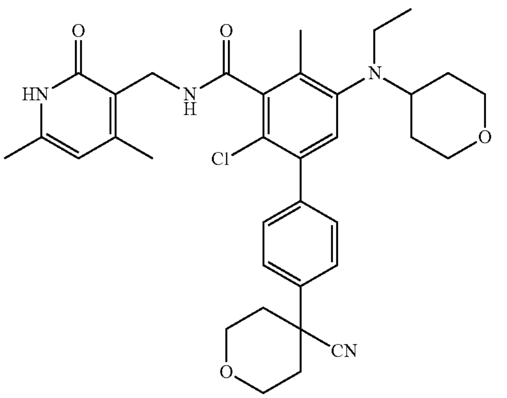

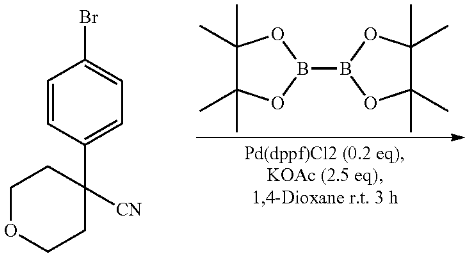

1b

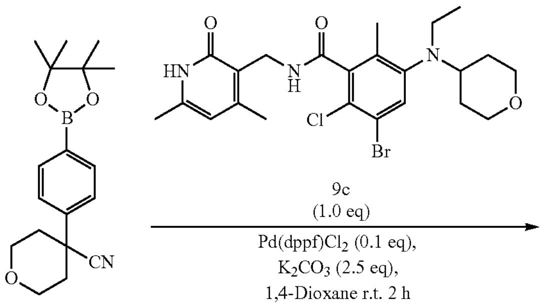

9b

-continued

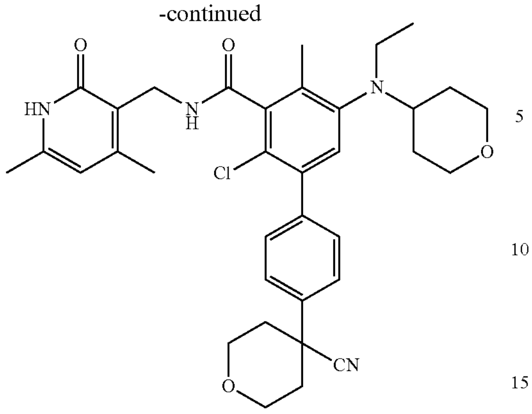

9

Step 1 4-(4-(4,4,5,5-tetramethyl-1,3,2-dioxaborolan-2-yl)phenyl)tetrahydro-2H-pyran-4-carbonitrile 9b Compound 1b (see Example 1 for the synthesis method) (400 mg, 1.503 mmol), pinacol diborate (573 mg, 2.25 mmol), Pd(dppf)$Cl_2$ (220 mg, 0.3 mmol), potassium acetate (442 mg, 4.5 mmol), and 20 ml of 1,4-dioxane were added to a 100 ml single-necked flask, and performing nitrogen replacement, which was heated to 100° C. and stirred for 2 h. The resultant was extracted with water and EA, dried with anhydrous sodium sulfate, mixed and concentrated, and purified by column chromatography (petroleum ether:ethyl acetate=3:1) to obtain the title compound 9b (470 mg, 1.501 mmol) with a yield of 99.9%.

MS m/z (ESI): 314 $[M+H]^+$.

Step 2 2-chloro-4'-(4-cyanotetrahydro-2H-pyran-4-yl)-N-((4,6-dimethyl-2-oxo-1,2-dihydropyridin-3-yl)methyl)-5-(ethyl(tetrahydro-2H-pyran-4-yl)amino)-4-methyl-[1,1'-biphenyl]-3-formamide 9

Compound 9b (120 mg, 0.383 mmol), compound 9c (195 mg, 0.383 mmol), Pd(dppf)$Cl_2$ (28 mg, 0.0383 mmol), potassium carbonate (160 mg, 1.15 mmol), 1 ml of water, and 5 ml of 1,4-dioxane were added to a 50 ml single-necked flask, and performing nitrogen replacement, which was heated to 100° C. and stirred for 1 hour. Water and EA were added for extraction twice. The organic phase was dried, concentrated and sampled for column chromatography to obtain the title compound 9 (80 mg, 0.130 mmol) with a yield of 34%.

$^1H$ NMR (400 MHz, DMSO-$d_6$) δ 11.42 (s, 1H), 8.35 (t, J=4.9 Hz, 1H), 7.60 (d, J=8.4 Hz, 2H), 7.42 (d, J=8.3 Hz, 2H), 7.06 (s, 1H), 5.81 (s, 1H), 4.24 (s, 2H), 4.00 (d, J=11.4 Hz, 2H), 3.79 (d, J=11.2 Hz, 2H), 3.72-3.56 (m, 2H), 3.20 (t, J=11.2 Hz, 2H), 2.96 (dd, J=17.0.8 Hz, 3H), 2.31-1.93 (m, 11H), 1.60 (d, J=12.2 Hz, 2H), 1.53-1.38 (m, 2H), 0.79 (t, J=6.9 Hz, 3H).

MS m/z (ESI): 617 $[M+H]^+$.

Example 10 2-chloro-N-((4,6-dimethyl-2-oxo-1,2-dihydropyridin-3-yl)methyl)-5-(ethyl(tetrahydro-2H-pyran-4-yl)amino)-6-methyl-3-(1-morpholino-2,3-dihydro-1H-inden-5-yl)benzamide

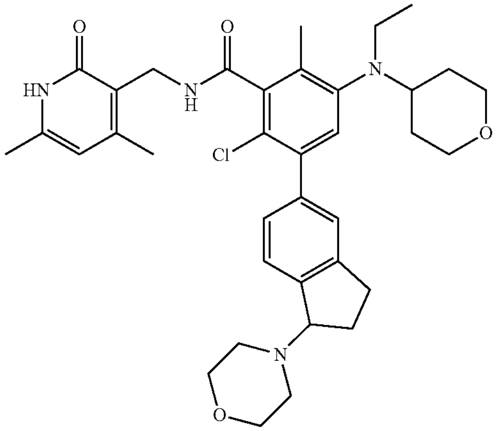

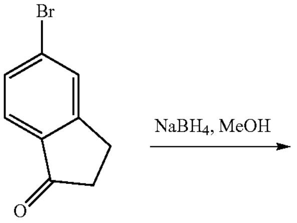

4d

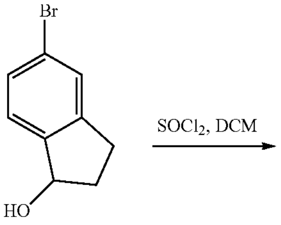

4e

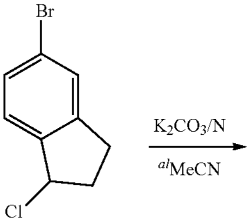

4f

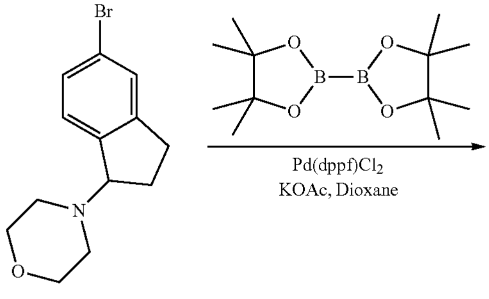

4g

-continued

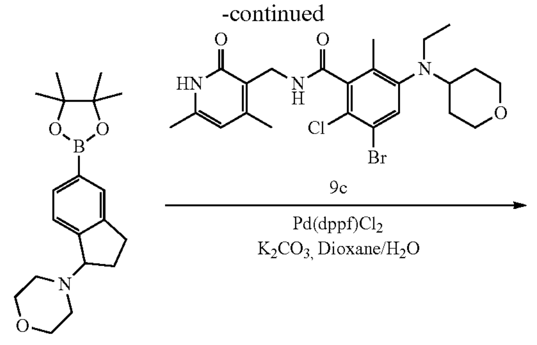

4h

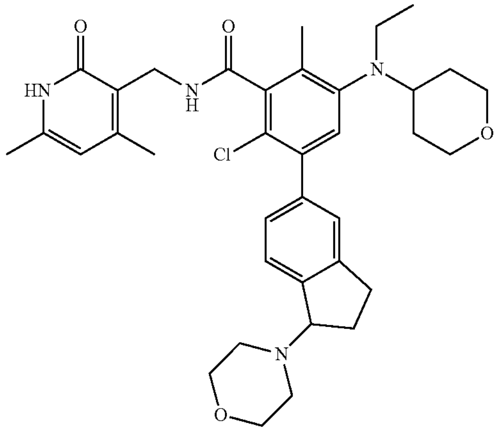

10

Step 1 5-bromo-2,3-dihydro-1H-indene-1-ol 4e

Compound 4d (3.7 g, 17.54 mmol) was dissolved in MeOH (100 mL), $NaBH_4$ (2.0 g 52.63 mmol) was added to the reaction solution in batches, and stirred at room temperature for 2 h. Water (30 ml) was added, stirred for 5 min, and then concentrated to remove most of the methanol, extracted with DCM (30 ml×3). The organic phases were combined, and washed once with saturated sodium chloride aqueous solution, dried over anhydrous sodium sulfate, concentrated and sampled, and purified by column chromatography (petroleum ether:ethyl acetate=0%-40%) to obtain the title compound 4e (3.2 g, 15.02 mmol) as a white solid with a yield of 85.6%.

MS m/z (ESI): 234.9 $[M+Na]^+$.

Step 2: 5-bromo-1-chloro-2,3-dihydro-1H-indene 4f

Compound 4e (2.0 g, 9.32 mmol) was dissolved in dry DCM (40 mL), and $SOCl_2$ (8 ml) was added, which was stirred at room temperature for 4 hours, concentrated under reduced pressure to remove the solvent, and dried in vacuo to obtain the title compound 4f (2.1 g, crude product), a brown oil, which was directly used in the next reaction without purification.

Step 3
4-(5-bromo-2,3-dihydro-1H-inden-1-yl)morpholine
4g

Compound 4f (530 mg, 2.29 mmol) was dissolved in acetonitrile (20 ml), and the compound morpholine (239 mg, 2.75 mmol), $Cs_2CO_3$ (1.74 g, 4.58 mmol) and KI (760 mg, 4.58 mmol) were added in sequence, which was heated to 80° C. for 4 hours. After cooling to room temperature, 30 ml ethyl acetate was added to dilute, filtered to remove the solid. The liquid was concentrated and sampled, and purified by column chromatography (EA/PE=0%-40%) to obtain the title compound 4g (400 mg, 1.42 mmol) as a pale purple oil with a yield of 62%.

MS m/z (ESI): 282.2$[M+H]^+$.

Step 4 4-(5-(4,4,5,5-tetramethyl-1,3,2-dioxaborolan-2-yl)-2,3-dihydro-1H-inden-1-yl) morpholine 4h Compound 4g (300 mg, 1.06 mmol) was dissolved in 10 ml of 1,4-dioxane, and pinacol diborate (540 mg, 2.13 mmol), $Pd(dppf)Cl_2$ (77 mg, 0.106 mmol) and KOAc (31 mg, 0.318 mmol) were added, and evenly mixed, which was heated to 100° C. and refluxed for 3 hours under $N_2$ protection. After cooling to room temperature, 10 ml of water was added to dilute, which was extracted with EA (10 ml×3). The organic phases were combined, washed with 10 ml saturated brine, dried and sampled, purified by column chromatography (methanol/dichloromethane=0%-10%) to obtain the title compound 4 (250 mg, 0.0757 mmol), yield 71.4%.

MS m/z (ESI): 330.2$[M+H]^+$.

Step 5 2-chloro-N-((4,6-dimethyl-2-oxo-1,2-dihydropyridin-3-yl)methyl)-5-(ethyl(tetrahydro-2H-pyran-4-yl)amino)-6-methyl-3-(1-morpholino-2,3-dihydro-1H-inden-5-yl)benzamide 10

Compound 4h (100 mg, 0.304 mmol) was dissolved in 3 ml of 1,4-dioxane, and compound 9b (144 mg, 0.304 mmol), $Pd(dppf)Cl_2$ (22 mg, 0.0304 mmol), potassium carbonate (84 mg, 0.608 mmol) and 1 ml of water were added in sequence, which were heated to 100° C. for 3 hours under nitrogen protection. After cooling to room temperature, 3 ml of water was added to dilute, which was extracted with EA (5 ml×3). The organic phases were combined, washed with saturated brine, dried and sampled, purified by column chromatography (methanol/dichloromethane=0%-10%) to obtain the title compound 10 (45 mg, 0.0711 mmol), white solid, yield 23.4%.

$^1H$ NMR (400 MHz, Methanol-d4) δ 7.40 (d, J=7.8 Hz, 1H), 7.21-7.08 (m, 3H), 6.07 (s, 1H), 4.47 (s, 2H), 4.34-4.27 (m, 1H), 3.89 (d, J=11.3 Hz, 2H), 3.68 (dt, J=6.6, 3.4 Hz, 4H), 3.38-330 (m, 2H), 3.11-2.94 (m, 4H), 2.90-2.81 (m, 1H), 2.65-2.47 (m, 4H), 2.37 (s, 3H), 2.30-2.08 (m, 8H), 1.71 (d, J=12.6 Hz, 2H), 1.59 (qd, J=11.9, 4.4 Hz, 2H), 0.86 (t, J=7.0 Hz, 3H).

MS m/z (ESI): 633.2 $[M+H]^+$.

Example 11 N-((4,6-dimethyl-2-oxo-1,2-dihydro-pyridin-3-yl)methyl)-3-(ethyl (tetrahydro-2H-pyran-4-yl)amino)-6-fluoro-2-methyl-5-(1-morpholino-2,3-dihydro-1H-inden-5-yl)benzamide
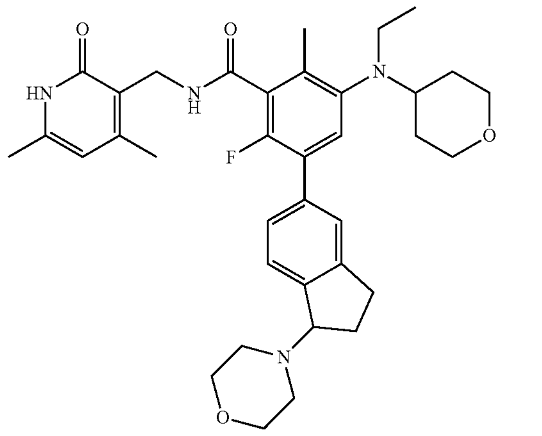
11
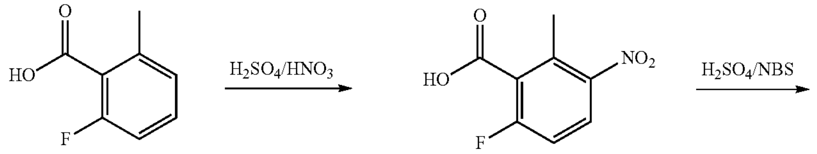
11a 11b
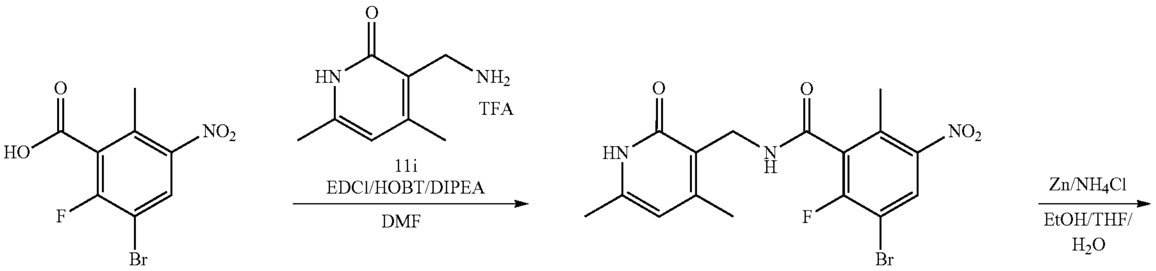
11c 11d
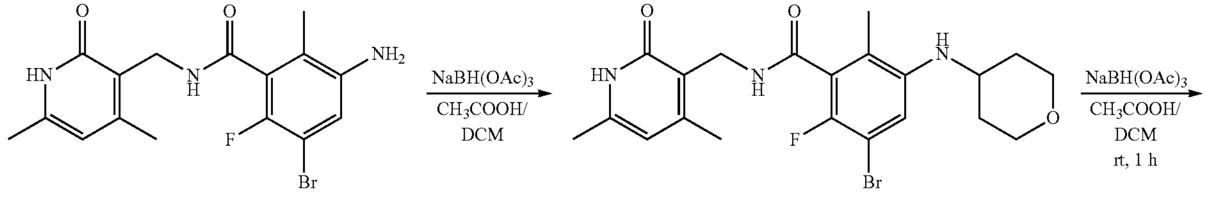
11e 11f
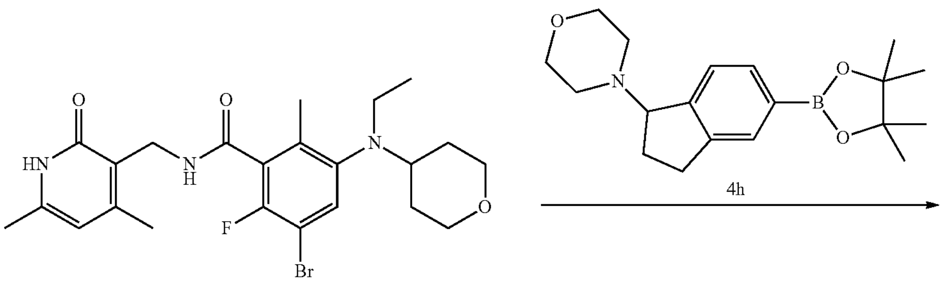
11g -continued

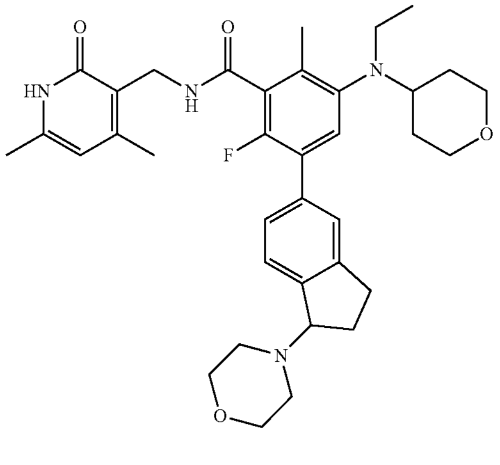

11

Step 1 6-fluoro-2-methyl-3-nitrobenzoic Acid 11b

Concentrated sulfuric acid (40 ml) was added to a 100 ml single-necked flask, cooled to −15° C. in a dry ice bath, and compound 11a (5 g, 32.47 mmol) was added with stirring. Then a mixed acid (fuming nitric acid/concentrated sulfuric acid: 1.75 ml/7.5 ml) was slowly added dropwise to the reaction solution. After the addition was completed, the reaction solution was stirred at 0° C. for 1 h. The reaction solution was poured into a large amount of ice water, and a large amount of solids separated out, which was filtered. The solids were dissolved with EA and then washed with water, dried over anhydrous sodium sulfate, and concentrated to obtain the target compound 11b (5.1 g, 25.6 mmol), a pale yellow solid, yield 78.9%.

Step 2 3-bromo-2-fluoro-6-methyl-5-nitrobenzoic Acid 11c

Compound 11b (4.1 g, 20.6 mmol) was dissolved in concentrated sulfuric acid (100 ml), and NBS (3.85 g, 21.63 mmol) was added. After stirring at room temperature for 6 hours, the reaction solution was poured into a large amount of ice water, and a large amount of solid precipitated out, which was filtered. The solid was washed with water, and dried in vacuo to obtain the target compound 11c (4.4 g, 15.8 mmol) as a pale yellow solid, with a yield of 76.8%.

MS m/z (ESI): 277.8 $[M+H]^+$.

Step 3 3-bromo-N-((4,6-dimethyl-2-oxo-1,2-dihydropyridin-3-yl)methyl)-2-fluoro-6-methyl-5-nitrobenzamide 11d Compound 11c (4.4 g, 15.8 mmol) was dissolved in DMF (20 ml), and then compound 11i (157 mg, 23.7 mmol), EDCI (6.04 g, 31.6 mmol), HOBt (2.13 g, 15.8 mmol) and triethylamine (8 g, 79 mmol) were sequentially added with stirring, which was stirred at room temperature overnight. EA/water (50 ml/50 mL) was added, stirred for 5 minutes and then separated. The aqueous phase was extracted with EA (50 ml×3). The organic phases were combined and washed with saturated brine (30 ml×3), dried and sampled, and purified by column chromatography (EA/PE=0%-100%) to obtain the target compound 11d (6.2 g, 15.05 mmol) as a colorless oil with a yield of 95%.

MS m/z (ESI): 412.0 $[M+H]^+$.

Step 4 3-amino-5-bromo-N-((4,6-dimethyl-2-oxo-1,2-dihydropyridin-3-yl) methyl)-6-fluoro-2-methylbenzamide 11e Compound 11d (5.7 g, 13.83 mmol) and $NH_4Cl$ (5.92 g, 110 mmol) were dissolved in a mixed solvent of ethanol/THF, $H_2O$ (100 ml/25 ml/2 ml). Under ice bath conditions, iron powder (6.16 g, 110 mmol) was added to the reaction solution in batches. After the addition was completed, the ice bath was removed, and the mixture was heated to 60° C. and stirred for 3 hours. The resultant was cooled to room temperature, filtered to remove the solids, and concentrated to remove the solvent. 50 ml of water was added, and extracted with EA (50 ml×3). The organic phases were combined and washed with saturated brine (50 ml×3), dried, concentrated and sampled, and purified by column chromatography (EA/PE=0%-100%) to obtain the target compound 11e (4.2 g, 11.05 mmol) as a pale yellow oil with a yield of 80%.

MS m/z (ESI): 382$[M+H]^+$.

Step 5 3-bromo-N-((4,6-dimethyl-2-oxo-1,2-dihydropyridin-3-yl)methyl)-2-fluoro-6-methyl-5-((tetrahydro-2H-pyran-4-yl)amino)benzamide 11f Compound 11e (2.4 g, 6.28 mmol) was dissolved in DCM (50 mL), and tetrahydro-4H-pyran-4-one (1.25 g, 12.56 mmol) and acetic acid (377 mg, 6.28 mmol) were added sequentially, which was stirred at room temperature for 1 h. Then sodium triacetoxyborohydride (5.3 g, 25.12 mmol) was added, and the mixture was stirred at room temperature overnight. 50 ml of water was added, stirred for 10 minutes, and separated. The organic phase was extracted with DCM (50 ml×2). The organic phases were combined, washed twice with saturated NaCl solution, dried over anhydrous sodium sulfate, concentrated and sampled, and purified by column chromatography (petroleum ether:ethyl acetate=0%-30%) to obtain the title compound 11f (2.4 g, 5.21 mmol) as a colorless oil, yield 83%.

MS m/z (ESI): 466 $[M+H]^+$.

Step 6 3-bromo-N-((4,6-dimethyl-2-oxo-1,2-dihydropyridin-3-yl)methyl)-5-(ethyl(tetrahydro-2H-pyran-4-yl)amino)-2-fluoro-6-methylbenzamide 11g Compound 11f (2.4 g, 5.21 mmol) was dissolved in DCM (30 mL), and acetaldehyde (0.917 g, 20.84 mmol) and acetic acid (312 mg, 5.21 mmol) were added sequentially under ice water bath, which was stirred at room temperature for 1 h. Then sodium triacetoxyborohydride (4.42 g, 20.84 mmol) was added, and the mixture was stirred at room temperature overnight. 30 ml of water was added, stirred for 10 minutes, and separated. The organic phase was extracted with DCM (50 ml×2). The organic phases were combined, washed twice with saturated NaCl solution, dried over anhydrous sodium sulfate, concentrated and sampled, and purified by column chromatography (petroleum ether:ethyl acetate=0%-30%) to obtain the title compound 11g (2.1 g, 4.25 mmol) as a white solid, yield 81.5%.

MS m/z (ESI): 494.1 $[M+H]^+$.

Step 7 N-((4,6-dimethyl-2-oxo-1,2-dihydropyridin-3-yl)methyl)-3-(ethyl (tetrahydro-2H-pyran-4-yl) amino)-6-fluoro-2-methyl-5-(1-morpholino-2,3-dihydro-1H-inden-5-yl)benzamide 11

Compound 11g (100 mg, 0.202 mmol) was dissolved in 3 ml of 1,4-dioxane, and compound 4h (67 mg, 0.202 mmol), $Pd(dppf)Cl_2$ (14.7 mg, 0.0202 mmol), potassium carbonate (56 mg, 0.404 mmol) and 1 ml of water were added in sequence, which was heated to 100° C. for 3 hours under nitrogen protection. After cooling to room temperature, 3 ml of water was added to dilute, which was extracted with EA (5 ml×3). The organic phases were combined, washed with saturated brine, dried and sampled, purified by column chromatography (methanol/dichloromethane=0%-10%) to obtain the title compound 11 (42 mg, 0.0681 mmol), white solid, yield 33.7%.

$^1H$ NMR (400 MHz, Methanol-d4) δ 7.42 (d, J=7.8 Hz, 1H), 7.35-7.27 (m, 2H), 7.23 (d, J=7.5 Hz, 1H), 6.08 (s, 1H), 4.48 (s, 2H), 4.31 (dd, J=7.7, 5.2 Hz, 1H), 3.88 (dd, J=11.1, 3.6 Hz, 2H), 3.67 (dt, J=6.3, 3.3 Hz, 4H), 3.33 (dd, J=11.7, 2.1 Hz, 2H), 3.10-2.94 (m, 4H), 2.85 (ddd, J=15.8, 8.6, 5.8 Hz, 1H), 2.60 (dt, J=9.7, 4.4 Hz, 2H), 2.50 (dt, J=11.4, 4.9 Hz, 2H), 2.35 (s, 3H), 2.29-2.08 (m, 8H), 1.72 (d, J=11.8 Hz, 2H), 1.55 (qd, J=11.5, 4.2 Hz, 2H), 0.86 (t, J=7.0 Hz, 31H).

MS m/z (ESI): 617.3 $[M+H]^+$.

Example 12 2-chloro-5-(ethyl(tetrahydro-2H-pyran-4-yl)amino)-N-((4-methoxy-6-methyl-2-carbonyl-1,2-dihydropyridin-3-yl)methyl)-6-methyl-3-(1-morpholino-2,3-dihydro-1H-inden-5-yl)benzamide

12

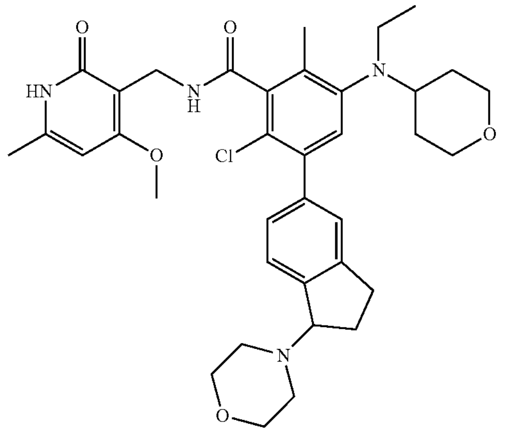

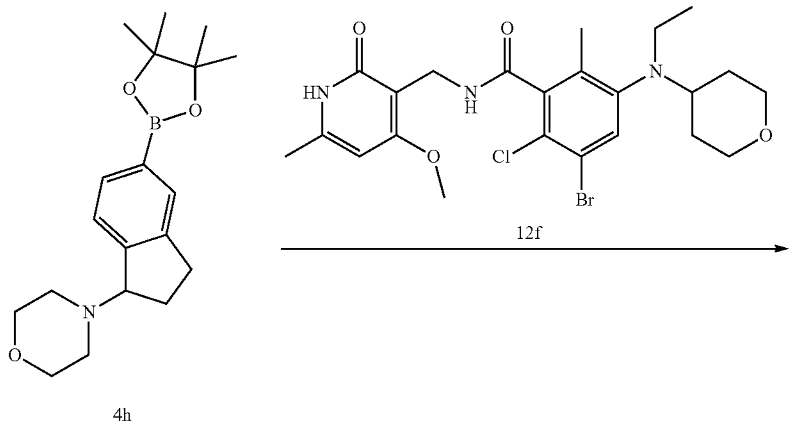

12f

4h

-continued

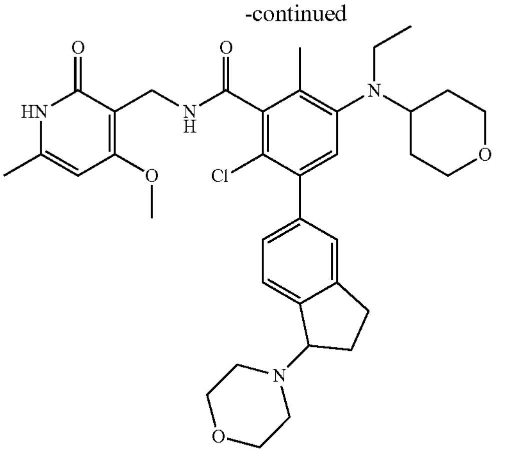

12

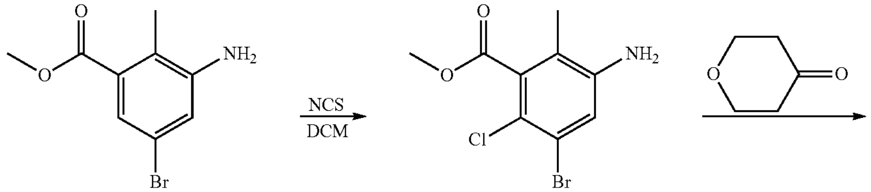

12a 12b

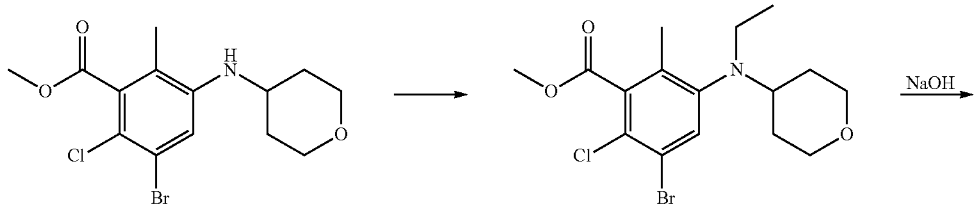

12c 12d

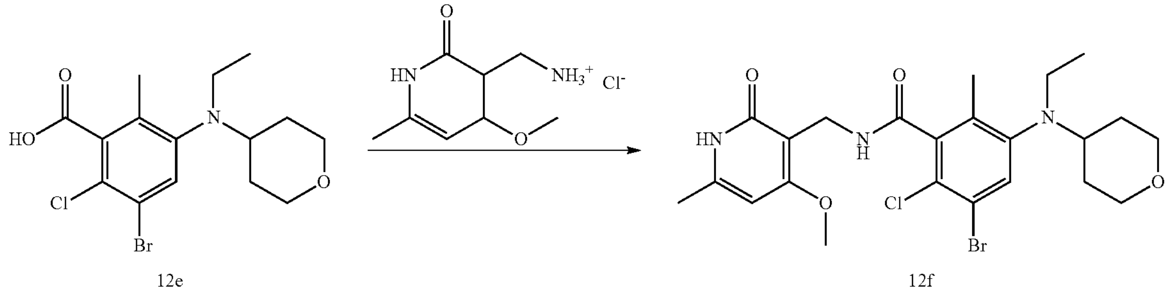

12e 12f

Step 1 methyl 3-amino-5-bromo-6-chloro-2-methylbenzoate 12b

In a 250 mL single-neck flask, compound 12a (6 g, 24.69 mmol) was added, and DCM (100 mL) was added to dissolve. Then NCS (3.3 g, 24.7 mmol) was added in batches, and the mixture was stirred at room temperature 25° C. for 2 h. TLC detection showed that the raw materials reacted completely and new spots were formed. The reaction solution was washed with water, extracted with DCM, and passed through a flash column to obtain the target compound 12b (3.6 g,) as a yellow oil with a yield of 52.6%.

Step 2 methyl 3-bromo-2-chloro-6-methyl-5-((tetra-hydro-2H-pyran-4-yl)amino) benzoate 12c In a 250 mL single-neck flask, compound 12b (3.6 g, 13.0 mmol) was added and dissolved in DCM (50 ml), and then compound tetrahydro-4H-pyran-4-one (2.6 g, 26.0 mmol) and acetic acid (2 mL) were added. After stirring for 30 min, $NaBH(AcO)_3$ (8.3 g, 39.0 mmol) was added, and the mixture was stirred at room temperature 25° C. for 2 h. It was detected that the raw materials was completely reacted and new spots were formed. The reaction solution was washed with water, washed with saturated $NaHCO_3$ solution, extracted with DCM, dried with anhydrous sodium sulfate, and evaporated to dryness to obtain a pale yellow oil as the target compound 12c (3.4 g), with a yield of 80%.

Step 3 methyl 3-bromo-2-chloro-5-(ethyl(tetra-hydro-2H-pyran-4-yl)amino)-6-methylbenzoate 12d In a 250 mL single-neck flask, compound 12c (3.4 g, 9.4 mmol) was added and dissolved in DCM (50 ml), and then acetaldehyde (4.2 g, 94 mmol) and acetic acid (2 mL) were added. After stirring for 30 min, $NaBH(AcO)_3$ (6.0 g, 28.3 mmol) was added, and the mixture was stirred at room temperature 25° C. for 2 h. It was detected that the raw materials was completely reacted and new spots were formed. The reaction solution was washed with water, washed with saturated $NaHCO_3$ solution, extracted with DCM, dried with anhydrous sodium sulfate, passed through a flash column, and evaporated to dryness to obtain a pale yellow solid as the target compound 12d (3.0 g), with a yield of 81.9%.

Step 4 3-bromo-2-chloro-5-(ethyl(tetrahydro-2H-pyran-4-yl)amino)-6-methylbenzoic Acid 12e In a 250 mL single-neck flask, compound 12d (3.0 mg, 7.69 mmol) was added, isopropanol (100 ml), water (5 ml), and NaOH (3 g, 76.9 mmol) were added in sequence, which was heated to 90° C. and refluxed for 8 hours. The reaction was detected to be complete. The reaction solution was evaporated to dryness. Water was added. The pH value was adjusted to neutral with dilute hydrochloric acid, and the aqueous phase was extracted with DCM three times. The organic phase was washed once with water, extracted with DCM, dried over anhydrous sodium sulfate, and concentrated to obtain a pale yellow solid, the target compound 12e (2 g), with a yield of 70%.

Step 5 3-bromo-2-chloro-5-(ethyl(tetrahydro-2H-pyran-4-yl)amino)-N-((4-methoxy-6-methyl-2-oxo-1,2-dihydropyridin-3-yl)methyl)-6-methylbenzamide 12f In a 50 mL single-neck flask, compound 12e (600 mg, 1.6 mmol), compound 3-(aminomethyl)-4-methoxy-6-picoline-2(1H)-one hydrochloride (450 mg, 2.4 mmol), EDCI (460 mg, 2.4 mmol), HOBT (324 mg, 2.4 mmol), DMF (15 ml), and DIPEA (800 mg, 8.0 mmol) were added. The reaction was refluxed at 50° C. for 3 h, and the reaction was detected to be complete. The reaction solution was concentrated, washed with water, extracted with DCM. The organic phase was dried over anhydrous $Na_2SO_4$, and passed through a flash column to obtain the target compound 12f (300 mg) as a yellow solid with a yield of 36.8%.

Step 6 2-chloro-5-(ethyl(tetrahydro-2H-pyran-4-yl)amino)-N-((4-methoxy-6-methyl-2-carbonyl-1,2-dihydropyridin-3-yl)methyl)-6-methyl-3-(1-morpholino-2,3-dihydro-1H-inden-5-yl)benzamide 12

Compound 4h (200 mg, 0.607 mol), $K_2CO_3$ (167 mg, 1.215 mmol), $Pd(dppf)Cl_2$ (44 mg, 0.0607 mmol), compound 12f (319 mg, 0.607 mmol) were dissolved in dioxane (15 mL), $H_2O$ (5 mL), which heated to 100° C. and stirred for 6 h under the protection of argon. After the reaction was completed, the reaction solution was extracted with water and ethyl acetate, and the organic phase was washed with saturated brine, dried over anhydrous sodium sulfate, filtered, concentrated and purified by column chromatography to obtain the title compound 74 (36 mg, 0.055 mmol) with a yield of 9.1%.

$^1H$ NMR (400 MHz, Methanol-d4) δ 7.40 (d, J=7.8 Hz, 1H), 7.22-7.13 (m, 2H), 7.10 (s, 1H), 6.25-6.19 (m, 1H), 4.45 (s, 2H), 4.31 (dd, J=7.7, 5.3 Hz, 1H), 3.89 (s, 5H), 3.68 (dt, J=6.5, 3.4 Hz, 4H), 3.41-3.30 (m, 2H), 3.11-2.93 (m, 4H), 2.86 (d, J=6.3 Hz, 1H), 1.59 (q, J=5.5, 4.4 Hz, 2H), 2.56-2.47 (m, 2H), 2.34-2.07 (m, 8H), 1.71 (d, J=12.8 Hz, 2H), 1.59 (dd, J=12.5, 4.1 Hz, 2H), 0.86 (t, J=7.0 Hz, 3H).

MS m/z (ESI): 649.2 $[M+1]^+$.

Example 13 N-((4,6-dimethyl-2-oxo-1,2-dihydro-pyridin-3-yl)methyl)-3-((2,6-dimethyltetrahydro-2H-pyran-4-yl)(ethyl)amino)-2-methyl-5-(1-morpholino-2,3-di hydro-1H-inden-5-yl)benzamide

13

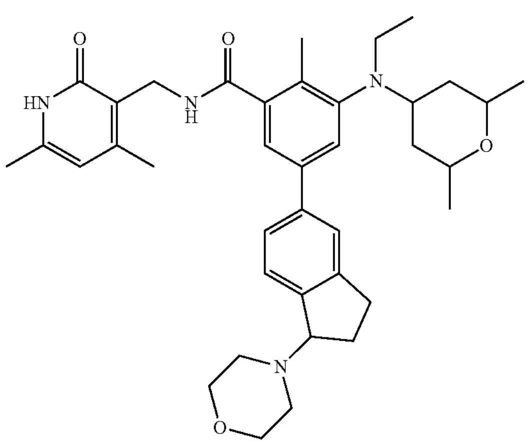

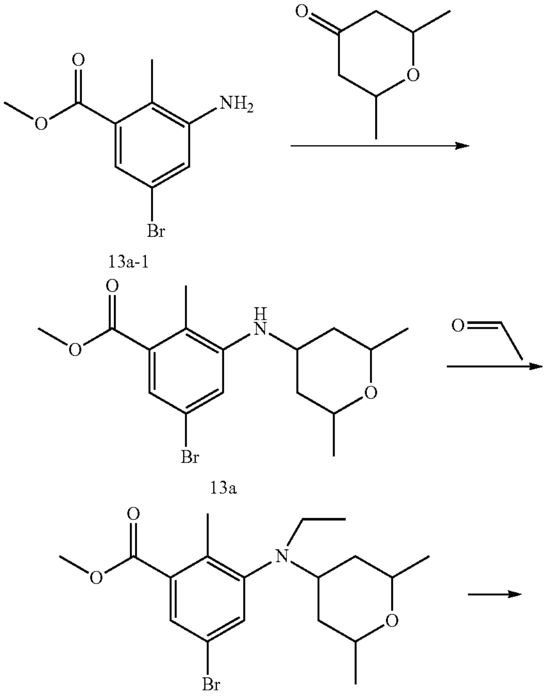

13a-1

13a

13b

-continued

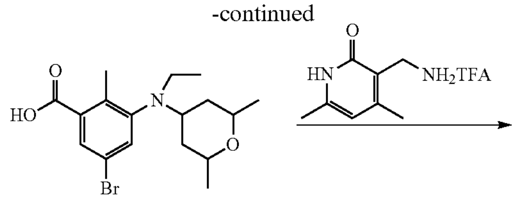

13c

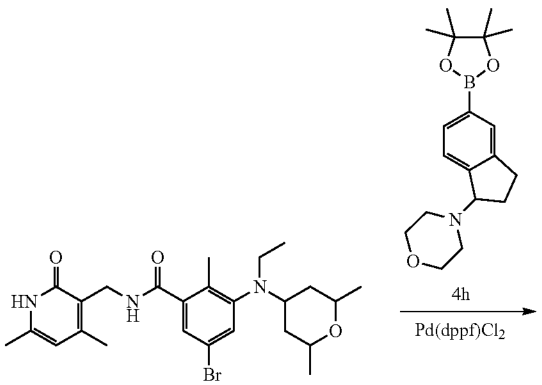

13d

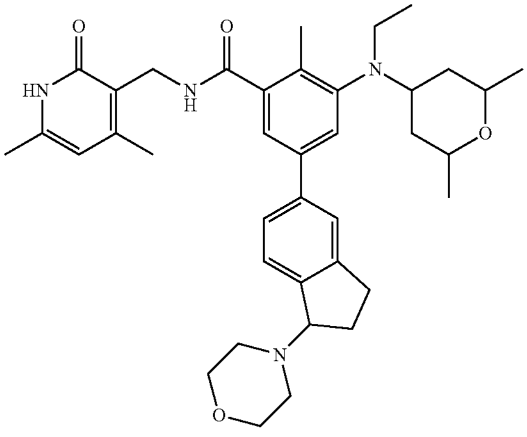

13

Step 1 methyl 5-bromo-3-((2,6-dimethyltetrahydro-2H-pyran-4-yl)amino)-2-methylbenzoate 13

Compound methyl 3-amino-5-bromo-2-methylbenzoate 13a-1 (3 g, 12.4 mmol) and compound 2,6-dimethyl-4H-pyran-4-one (3.1 g, 24.8 mmol) were dissolved in dichloromethane (30 m g), and sodium triacetoxyborohydride (7.9 g, 37.2 mmol) was added, which was stirred at room temperature for 5 h. Water was added, which was extracted with dichloromethane three times. The organic phases were dried with anhydrous sodium sulfate, and concentrated to obtain the title compound 13a (4 g, 11.2 mmol) with a yield of 900.

Step 2 methyl 5-bromo-3-((2,6-dimethyltetrahydro-2H-pyran-4-yl)(ethyl) amino)-2-methylbenzoate 13b A solution of compound 13a (4 g, 11.2 mmol) was added to dichloromethane (3 mL), and acetaldehyde (12 g, 272 mmol), sodium triacetoxyborohydride (15 g, 72.3 mmol), and acetic acid (3 mL) were added, which was stirred at room temperature for 16 h. After the reaction was completed, water was added, and extracted with dichloromethane. The organic phase was washed with sodium bicarbonate solution 3 times, and purified by column chromatography to obtain the title compound 13b (1.8 g, 4.7 mmol) with a yield of 41%.

Step 3 5-bromo-3-((2,6-dimethyltetrahydro-2H-pyran-4-yl)(ethyl)amino)-2-methylbenzoic Acid 13c Compound 13b (1.8 g, 4.7 mmol) was dissolved in methanol:tetrahydrofuran (v/v=2:1, 15 mL), and 20 mL of water, and sodium hydroxide (0.58 g, 14.5 mmol) were added, which was stirred at room temperature for 14 h, and spin-dried, adjusted to pH 5-6 with dilute hydrochloric acid solution, extracted 3 times with ethyl acetate. The organic phases were concentrated to obtain a yellow oily substance as the title compound 13c (1.4 g, 3.8 mmol), yield 80%.

Step 4 5-bromo-N-((4,6-dimethyl-2-oxo-1,2-dihydropyridin-3-yl)methyl)-3-((2,6-dimethyltetrahydro-2H-pyran-4-yl)(ethyl)amino)-2-methylbenzamide 13d Compound 13c (150 mg, 0.405 mmol) and compound 3-(aminomethyl)-4,6-lutidine-2(1H)-one trifluoroacetate (107 mg, 0.405 mmol) were dissolved in DMF (20 mL), and HATU (308 mg, 0.81 mmol), HOBT (65 mg, 0.485 mmol) and triethylamine (2 mL) were added, which was stirred at room temperature for 14 hours. Water was added, which was extracted with ethyl acetate three times. The organic phase was washed three times with NaCl solution, and purified by column chromatography to obtain the title compound 13d (80 mg, 0.159 mmol) with a yield of 39%.

Step 5 N-((4,6-dimethyl-2-oxo-1,2-dihydropyridin-3-yl)methyl)-3-((2,6-dimethyltetrahydro-2H-pyran-4-yl)(ethyl)amino)-2-methyl-5-(1-morpholino-2,3-dihydro-1H-inden-5-yl)benzamide 13

Compound 13d (80 mg, 0.159 mmol) and compound 4h (52.2 mg, 0.159 mmol) were dissolved in 1,4-dioxane:water (v/v=3:1, 20 mL), and [1,1'-bis(diphenylphosphino)ferrocene]palladium dichloride (11.6 mg, 0.0159 mmol) and potassium carbonate (43.8 mg, 0.318 mmol) were added, which was heated to 100° C. under the protection of argon and stirred for 2 h. After cooling, the resultant was spin-dried and extracted 3 times with ethyl acetate. The organic phase was dried over anhydrous sodium sulfate, concentrated and purified by column chromatography to obtain the title compound 13 (14 mg, yield 14.1%).

$^1$H NMR (400 MHz, Methanol-d4) δ 7.95 (s, 1H), 7.71 (d, J=28.1 Hz, 3H), 7.39 (d, J=37.8 Hz, 1H), 6.12 (s, 1H), 5.05-4.91 (m, 2H), 4.49 (s, 2H), 4.03 (d, J=12.9 Hz, 3H), 3.80 (d, J=13.9 Hz, 3H), 3.58 (q, J=7.0 Hz, 1H), 3.57-3.33 (m, 3H), 3.16 (d, J=27.7 Hz, 4H), 2.58 (s, 2H), 2.45 (d, J=13.0 Hz, 2H), 2.37 (s, 3H), 2.28-2.14 (m, 3H), 1.27 (d, J=3.7 Hz, 4H), 1.25-1.09 (m, 5H), 1.02 (s, 2H), 0.87 (d, J=8.2 Hz, 3H).

MS m/z (ESI): 627.5 $[M+H]^+$.

Example 14 N-((4,6-dimethyl-2-oxo-1,2-dihydropyridin-3-yl)methyl)-3-((2-methyltetrahydro-2H-pyran-4-yl)(ethyl)amino)-2-methyl-5-(1-morpholino-2,3-dihydro-1H-inden-5-yl)benzamide

14

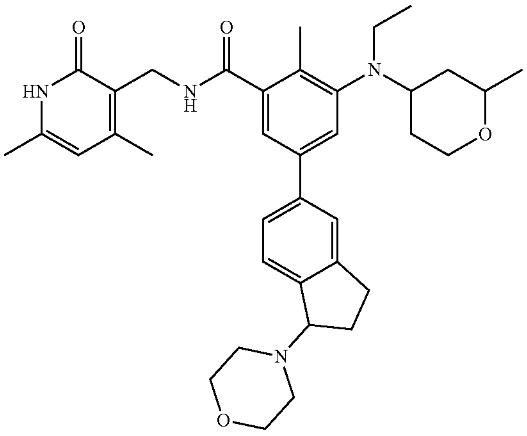

Using a synthesis method similar to that in Example 13, replacing 2,6-dimethyltetrahydro-4H-pyran-4-one with 2-methyltetrahydro-4H-pyran-4-one, the title product 14 was obtained with a yield of 20%.

$^1$H NMR (400 MHz, Methanol-d4) δ 7.46-7.35 (m, 4H), 7.28 (t, J=1.8 Hz, 1H), 6.09 (s, 1H), 4.46 (s, 2H), 4.36-4.30 (m, 1H), 3.90 (s, 1H), 3.77 (s, 1H), 3.68 (d, J=2.8 Hz, 4H), 3.38 (d, J=11.7 Hz, 1H), 3.12 (d, J=7.0 Hz, 1H), 3.09 (s, 2H), 3.02 (dd, J=14.8, 7.2 Hz, 2H), 2.91-2.84 (m, 1H), 2.63 (q, J=5.5, 4.4 Hz, 2H), 2.54 (d, J=11.6 Hz, 2H), 2.41-2.26 (m, 6H), 2.22 (s, 3H), 2.19-2.13 (m, 1H), 1.78 (d, J=12.7 Hz, 1H), 1.71 (d, J=12.2 Hz, 1H), 1.54 (d, J=15.0 Hz, 1H), 1.42 (s, 1H), 1.27 (d, J=5.2 Hz, 1H), 1.07 (dd, J=27.4, 6.1 Hz, 3H), 0.90-0.83 (m, 3H).

MS m/z (ESI): 613.6 [M+H]$^+$.

Example 15 N-4,6-((dimethyl-2-oxo-1,2-dihydropyridin-3-yl)methyl)-3-(ethyl (tetrahydro-2H-pyran-4-yl)amino)-5-(5-isoindolin-2-yl)-2-methylbenzamide

15

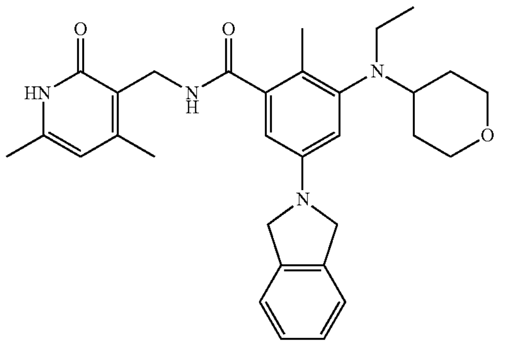

-continued

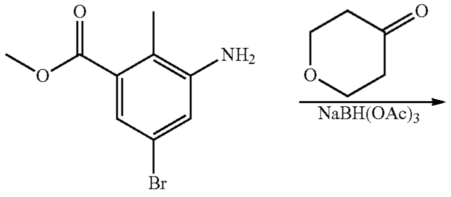

15a

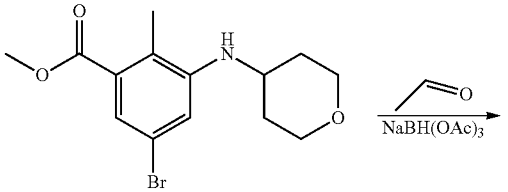

15b

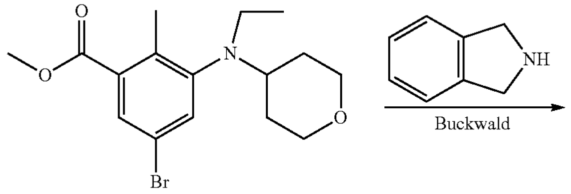

15c

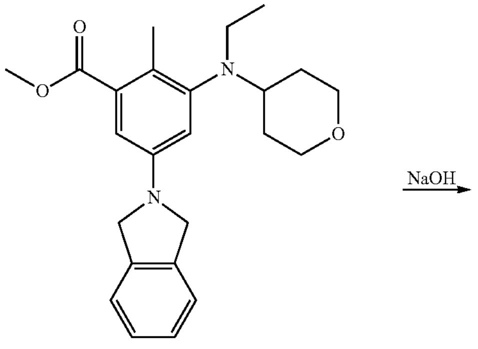

15d

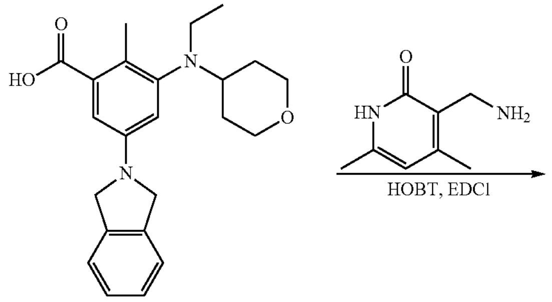

15e

-continued

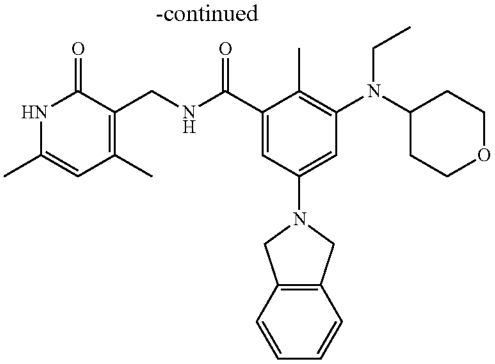

15

Step 1 methyl 5-bromo-2-methyl-3-((tetrahydro-2H-pyran-4-yl)amino)benzoate 15b Compound 15a (2.3 g, 9.4 mmol) was dissolved in 1,2-dichloroethane (5.0 mL), and acetic acid (2.83 g, 47.2 mmol) and tetrahydropyrone (1.4 g, 14.2 mmol) were added. After the reaction was stirred at room temperature for 30 minutes, sodium triacetoxyborohydride (3.0 g, 14.2 mmol) was added, which stirred at room temperature for 15 h. After the reaction is completed, the reaction solution was quenched with water, which was extracted with dichloromethane three times. The organic phases were washed with saturated brine, dried over anhydrous sodium sulfate, filtered, concentrated and purified by column chromatography to obtain the title compound 15b (2.6 g, 7.9 mmol) with a yield of 84%.

Step 2 methyl 5-bromo-3-(ethyl(tetrahydro-2H-pyran-4-yl)amino)-2-methylbenzoate 15c Compound 15b (2.0 g, 6.1 mmol) was dissolved in 1,2-dichloroethane (5.0 mL), and acetic acid (2.2 g, 36.7 mmol) and acetaldehyde (0.7 ml, 12.2 mmol) were added. After the reaction was stirred at room temperature for 30 minutes, sodium triacetoxyborohydride (3.9 g, 18.4 mmol) was added, which was stirred at room temperature for 3 h. After the reaction was completed, the reaction solution was quenched with water, which was extracted with dichloromethane three times. The organic phases were washed with saturated brine, dried over anhydrous sodium sulfate, filtered, concentrated and purified by column chromatography to obtain the title compound 15c (2.0 g, 5.62 mmol) with a yield of 92%.

Step 3 methyl 3-(ethyl(tetrahydro-2H-pyran-4-yl)amino)-5-(isoindolin-2-yl)-2-methylbenzoate 15d Compound 15c (200 mg, 0.56 mmol) and 2,3-dihydroisoindole hydrochloride (173 mg, 1.12 mmol) were dissolved in toluene (5.0 mL), and anhydrous cesium carbonate (368 mg, 1.12 mmol), tris(dibenzylideneacetone)dipalladium (102 mg, 0.112 mmol), and 4,5-bisdiphenylphosphine-9,9-dimethylxanthene (65 mg, 0.112 mmol) were added, which was stirred at 110° C. for 6 h under the protection of nitrogen. After cooling, the reaction solution was spin-dried and extracted with dichloromethane three times, and the organic phases were washed with saturated brine, dried over anhydrous sodium sulfate, filtered, concentrated and purified by column chromatography to obtain the title compound 15d (60 mg, 0.15 mmol) with a yield of 27%.

Step 4 3-(ethyl(tetrahydro-2H-pyran-4-yl)amino)-5-(isoindolin-2-yl)-2-methylbenzoic Acid 15e Compound 15d (60 mg, 0.15 mmol) was dissolved in tetrahydrofuran (4.0 mL), and sodium hydroxide (61 mg, 1.5 mmol) and water (1.0 mL) were added, which was heated to 50° C. and stirred for 2 h. After the reaction was completed, the reaction solution was neutralized with hydrochloric acid to pH=6-7, which was extracted with dichloromethane three times. The organic phases were washed with saturated brine, dried over anhydrous sodium sulfate, filtered, concentrated and purified by column chromatography to obtain the title compound 15e (40 mg, 0.11 mmol) with a yield of 67%.

Step 5 N-4,6-((dimethyl-2-oxo-1,2-dihydropyridin-3-yl)methyl)-3-(ethyl (tetrahydro-2H-pyran-4-yl) amino)-5-(5-isoindolin-2-yl)-2-methylbenzamide 15

Compound 15e (40 mg, 0.11 mmol) and 3-(aminomethyl)-4,6-dimethyl-1H-pyridin-2-one hydrochloride (24 mg, 0.13 mmol) were dissolved in N,N-dimethyl formamide (2.0 mL), and 1-(3-dimethylaminopropyl)-3-ethylcarbodiimide hydrochloride (40 mg, 0.21 mmol), 1-hydroxybenzotriazole (14 mg, 0.10 mmol) and triethylamine (32 mg, 0.3 mmol) were added, which was heated to 50° C. and stirred for 4 h. After the reaction was completed, the reaction solution was washed with water, which was extracted with dichloromethane three times. The organic phases were washed with saturated brine, dried over anhydrous sodium sulfate, filtered, concentrated and purified by column chromatography to obtain the title compound 15 (5.0 mg, 0.010 mmol) with a yield of 7.4%.

$^1$H NMR (400 MHz, DMSO) δ 7.98 (s, 1H), 7.39 (m, 2H), 7.30 (m, 2H), 6.48 (s, 1H), 6.34 (s, 1H), 5.87 (s, 1H), 4.56 (s, 4H), 4.29-4.28 (d, J=4.8 Hz, 2H), 3.85-3.82 (d, J=10.8 Hz, 2H), 3.24 (m, 2H), 3.05 (q, J=6.8 Hz, 2H), 2.96 (m, 11H), 2.21 (s, 3H), 2.10 (s, 6H), 1.69-1.66 (d, J=12.8 Hz, 2H), 1.53 (m, 2H), 0.85-0.82 (t, J=6.8 Hz, 3H).

MS m/z (ESI): 515 $[M+H]^+$.

Example 16 5-(3,4-dihydroisoquinoline-2(1H)-yl)-N-((4,6-dimethyl-2-oxo-1,2-dihydropyridin-3-yl) methyl)-3-(ethyl(tetrahydro-2H-pyran-4-yl)amino)-2-methylbenzamide

16

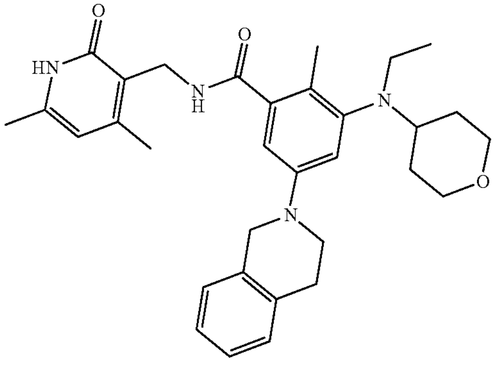

Using a synthesis method similar to that in Example 15, replacing 2,3-dihydroisoindole hydrochloride with 1,2,3,4-tetrahydroisoquinoline, the title product 16 was obtained with a yield of 35%.

$^1$H NMR (400 MHz, DMSO-d6) δ 11.47 (s, 1H), 7.98 (s, 1H), 7.26-7.01 (m, 4H), 6.77 (d, J=2.5 Hz, 1H), 6.58 (d, J=2.4 Hz, 1H), 5.83 (s, 1H), 4.33-4.16 (m, 4H), 3.77 (d, J=11.2 Hz, 2H), 3.43 (t, J=5.9 Hz, 2H), 3.18 (t, J=11.3 Hz, 2H), 3.03-2.79 (m, 5H), 2.21-1.98 (m, 8H), 1.58 (d, J=12.4 Hz, 2H), 1.44 (d, J=12.2 Hz, 2H), 0.75 (t, J=6.9 Hz, 3H),

MS m/z (ESI): 529 [M+H]$^+$.

Example 17 N-((4,6-dimethyl-2-oxo-1,2-dihydropyridin-3-yl)methyl)-5-(5-(dimethylamino)isoindolin-2-yl)-3-(ethyl(tetrahydro-2H-pyran-4-yl)amino)-2-methylbenzamide

17

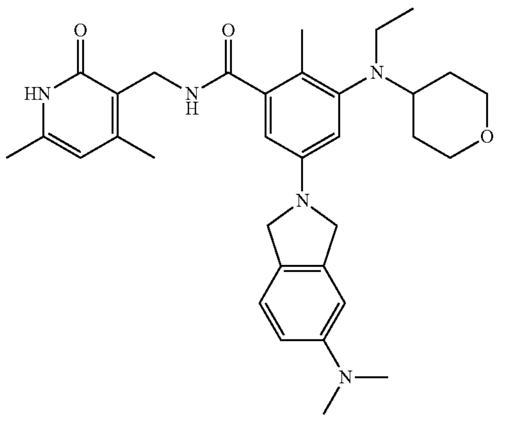

Using a synthesis method similar to that in Example 15, replacing 2,3-dihydroisoindole hydrochloride with N,N-dimethyl-2,3-dihydroisoindole-5-amine hydrochloride, the title product 17 was obtained with a yield of 9%.

MS m/z (ESI): 558.3 [M+H]$^+$.

Example 18 N-((4,6-dimethyl-2-oxo-1,2-dihydropyridin-3-yl)methyl)-3-(ethyl (tetrahydro-2H-pyran-4-yl)amino)-2-methyl-5-(5-morpholinoisoindolin-2-yl) benzamide

18

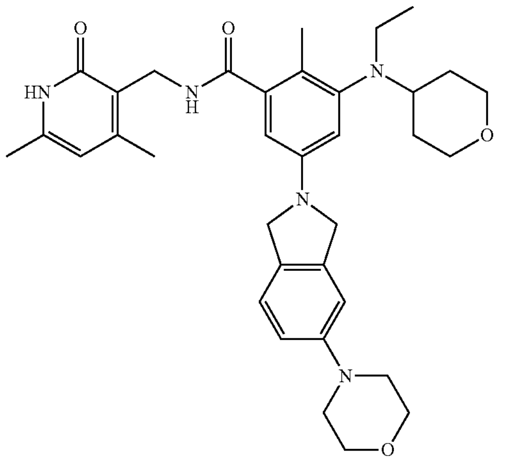

Using a synthesis method similar to that in Example 15, replacing 2,3-dihydroisoindole hydrochloride with 4-(isoindol-5-yl)morpholine, the title product 18 was obtained with a yield of 33%.

MS m/z (ESI): 600 [M+H]$^+$.

Example 19 5-(5-acrylamidoisoindolin-2-yl)-N-((4,6-dimethyl-2-oxo-1,2-dihydropyridin-3-yl)methyl)-3-(ethyl(tetrahydro-2H-pyran-4-yl)amino)-2-methylbenzamide

19

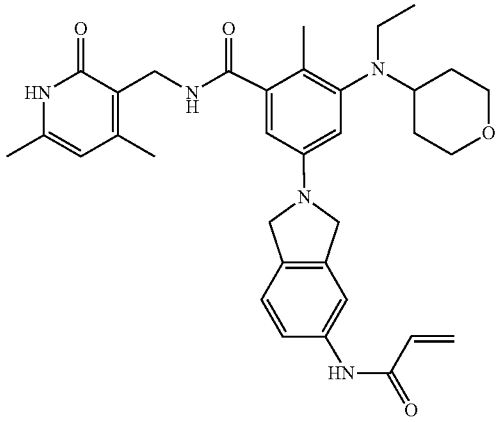

Using a synthesis method similar to that in Example 15, replacing 2,3-dihydroisoindole hydrochloride with N-(isoindolin-5-yl)acrylamide, the title product 19 was obtained with a yield of 14%.

MS m/z (ESI): 584.3 [M+H]$^+$.

Example 20 N-((4,6-dimethyl-2-oxo-1,2-dihydropyridin-3-yl)methyl)-3-(ethyl (tetrahydro-2H-pyran-4-yl)amino)-2-methyl-5-((5-morpholinomethyl) isoindolin-2-yl)benzamide

20

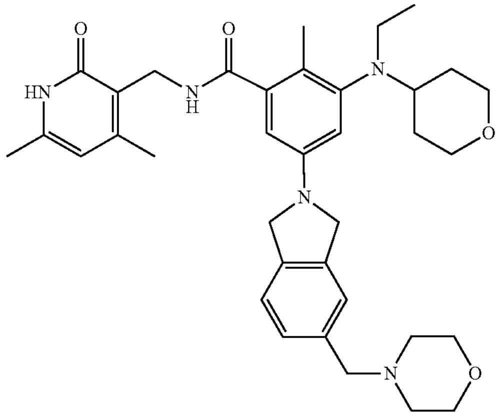

Using a synthesis method similar to that in Example 15, replacing 2,3-dihydroisoindole hydrochloride with 4-(isoindol-5-ylmethyl)morpholine, the title product 20 was obtained with a yield of 28%.

MS m/z (ESI): 614.3 [M+H]$^+$.

Example 21 N-((4,6-dimethyl-2-oxo-1,2-dihydropyridin-3-yl)methyl)-3-(ethyl (tetrahydro-2H-pyran-4-yl)amino)-2-methyl-5-(5-methyl-3,5-dihydropyrrolo[3,4-c]pyrrole-2(1H)-yl)benzamide

21

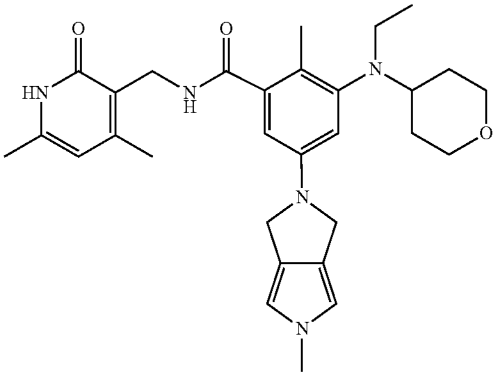

Using a synthesis method similar to that in Example 15, replacing 2,3-dihydroisoindole hydrochloride with 5-methyl-1,2,3,5-tetrahydropyrrolo[3,4-c]pyrrole, the title product 21 was obtained with a yield of 11%.

MS m/z (ESI): 518.3 $[M+H]^+$.

Example 22 N-((4,6-dimethyl-2-oxo-1,2-dihydropyridin-3-yl)methyl)-3-(ethyl (tetrahydro-2H-pyran-4-yl)amino)-5-(5-(ethyl(tetrahydro-2H-pyran-4-yl) amino) isoindolin-2-yl)-2-methylbenzamide

22

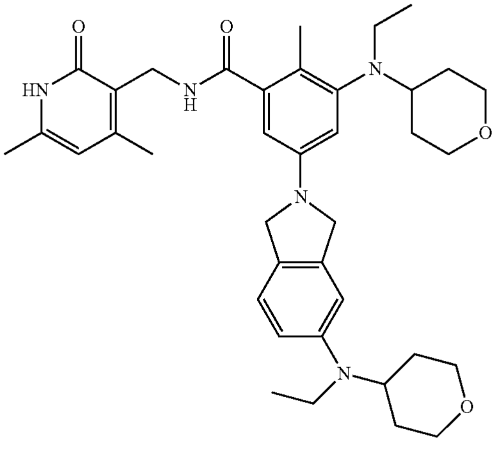

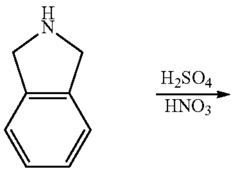

22a

-continued

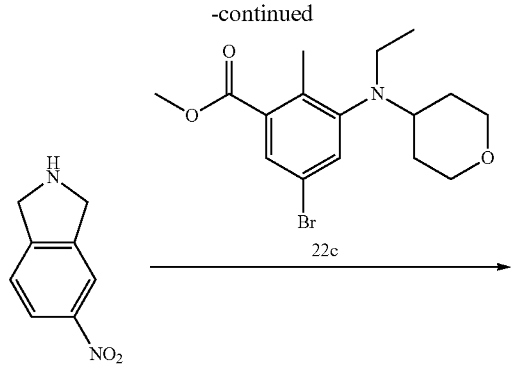

22b

22c

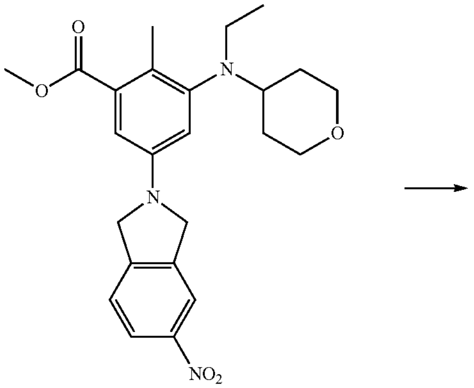

22d

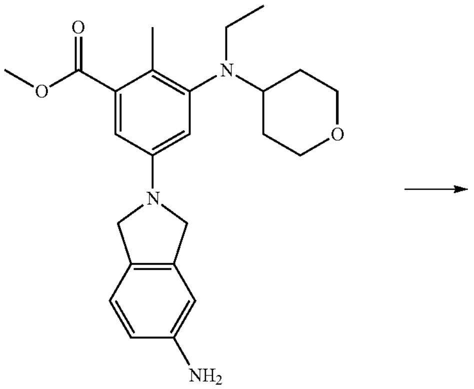

22e

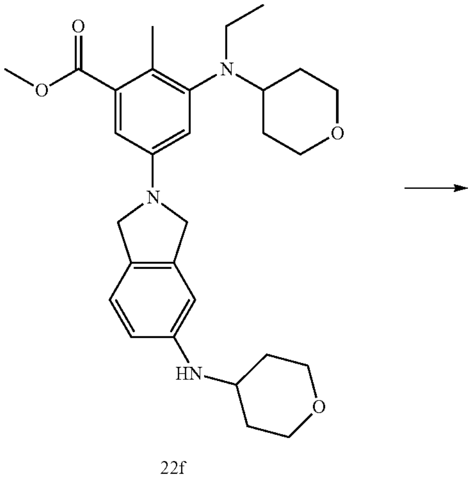

22f

-continued

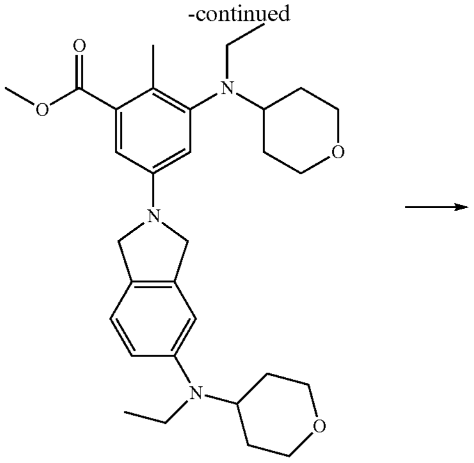

22g

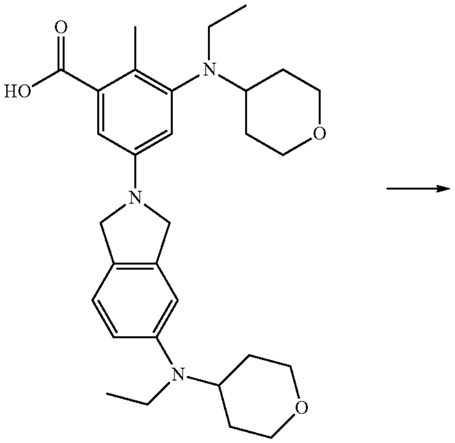

22h

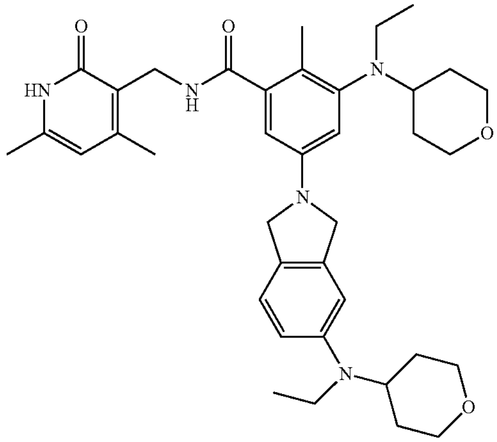

22

Step 1: Nitroisoindoline 22b

Compound 22a (isoindoline) (8.0 g, 51.3 mmol) was dissolved in concentrated sulfuric acid (30 mL), and fuming nitric acid (8.0 ml) was slowly added dropwise under ice bath conditions, which stirred at this temperature for 1 hour. The reaction solution was slowly added to ice water with stirring, filtered and dried to obtain a white solid, namely the title compound 145b (7 g, 42.68 mmol), with a yield of 84%.

MS m/z (ESI): 165[M+1]$^+$.

Step 2 methyl 3-(ethyl(tetrahydro-2H-pyran-4-yl) amino)-2-methyl-5-(5-nitroisoindolin-2-yl)-benzoate 22d In a 100 mL single-neck flask, compound 22b (5.0 g, 30.49 mmol), compound 22c (5.41 g, 15.24 mmol), $Pd_2(dba)_3$ (2.8 g, 3.05 mmol), Xant-phose (1.77 g, 3.05 mmol), potassium tert-butoxide (13.7 g, 122 mmol), and toluene (50 mL) were added under the protection of $N_2$, which was heated to 135° C. and stirred for 1 h. TLC detection showed that the raw material was completely reacted. The reaction solution was extracted with EA, and the organic phase was washed with water, dried with anhydrous sodium sulfate, spin-dried, and purified by flash column (PE:EA=8:1). A light yellow oil was obtained, the target compound 22d (400 mg, 0.911 mmol), yield 3.0%.

MS m/z (ESI): 440[M+1]$^+$.

Step 3 methyl 5-(5-aminoisoindolin-2-yl)-3-(ethyl (tetrahydro-2H-pyran-4-yl) amino)-2-methylbenzoate 22e Compound 22d (400 mg, 0.911 mmol), MeOH (10 mL) and Pd/C (400 mg) were added to a 50 mL single-necked flask. The reaction solution was stirred at room temperature overnight under the protection of $H_2$. TLC detection showed that the raw material was completely reacted and a new point was formed. The reaction solution was filtered, and the filtrate was spin-dried to obtain the target compound 22e (240 mg, 0.59 mmol) as a pale yellow oil with a yield of 64.4%.

MS m/z (ESI): 410[M+1]$^+$.

Step 4 methyl 3-(ethyl(tetrahydro-2H-pyran-4-yl) amino)-2-methyl-5-(5-((tetrahydro-2H-pyran-4-yl) amino)isoindolin-2-yl)benzoate 22f Compound 22e (120 mg, 0.293 mmol) was dissolved in dichloroethane (8.0 mL), and acetic acid (106 mg, 1.76 mmol) and tetrahydropyrone (57 g, 0.587 mmol) were added. After the reaction was stirred at room temperature for 30 minutes, sodium triacetoxyborohydride (186 mg, 0.88 mmol) was added, which was stirred overnight at room temperature. After the reaction was completed, the reaction solution was quenched with water, which was extracted with dichloromethane three times. The organic phases were washed with saturated brine, dried over anhydrous sodium sulfate, filtered, concentrated and purified by column chromatography to obtain the title compound 22f (110 mg, 0.223 mmol) with a yield of 76%. MS m/z (ESI): 494[M+1]$^+$.

Step 5 methyl 5-bromo-3-(ethyl(tetrahydro-2H-pyran-4-yl)amino)-2-methylbenzoate 22g Compound 22f (50 mg, 0.101 mmol) was dissolved in dichloroethane (5.0 mL), and acetic acid (37 mg, 0.606 mmol) and acetaldehyde (22 ml, 0.506 mmol) were added. After the reaction was stirred at room temperature for 30 minutes, sodium triacetoxyborohydride (64 mg, 0.303 mmol) was added, which was stirred at room temperature for 2 h. After the reaction was completed, the reaction solution was quenched with water, which was extracted with dichloromethane three times. The organic phases were washed with saturated brine, dried over anhydrous sodium sulfate, filtered, concentrated and purified by column chromatography to obtain the title compound 22g (40 mg, 0.077 mmol) with a yield of 76%.

MS m/z (ESI): 522[M+1]$^+$.

Step 6 3-(ethyl(tetrahydro-2H-pyran-4-yl)amino)-5-(5-(ethyl(tetrahydro-2H-pyran-4-yl)amino)isoindolin-2-yl)-2-methylbenzoic acid 22h Compound 22g (40 mg, 0.077 mmol) was dissolved in tetrahydrofuran (2.0 mL), and sodium hydroxide (18 mg, 0.77 mmol) and water (0.5 mL) were added. After the reaction solution was heated to 50° C. and stirred for 2 h, the reaction was completed. The reaction solution was neutralized with hydrochloric acid to pH=5-6, extracted with dichloromethane three times. The organic phases were washed with saturated brine, dried over anhydrous sodium sulfate, filtered, concentrated and purified by column chromatography to obtain the title compound 22h (35 mg, 0.07 mmol) with a yield of 88%.

Step 7 N-((4,6-dimethyl-2-oxo-1,2-dihydropyridin-3-yl)methyl)-3-(ethyl (tetrahydro-2H-pyran-4-yl) amino)-5-(5-(ethyl(tetrahydro-2H-pyran-4-yl)amino) isoindolin-2-yl)-2-methylbenzamide 22

Compound 22h (35 mg, 0.07 mmol) and 3-(aminomethyl)-4,6-dimethyl-1H-pyridin-2-one hydrochloride (20 mg, 0.104 mmol) were dissolved in N,N-dimethylformamide (2.0 mL), and 1-(3-dimethylaminopropyl)-3-ethylcarbodiimide hydrochloride (26 mg, 0.138 mmol), 1-hydroxybenzotriazole (10 mg, 0.069 mmol) and triethylamine (35 mg, 0.345 mmol) were added. The reaction solution was left overnight at room temperature, and the reaction was completed. The reaction solution was washed with water, which was extracted with dichloromethane three times. The organic phases were washed with saturated brine, dried over anhydrous sodium sulfate, filtered, concentrated and purified by column chromatography to obtain the title compound 22 (9.0 mg, 0.014 mmol) with a yield of 20.3%.

1H NMR (400 MHz, DMSO-d6) δ 11.44 (s, 1H), 7.93 (t, J=5.1 Hz, 1H), 7.13 (d, J=8.4 Hz, 1H), 6.82-6.75 (m, 1H), 6.69 (dd, J=8.5, 2.3 Hz, 1H), 6.41 (d, J=2.4 Hz, 1H), 6.27 (d, J=2.4 Hz, 1H), 5.83 (s, 1H), 4.45 (s, 2H), 4.39 (s, 2H), 4.25 (d, J=5.1 Hz, 2H), 3.89 (d, J=10.9 Hz, 2H), 3.80 (d, J=11.9 Hz, 3H), 3.40 (td, J=11.1, 4.1 Hz, 2H), 3.21 (dd, J=14.1, 9.2 Hz, 4H), 3.00 (q, J=6.9 Hz, 2H), 2.92 (s, 1H), 2.18 (s, 3H), 2.10-2.05 On, 6H), 1.68-1.60 (m, 5H), 1.47 (dd, J=14.9, 11.1 Hz, 2H), 1.20 (s, 1H), 1.05 (t, J=6.9 Hz, 3H), 0.81 (t, J=6.9 Hz, 3H).

MS ma/z (ESI): 642.3 [M+H]$^+$.

Example 23 N-((4,6-dimethyl-2-oxo-1,2-dihydropyridin-3-yl)methyl)-3-(ethyl (tetrahydro-2H-pyran-4-yl)amino)-5-(5-(ethyl(tetrahydro-2H-pyran-4-yl) amino) isoindolin-2-yl)-2-methylbenzamide 23

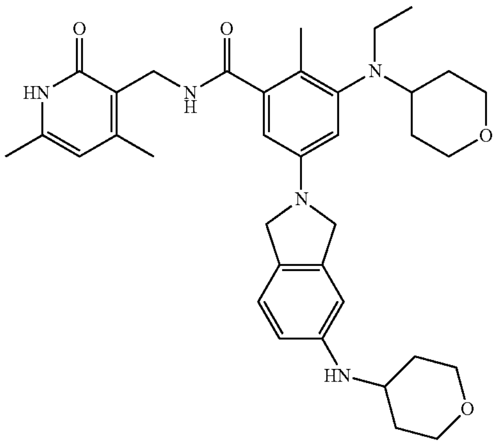

23

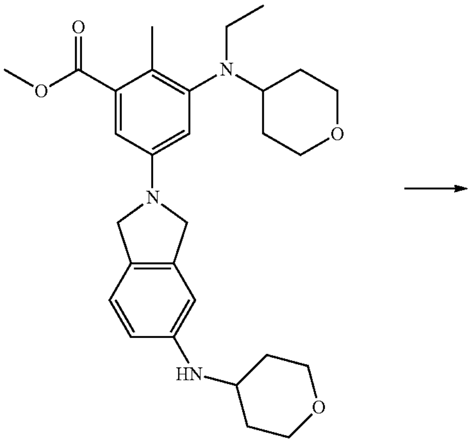

22f

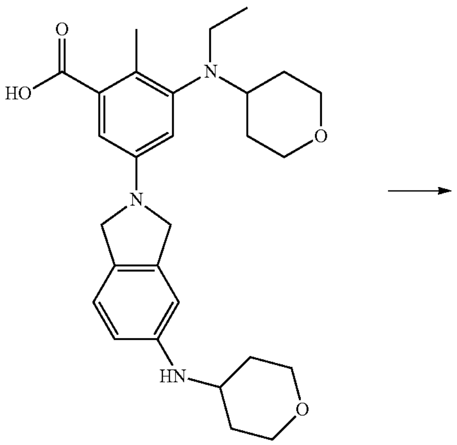

23a

-continued

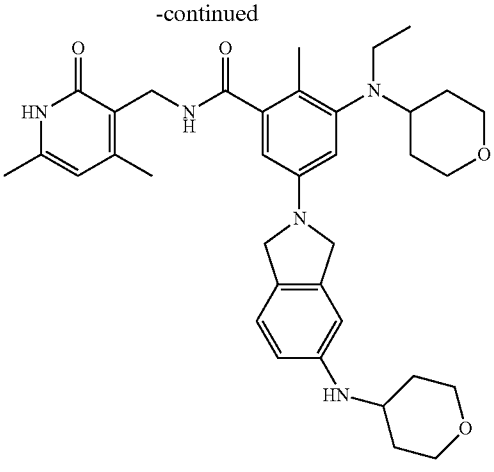

23

Step 1 3-(ethyl(tetrahydro-2H-pyran-4-yl)amino)-2-methyl-5-(5-((tetrahydro-2H-pyran-4-yl)amino) isoindolin-2-yl)benzoic Acid 23a Compound 22f (60 mg, 0.122 mmol) was dissolved in tetrahydrofuran (2.0 mL), and lithium hydroxide (30 mg, 0.122 mmol) and water (0.5 mL) were added. After the reaction solution was heated to 50° C. and stirred for 2 h, the reaction was completed. The reaction solution was neutralized with hydrochloric acid to pH=5-6, which was extracted with dichloromethane three times. The organic phases were washed with saturated brine, dried over anhydrous sodium sulfate, filtered, concentrated and purified by column chromatography to obtain the title compound 23a (50 mg, 0.104 mmol) with a yield of 85.7%.

MS m/z (ESI): 480 $[M+1]^+$.

Step 2 N-((4,6-dimethyl-2-oxo-1,2-dihydropyridin-3-yl)methyl)-3-(ethyl (tetrahydro-2H-pyran-4-yl) amino)-2-methyl-5-((tetrahydro-2H-pyran-4-yl) amino)isoindolin-2-yl)benzamide 23

Compound 23a (50 mg, 0.104 mmol) and 3-(aminomethyl)-4,6-dimethyl-1H-pyridin-2-one hydrochloride (30 mg, 0.156 mmol) were dissolved in N,N-dimethylformamide (2.0 mL), and 1-(3-dimethylaminopropyl)-3-ethylcarbodiimide hydrochloride (40 mg, 0.208 mmol), 1-hydroxybenzotriazole (14 mg, 0.104 mmol) and triethylamine (52 mg, 0.52 mmol) were added. The reaction solution was left overnight at room temperature, and the reaction was completed. The reaction solution was washed with water, which was extracted with dichloromethane three times. The organic phases were washed with saturated brine, dried over anhydrous sodium sulfate, filtered, concentrated and purified by column chromatography to obtain the title compound 23 (12.0 mg, 0.020 mmol) with a yield of 18.7%.

1H NMR (400 MHz, DMSO-d6) δ 11.45 (s, 1H), 7.92 (t, J=4.8 Hz, 1H), 7.03 (d, J=8.1 Hz, 1H), 6.63-6.47 (m, 2H), 6.40 (s, 1H), 6.26 (d, J=2.5 Hz, 1H), 5.83 (s, 1H), 5.46 (d, J=8.0 Hz, 1H), 4.37 (d, J=15.9 Hz, 3H), 4.25 (d J=5.0 Hz, 2H), 3.82 (t, J=13.8 Hz, 4H), 3.37 (t, J=11.2 Hz, 3H), 3.20 (t, J=11.5 Hz, 2H), 3.07-2.84 (m, 3H), 2.18 (s, 3H), 2.07 (d, J=5.1 Hz, 6H), 1.85 (d, J=12.9 Hz, 2H), 1.64 (d, J=12.5 Hz, 2H), 1.48 (s, 2H), 1.33 (q, J=12.3, 11.7 Hz, 2H), 1.20 (s, 1H), 0.80 (t, J=6.7 Hz, 3H).

MS m/z (ESI): 614.3 $[M+1]^+$.

Example 24 N-(((4,6-dimethyl-2-oxo-1,2-dihydropyridin-3-yl)methyl)-3-(ethyl (tetrahydro-2H-pyran-4-yl)amino)-5-(6-fluoro-1-morpholino-2,3-dihydro-1H-inden-5-yl)-2-methylbenzamide 24

24

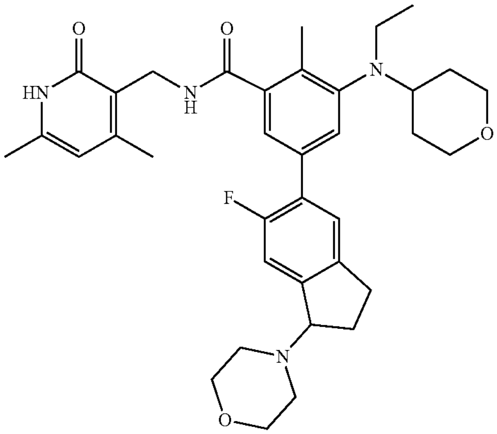

Using a synthesis method similar to that in Example 4, replacing 5-bromo-2,3-dihydro-1H-inden-1-one with 5-bromo-6-fluoro-2,3-dihydro-1H-inden-1-one, the title product 24 was obtained with a yield of 22%.

$^1$H NMR (400 MHz, Methanol-d4) δ 7.47-7.36 (m, 3H), 7.21 (d, J=1.9 Hz, 1H), 6.10 (s, 1H), 4.48 (s, 2H), 4.30 (dd, J=7.7, 5.2 Hz, 1H), 3.96-3.85 (m, 2H), 3.68 (dt, J=6.6, 3.4 Hz, 4H), 3.39-3.32 (m, 2H), 3.18-3.04 (m, 3H), 2.94 (ddd, J=38.7, 8.6, 6.4 Hz, 2H), 2.64-2.45 (m, 4H), 2.38 (s, 3H), 2.30 (s, 3H), 2.24-2.10 (m, 5H), 1.74 (d, J=12.9 Hz, 2H), 1.64 (td, J=11.7, 4.0 Hz, 2H), 0.88 (t, J=6.9 Hz, 3H).

MS m/z (ESI): 617.3 $[M+H]^+$.

Example 25 5-(6-chloro-1-morpholino-2,3-dihydro-1H-indan-5-yl)-N-(((4,6-dimethyl-2-oxo-1,2-dihydropyridin-3-yl)methyl)-3-(ethyl(tetrahydro-2H-pyran-4-yl)amino)-2-methylbenzamide 25

25

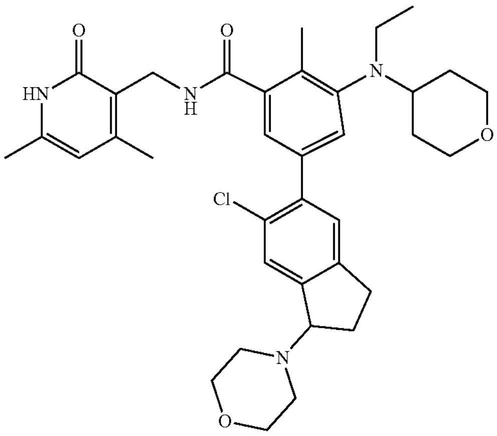

Using a synthesis method similar to that in Example 4, replacing 5-bromo-2,3-dihydro-1H-inden-1-one with 5-bromo-6-chloro-2,3-dihydro-1H-inden-1-one, the title product 25 was obtained with a yield of 17%.

$^1$H NMR (400 MHz, Methanol-d4) δ 7.42-7.31 (m, 3H), 7.19 (d, J=1.9 Hz, 1H), 6.0 (s, 1H), 4.49 (s, 2H), 4.30 (dd, J=7.7, 5.2 Hz, 1H), 3.96-3.85 (m, 2H), 3.68 (dt, J=6.6, 3.4 Hz, 4H), 3.39-3.41 (m, 2H), 3.18-3.04 (m, 3H), 2.92 (ddd, J=38.7, 8.6, 6.4 Hz, 2H), 2.64-2.42 (m, 4H), 2.38 (s, 3H), 2.31 (s, 3H), 2.26-2.10 (m, 5H), 1.77 (d, J=12.9 Hz, 21H), 1.64 (td, J=11.7, 4.0 Hz, 2H), 0.89 (t, J=6.9 Hz, 3H).

MS m/z (ESI): 633.3 [M+H]$^+$.

Example 26 N-(((4,6-dimethyl-2-oxo-1,2-dihydropyridin-3-yl)methyl)-3-(ethyl (tetrahydro-2H-pyran-4-yl)amino)-5-(7-fluoro-1-morpholino-2,3-dihydro-1H-inden-5-yl)-2-methylbenzamide 26

26

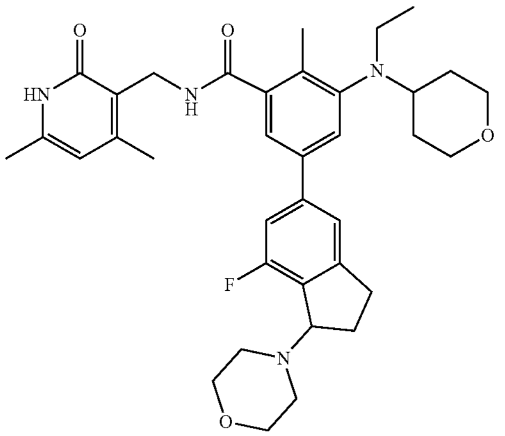

Using a synthesis method similar to that in Example 4, replacing 5-bromo-2,3-dihydro-1H-inden-1-one with 5-bromo-7-fluoro-2,3-dihydro-1H-inden-1-one, the title product 26 was obtained with a yield of 19%.

$^1$H NMR (400 MHz, Methanol-d4) δ 7.48-7.13 (m, 3H), 7.15 (d, J=1.9 Hz, 1H), 6.10 (s, 1H), 4.48 (s, 2H), 4.30 (dd, J=7.7, 5.2 Hz, 1H), 3.96-3.85 (m, 2H), 3.68 (dt, J=6.6, 3.4 Hz, 4H), 3.39-3.32 (m, 2H), 3.18-3.04 (m, 3H), 2.96 (ddd, J=38.7, 8.6, 6.4 Hz, 2H), 2.64-2.47 (m, 4H), 2.38 (s, 3H), 2.32 (s, 3H), 2.26-2.05 (m, 5H), 1.76 (d, J=12.9 Hz, 2H), 1.68 (td. J=11.7, 4.0 Hz, 2H), 0.88 (t, J=6.9 Hz, 3H).

MS m/z (ESI): 617.3 [M+H]$^+$.

Example 27 5-(3,3-dimethyl-1-morpholino-2,3-dihydro-1H-indan-5-yl)-N-(((4,6-dimethyl-2-oxo-1,2-dihydropyridin-3-yl)methyl)-3-(ethyl(tetrahydro-2H-pyran-4-yl)amino)-2-methylbenzamide 150

27

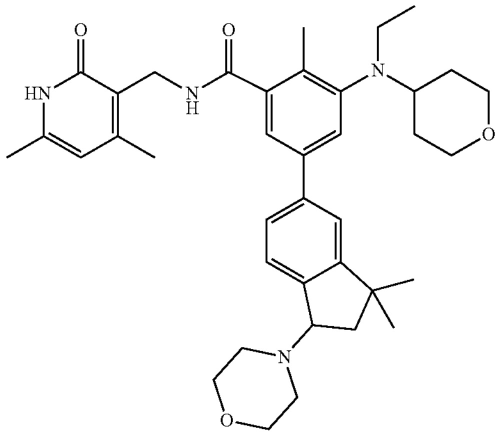

Using a synthesis method similar to that in Example 4, replacing 5-bromo-2,3-dihydro-1H-inden-1-one with 5-bromo-3,3-dimethyl-1-indanone, the title product 27 was obtained with a yield of 26%.

$^1$H NMR (400 MHz, Methanol-d4) δ 7.45-7.31 (m, 4H), 7.21 (d, J=1.9 Hz, 1H), 6.05 (s, 1H), 4.46 (s, 2H), 4.26 (dd, J=7.7, 5.2 Hz, 1H), 3.92-3.81 (m, 2H), 3.62 (dt, J=6.6, 3.4 Hz, 4H), 3.36-3.31 (m, 2H), 3.18-3.04 (m, 3H), 2.94 (ddd, J=38.7, 8.6, 6.4 Hz, 2H), 2.64-2.45 (m, 4H), 2.32 (s, 3H), 2.30 (s, 3H), 2.10-2.05 (m, 3H), 1.71 (d, J=12.9 Hz, 2H), 1.60 (td, J=11.7, 4.0 Hz, 2H), 0.87 (t, J=6.9 Hz, 3H) 0.81 (s, 6H).

MS m/z (ESI): 627.5 [M+H]$^+$.

Example 28 N-(((4,6-dimethyl-2-oxo-1,2-dihydropyridin-3-yl)methyl)-3-(ethyl (tetrahydro-2H-pyran-4-yl)amino)-6-fluoro-5-(6-fluoro-1-morpholino-2,3-dihydro-1H-inden-5-yl)-2-methylbenzamide 28

28

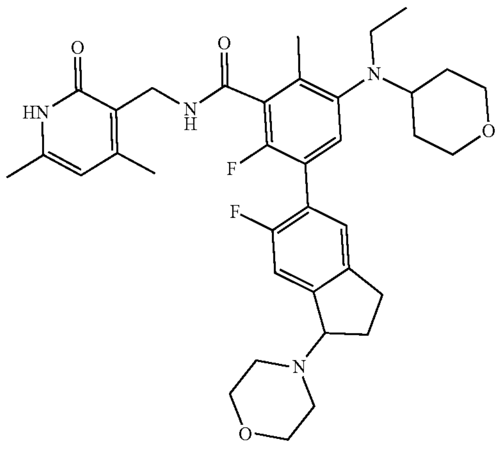

Using a synthesis method similar to that in Example 11, replacing 5-bromo-2,3-dihydro-1H-inden-1-one with 5-bromo-6-fluoro-2,3-dihydro-1H-inden-1-one, the title product 28 was obtained with a yield of 13%.

1H NMR (400 MHz, Methanol-d4) δ 7.41 (d, J=7.8 Hz, 1H), 7.22 (d, J=7.4 Hz, 1H), 7.15 (d, J=7.5 Hz, 1H), 6.02 (s, 1H), 4.43 (s, 2H), 4.30 (dd, J=7.7, 5.2 Hz, 1H), 3.83 (dd, J=11.1, 3.6 Hz, 2H), 3.62 (dt, J=6.3, 3.3 Hz, 4H), 3.28 (dd, J=11.7, 2.1 Hz, 2H), 3.05-2.90 (m, 4H), 2.82 (ddd, J=15.8, 8.6, 5.8 Hz, 1H), 2.60 (dt, J=9.7, 4.4 Hz, 2H), 2.45 (dt, J=1 1.4, 4.9 Hz, 2H), 2.35 (s, 3H), 2.29-2.01 (m, 8H), 1.69 (d, J=11.8 Hz, 2H), 1.51 (qd, J=11.5, 4.2 Hz, 2H), 0.87 (t, J=7.0 Hz, 3H).

MS m/z (ESI): 635.3 $[M+H]^+$.

Example 29 N-((4,6-dimethyl-2-oxo-1,2-dihydro-pyridin-3-yl)methyl)-3-(ethyl (tetrahydro-2H-pyran-4-yl)amino)-2-methyl-5-(1-(1-tetrahydro-2H-pyran-4-yl) indolin-5-yl)benzamide 29

29

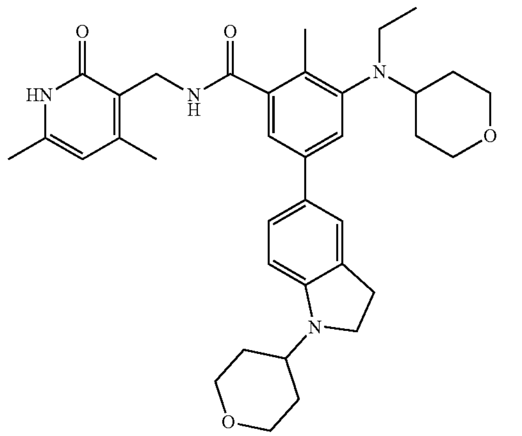

Using a synthesis method similar to that in Example 4, replacing 5-bromo-2,3-dihydro-1H-inden-1-one with 5-bromo-2,3-dihydro-1H-indole, and replacing morpholine with tetrahydro-4H-pyran-4-one, the title product 29 was obtained with a yield of 16%.

$^1$H NMR (400 MHz, Methanol-d4) δ 7.49-7.42 (m, 4H), 7.35 (d, J=1.8 Hz, 1H), 6.16 (s, 1H), 4.48 (s, 2H), 4.30 (dd, J=7.7, 4.8 Hz, 1H), 3.96-3.85 (m, 2H), 3.68 (dt, J=6.6, 3.4 Hz, 4H), 3.34-3.30 (m, 2H), 3.18-3.00 (m, 2H), 2.91 (ddd, J=38.7, 8.6, 6.4 Hz, 2H), 2.64-2.52 (m, 5H), 2.41 (s, 3H), 2.31 (s, 3H), 2.24-2.06 (m, 5H), 1.77 (d, J=12.9 Hz, 2H), 1.66 (td, J=11.7, 4.0 Hz, 2H), 0.86 (t, J=6.9 Hz, 3H).

MS m/z (ESI): 599.5 $[M+H]^+$.

Example 30 N-((4,6-dimethyl-2-oxo-1,2-dihydro-pyridin-3-yl)methyl)-3-(ethyl (tetrahydro-2H-pyran-4-yl)amino)-2-methyl-5-(2-morpholino-2,3-dihydro-1H-indan-5-yl)benzamide 30

30

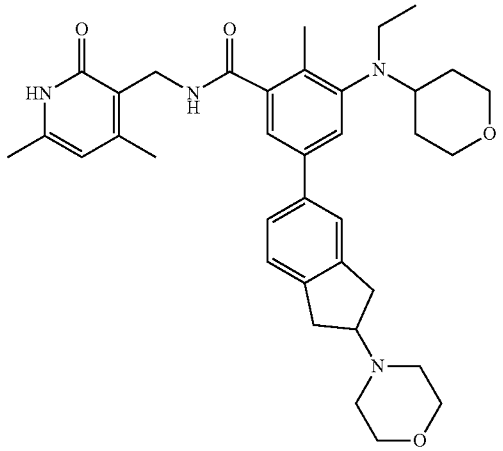

Using a synthesis method similar to that in Example 4, replacing 5-bromo-2,3-dihydro-1H-inden-1-one with 5-bromo-2-indanone, the title product 30 was obtained with a yield of 25%.

$^1$H NMR (400 MHz, Methanol-d4) δ 7.48-7.35 (m, 3H), 7.12 (d, J=1.9 Hz, 1H), 6.06 (s, 1H), 4.45 (s, 2H), 4.25 (dd, J=7.7, 5.2 Hz, 1H), 3.93-3.82 (m, 2H), 3.64 (dt, J=6.6, 3.4 Hz, 4H), 3.36-3.31 (m, 2H), 3.18-3.04 (m, 3H), 2.94 (ddd, J=38.7, 8.6, 6.4 Hz, 2H), 2.61-2.43 (m, 5H), 2.38 (s, 3H), 2.30 (s, 3H), 2.24-2.05 (m, 4H), 1.74 (d, J=12.9 Hz, 2H), 1.62 (td, J=11.7, 4.0 Hz, 2H), 0.87 (t, J=6.9 Hz, 3H).

MS m/z (ESI): 599.5 $[M+H]^+$.

Bioassay

Experiment 1. Determination of Activity of the Compound of the Present Invention on the Wild-Type Polycomb Repressive Complex 2 (PRC2) *Drosophila* Enhancer of Zeste Homolog 2 (EZH2)

1. Experiment Purpose and Method

In this experiment, radiometric assay was used to test the bind strength of the compound of the present invention to wild-type Polycomb Repressive Complex 2 (PRC2) *Drosophila* enhancer of zeste homolog 2 (EZH2) wild-type, and the in vitro activity of the compound was evaluated based on the half inhibitory concentration (IC50).

2. Experimental Scheme 2.1 Preparation of Experimental Compounds

Compounds 1-30, EPZ-6438, and GSK126 used in this experiment were dissolved in dimethyl sulfoxide (DMSO) to prepare a mother liquor of 10 millimoles per liter (mM). The highest concentration during the test was 1 micromole per liter (μM), which is to be diluted by 5 times, with a total of 7 concentration gradients, and repetitive wells were set up.

2.2 Experiment Process 10 microliters (μL) of the compound of the test example and wild-type EZH2 were added to each well. After being incubated at room temperature for 15 minutes, peptides and [3H]-labeled methyl donor S-adenosylmethionine (SAM)

were added. After reacting at room temperature for 1 hour (h), cold SAM was added to terminate the reaction. 25 μl reaction solution was transferred to the scintillation plate. After incubating for 1 hour (h) at room temperature, the plate was washed three times with deionized water and 0.1% Tween 20. The value was read with a PerkinElmer liquid scintillation/luminescence counter, and the half inhibitory concentration (IC50) of the compound was calculated with the Prism 5 software (GraphPad Prism 5).

2.3 Test Results and Conclusions

The results showed that the IC50 of EPZ-6438 against wild-type EZH2 was 1.67 nanomolar per liter (nM), and the IC50 of GSK126 against wild-type EZH2 was 1.64 nanomolar per liter (nM). The compounds of the examples have a strong inhibitory effect on wild-type EZH2, and the results are shown in Table 1.

Experiment 2. Determination of the Activity of the Compound of the Present Invention on Mutant PRC2 Complex (EZH2 Mutant)

1. Detection Method: AlphaLISA

2. Experimental Steps

According to the instructions, the test buffer was used to dilute the enzyme complex, the methyl donor S-adenosylmethionine (SAM) (Sigma, item number: A7007), the protease inhibitor (sinefungin) (Sigma, item number: S8559), and the biotinylated peptide substrate (Napai AnaSpec, item number: 64440). 2.5 μl 4-fold enzyme complex (BPS, item number: 51004), 2.5 μl 4-fold inhibitor example and test buffer, 5 μl biotin-labeled histone 3 (H3) and 2-fold methyl donor S-adenosylmethionine were added, and incubated at room temperature. Finally, 15 μl detection solution mixture was added under low light, and incubated at room temperature for 60 minutes, and read the value.

3 Test Results and Conclusions

The results showed that the positive drug EPZ-6438 inhibited the mutant Y641F gene enhancer homolog 2 (EZH2) with an IC50 of 1.81 nM, the A677G gene enhancer homolog 2 (EZH2) with an IC50 of 1.87 nM, and Y641N gene enhancer homolog 2 (EZH2) with an IC50 of 1.34 nM. The IC50 of GSK126 for the inhibition of mutant Y641F EZH2 was 1.63 nM, the IC50 for A677G EZH2 inhibition was 1.23 nM, and the IC50 for Y641N EZH2 inhibition was 1.11 nM. The compounds of the examples have strong inhibitory effects on mutant EZH2, and the results are shown in Table 1.

TABLE 1

Inhibitory activity of compounds on PRC2

| Compound Number | Wild-type EZH2 IC50 nmol/L (nM) | Mutant EZH2 (Y641F) IC50 nmol/L (nM) | Mutant EZH2 (A677G) IC50 nmol/L (nM) | Mutant EZH2 (Y641N) IC50 nmol/L (nM) |
|---|---|---|---|---|
| 1 | 0.86 | 0.69 | 0.35 | 0.29 |
| 2 | 0.99 | 0.83 | 0.54 | 0.43 |
| 3 | 0.97 | 0.58 | 0.49 | 0.37 |
| 4 | 0.95 | 0.83 | 0.66 | 0.37 |
| 5 | 0.79 | 0.65 | 0.36 | 0.1 |
| 6 | 0.52 | 0.33 | 0.21 | 0.14 |
| 7 | 0.61 | 0.51 | 0.33 | 0.11 |
| 8 | 0.68 | 0.47 | 0.36 | 0.21 |
| 9 | 0.9 | 0.48 | 0.37 | 0.26 |
| 10 | 0.63 | 0.58 | 0.42 | 0.3 |
| 11 | 0.6 | 0.54 | 0.34 | 0.23 |
| 12 | 0.95 | 0.89 | 0.59 | 0.37 |
| 13 | 0.95 | 0.81 | 0.46 | 0.34 |
| 14 | 0.76 | 0.61 | 0.56 | 0.44 |
| 15 | 0.9 | 0.78 | 0.24 | 0.1 |
| 16 | 0.95 | 0.82 | 0.74 | 0.61 |
| 17 | 0.74 | 0.43 | 0.34 | 0.21 |
| 18 | 0.8 | 0.71 | 0.64 | 0.5 |
| 19 | 0.61 | 0.39 | 0.23 | 0.08 |
| 20 | 0.97 | 0.64 | 0.44 | 0.23 |
| 21 | 0.9 | 0.72 | 0.42 | 0.28 |
| 22 | 0.71 | 0.44 | 0.37 | 0.23 |
| 23 | 0.89 | 0.84 | 0.66 | 0.5 |
| 24 | 0.87 | 0.75 | 0.61 | 0.46 |
| 25 | 0.88 | 0.65 | 0.43 | 0.26 |
| 26 | 0.76 | 0.68 | 0.5 | 0.32 |
| 27 | 0.66 | 0.41 | 0.26 | 0.19 |
| 28 | 0.91 | 0.75 | 0.5 | 0.3 |
| 29 | 0.53 | 0.44 | 0.31 | 0.18 |
| 30 | 0.61 | 0.39 | 0.28 | 0.12 |
| EPZ-6438 | 1.67 | 1.81 | 1.87 | 1.34 |
| GSK126 | 1.64 | 1.63 | 1.23 | 1.11 |

Experiment 3. Analysis of the Compound of the Present Invention on the Proliferation of Human Diffuse Large B-Cell Lymphoma Cells (WSU-DLCL2 Cells)

1. Experiment Purpose and Method

In this experiment, Calcein AM staining method was used to measure the in vitro anti-proliferation effect of the compound of the present invention on human diffuse large B-cell lymphoma cells (WSU-DLCL2 cells).

2. Experimental Scheme 2.1 Cell Culture

Human diffuse large B-cell lymphoma cells (WSU-DLCL2 cells) were ordered from Nanjing Kebai. RPMI1640 (Corning, 35417005) with 10% fetal bovine serum (Ausbina, 0986180) and 1% penicillin/streptomycin double antibody (Corning, 30002297) were used for culture. By observing under a microscope, it was confirmed that the cells are in good condition. The cells were transferred to a 15 mL centrifuge tube, which was centrifuged at 1000 rpm for 5 minutes. The supernatant was discarded, the complete medium was added, and the single cell suspension was pipetted into a single cell suspension and placed in a 37° C., 5% $CO_2$ incubator (Thermo, 311) for culture.

2.2 Compound Preparation and Compound Plate Preparation

Compounds 1-30, EPZ-6438, and GSK126 used in this experiment were dissolved in dimethyl sulfoxide (DMSO) to prepare a 10 mM mother liquor. Gradient dilutions of the compounds in DMSO were performed, and a compound plate with a final concentration of 500-fold was prepared. 1.2 μL of 500× compound was pipetted, transferred to 200 μL medium, and pipetted to mix well to obtain a 3× compound intermediate plate. 50 μL 3× compound is pipetted and added to the cell plate according to the set arrangement.

2.3 Experiment Process

When the diffuse large B-cell lymphoma cells (WSU-DLCL2 cell line) grow well, the cells were collected and counted. The cell concentration was adjusted to 100000 cells/mL. The cells of the above concentration were inoculated in 96-well plates, 100 μL/well (the number of cells in each well is 10,000). The cell plate was placed in a carbon dioxide incubator for 4 days. The cell plate was taken out. After mixed uniformly, a certain volume of cell suspension was drawn, and stained with Calcein AM. The number of cells in each well was counted with Acumen. According to the number of detected cells, 10,000 cells were re-inoculated in 96-well plates. As above, the compound was added. After placed in a carbon dioxide incubator for 3 days (day 7). The cell plate was taken out again. After mixed uniformly, a certain volume of cell suspension was drawn, stained with Calcein AM. The number of cells in each well was counted with Acumen. The cells were cultured for another 4 days (day 11), and the cell plate was taken out for the third time. After mixed uniformly, a certain volume of cell suspension was drawn, and stained with Calcein AM. The number of cells in each well was counted with Acumen. According to the number of detected cells, 10,000 cells were re-inoculated in 96-well plates. As above, the compound was added. After placed in a carbon dioxide incubator for 3 days (day 7), the cells were cultured for another 7 days (day 14). After Calcein AM staining, the number of the cells was counted to obtain the final count result. The data of day 14 was processed to obtain the corresponding half-inhibitory concentration (IC50).

2.4 Data Processing and Statistics

The cell survival rate is calculated by the formula: $V_{sample}/V_{vehicle\ control}\times 100\%$, wherein $V_{sample}$ is the read of the drug treatment group, and $V_{vehicle\ control}$ is the average of the solvent control group. Using GraphPad Prism 5 software, a non-linear regression model was used to draw the S-type dose-survival rate curve and to calculate the IC50 value.

2.5 Test Results and Conclusions

The results showed that the half inhibitory concentration (IC50) of EPZ-6438 on the proliferation of human diffuse large B-cell lymphoma cells (WSU-DLCL2 cells) was 35.33 nM, and the half inhibitory concentration (IC50) of GSK126 on the proliferation of human diffuse large B-cell lymphoma cells (WSU-DLCL2 cells) was 34.12 nM. The compounds of the examples have a strong inhibitory effect on the proliferation of human diffuse large B-cell lymphoma cells (WSU-DLCL2 cells), and the inhibitory activity is better than EPZ-6438 and GSK126. The results are shown in Table 2.

Experiment 4: Analysis of the Compound of the Present Invention on the Proliferation of Human Diffuse Large Cell Lymphoma B Lymphocytes (Pfeiffer Cells)

1. Experiment Purpose and Method

In this experiment, Calcein AM staining method was used to measure the in vitro anti-proliferation effect of the compound of the present invention on human diffuse large cell lymphoma B lymphocytes (Pfeiffer cells).

2. Experimental Scheme 2.1 Cell Culture

Human diffuse large cell lymphoma B lymphocytes (Pfeiffer cells) were ordered from Nanjing Kebai. RPMI1640 (Corning, 35417005) with 20% fetal bovine serum (Ausbina, 0986180) and 1% penicillin/streptomycin double antibody (Corning, 30002297) were used for culture. By observing under a microscope, it was confirmed that the cells are in good condition. The cells were transferred to a 15 mL centrifuge tube, which was centrifuged at 1000 rpm for 5 minutes. The supernatant was discarded, the complete medium was added, and the single cell suspension was pipetted into a single cell suspension and placed in a 37° C., 5% $CO_2$ incubator (Thermo, 311) for culture.

2.2 Compound Preparation and Compound Plate Preparation

Compounds 1-30, EPZ-6438, and GSK126 used in this experiment were dissolved in dimethyl sulfoxide (DMSO) to prepare a 10 mM mother liquor. The highest concentration during the test was 10 μM. Gradient dilution of the compounds in DMSO were performed, and a compound plate with a final concentration of 500 times was prepared. 1.2 μL of 500× compound was pipetted, transferred to 200 μL of medium, and pipetted to mix well to obtain a 3× compound intermediate plate. 50 μL of 3× compound is pipetted and added to the cell plate according to the set arrangement.

2.3 Experiment Process

When the human diffuse large cell lymphoma B lymphocytes (Pfeiffer cells) grow well, the cells were collected and counted. The cell concentration was adjusted to 100000 cells/mL. The above concentration of cells was inoculated in 96-well plates, 100 μL/well (the number of cells in each well is 10,000). The cell plate was placed in a carbon dioxide incubator for 4 days. The cell plate was taken out. After mixed well, a certain volume of cell suspension was drawn, and stained with Calcein AM. The number of cells in each well was counted with Acumen. According to the number of detected cells, 10,000 cells were re-inoculated in 96-well plates. As above, the compound was added. After placed in a carbon dioxide incubator for 3 days (day 7), the cell plate was taken out again. After mixed well, a certain volume of cell suspension was drawn, and stained with Calcein AM. The number of cells in each well was counted with Acumen. The cells were cultured for another 4 days (day 11), and the cell plate was taken out for the third time. After mixed well, a certain volume of cell suspension was drawn, and stained with Calcein AM. The number of cells in each well was counted with Acumen. According to the number of detected cells, 10,000 cells were re-inoculated in 96-well plates. As above, the compound was added. It was placed in a carbon dioxide incubator for 3 days (day 7). The cells were cultured for another 7 days (day 14). After Calcein AM staining, the number of the cells was counted to obtain the final count result. The data of day 14 was processed to obtain the corresponding half-inhibitory concentration (IC50).

2.4 Data Processing and Statistics

The cell survival rate is calculated by the formula: $V_{sample}/V_{vehicle\ control}\times 100\%$, wherein $V_{sample}$ is the read of the drug treatment group, and $V_{vehicle\ control}$ is the average of the solvent control group. Using GraphPad Prism 5 software, a non-linear regression model was used to draw the S-type dose-survival rate curve and to calculate the IC50 value.

2.5 Test Results and Conclusions

The results showed that the half inhibitory concentration (IC50) of EPZ-6438 on the proliferation of human diffuse large cell lymphoma B lymphocytes (Pfeiffer cells) was 8.33 nM, and the half inhibitory concentration (IC50) of GSK126 on the proliferation of human diffuse large cell lymphoma B lymphocytes (Pfeiffer cells) was 12.22 nM. The compounds of the examples have a strong inhibitory effect on the proliferation of human diffuse large cell lymphoma B lymphocytes (Pfeiffer cells), and the inhibitory activity is better than EPZ-6438 and GSK126. The results are shown in Table 2.

Experiment 5: Analysis of the Compound of the Present Invention on the Proliferation of Human Diffuse Large B-Cell Lymphoma Cells (Karpas 422 Cells)

1. Experiment Purpose and Method

In this experiment, Calcein AM staining method was used to measure the in vitro anti-proliferation effect of the compound of the present invention on human diffuse large B-cell lymphoma cells (Karpas 422 cells).

2. Experimental Scheme 2.1 Cell Culture

Human diffuse large B-cell lymphoma cells (Karpas 422 cells) were ordered from Nanjing Kebai. RPMI1640 (Corning, 35417005) with 20% fetal bovine serum (Ausbina, 0986180) and 1% penicillin/streptomycin antibody (Corning, 30002297) was used for culture. By observing under a microscope, it was confirmed that the cells are in good condition. The cells were transferred to a 15 mL centrifuge tube, which was centrifuged at 1000 rpm for 5 minutes. The supernatant was discarded, the complete medium was added, and the single cell suspension was pipetted into a single cell suspension and placed in a 37° C., 5% $CO_2$ incubator (Thermo, 311) for culture.

2.2 Compound Preparation and Compound Plate Preparation

Compounds 1-30, EPZ-6438, and GSK126 used in this experiment were dissolved in dimethyl sulfoxide (DMSO) to prepare a 10 mM mother liquor. The highest concentration during the test was 10 μM. Gradient dilution of the compounds in DMSO were performed, and a compound plate with a final concentration of 500 times were prepared. 1.2 μL of 500× compound was pipetted, transferred to 200 μL of medium, and pipetted to mix well to obtain a 3× compound intermediate plate. 50 μL of 3× compound is pipetted and added to the cell plate according to the set arrangement.

2.3 Experiment Process

When the diffuse large B-cell lymphoma cells (Karpas 422 cell) grow well, the cells were collected and counted. The cell concentration was adjusted to 100000 cells/mL. The above concentration of cells was inoculated in 96-well plates, 100 μL/well (the number of cells in each well is 10,000). The cell plate was placed in a carbon dioxide incubator for 4 days. The cell plate was taken out. After mixed well, a certain volume of cell suspension was drawn, and stained with Calcein AM. The number of cells in each well was counted with Acumen. According to the number of detected cells, 10,000 cells were re-inoculated in 96-well plates. As above, the compound was added. After placed in a carbon dioxide incubator for 3 days (day 7), the cell plate was taken out again. After mixed well, a certain volume of cell suspension was drawn, and stained with Calcein AM. The number of cells in each well was counted with Acumen. The cells were cultured for another 4 days (day 11), and the cell plate was taken out for the third time. After mixed well, a certain volume of cell suspension was drawn, and stained with Calcein AM. The number of cells in each well was counted with Acumen. According to the number of detected cells, 10,000 cells were re-inoculated in 96-well plates. As above, the compound was added. After placed in a carbon dioxide incubator for 3 days (day 7), the cells were cultured for another 7 days (day 14). After Calcein AM staining, the number of the cells was counted to obtain the final count result. The data of day 14 was processed to obtain the corresponding half-inhibitory concentration (IC50).

2.4 Data Processing and Statistics

The cell survival rate is calculated by the formula: $V_{sample}/V_{vehicle\ control}\times 100\%$, wherein $V_{sample}$ is the read of the drug treatment group, and $V_{vehicle\ control}$ is the average of the solvent control group. Using GraphPad Prism 5 software, a non-linear regression model was used to draw the S-type dose-survival rate curve and to calculate the IC50 value.

2.5 Test Results and Conclusions

The results showed that the half inhibitory concentration (IC50) of EPZ-6438 on the proliferation of human diffuse large B-cell lymphoma cells (Karpas 422 cells) was 15.65 nM, and the half inhibitory concentration (IC50) of GSK126 on the proliferation of human diffuse large B-cell lymphoma cells (Karpas 422 cells) was 20.32 nM. The compounds of the examples have a strong inhibitory effect on the proliferation of human diffuse large B-cell lymphoma cells (Karpas 422 cells), and the inhibitory activity is better than EPZ-6438 and GSK126. The results are shown in Table 2.

TABLE 2

Inhibitory effects of compounds on the proliferation of EZH2-sensitive cells

| Compound Number | WSU-DLCL2 proliferation IC50 nmol/L (nM) | Pfeiffer proliferation IC50 nmol/L (nM) | Karpas422 proliferation IC50 nmol/L (nM) |
|---|---|---|---|
| 1 | 2.87 | 1.34 | 2.15 |
| 2 | 1.58 | 0.75 | 1.08 |
| 3 | 2.68 | 1.67 | 2.5 |
| 4 | 2.36 | 1.73 | 1.82 |
| 5 | 5.85 | 2.84 | 3.23 |
| 6 | 5.13 | 3.2 | 4.15 |
| 7 | 1.34 | 0.56 | 0.98 |
| 8 | 2.26 | 1.03 | 2.38 |
| 9 | 4.68 | 3.47 | 4.15 |
| 10 | 1.17 | 0.38 | 0.58 |
| 11 | 2.92 | 1.08 | 1.87 |
| 12 | 2.36 | 1.69 | 1.84 |
| 13 | 1.28 | 0.87 | 0.95 |
| 14 | 4.15 | 2.89 | 3.76 |
| 15 | 2.46 | 0.93 | 2.15 |
| 16 | 5.12 | 1.87 | 3.34 |
| 17 | 3.71 | 1.27 | 2.6 |
| 18 | 2.89 | 1.86 | 2.34 |
| 19 | 7.75 | 2.34 | 3.21 |
| 20 | 7.84 | 2.85 | 3.62 |
| 21 | 9.38 | 7.16 | 8.15 |
| 22 | 6.38 | 1.87 | 3.67 |
| 23 | 6.48 | 4.36 | 4.09 |
| 24 | 5.28 | 2.96 | 4.47 |
| 25 | 2.32 | 1.74 | 1.86 |
| 26 | 9.42 | 5.86 | 6.47 |
| 27 | 1.71 | 0.15 | 0.93 |
| 28 | 3.47 | 1.53 | 2.7 |
| 29 | 2.18 | 1.42 | 1.99 |
| 30 | 1.15 | 0.3 | 0.82 |
| EPZ-6438 | 35.33 | 8.33 | 15.65 |
| GSK126 | 34.12 | 12.22 | 20.32 |

Experiment 6. Pharmacokinetics Experiment of the Compound of the Present Invention in Rats 1. Abstract Male SD rats weighing 200-300 g and 8 weeks old were used as experimental animals. The LC/MS/MS method was used to determine the drug concentration in plasma at different times after intravenous and intragastric application of the compound of Example 6, the compound of Example 8, the compound of Example 10, the compound of Example 11, the compound of Example 12, the compound of Example 13, the compound of Example 15, the compound of Example 16, the compound of Example 18, the compound of Example 21, the compound of Example 25, and the compound of Example 30. The pharmacokinetic behavior of the compound of the present invention in rats was studied, and the pharmacokinetic characteristics thereof were evaluated.

2. Experimental Scheme 2.1 Experimental Compound

The compound of Example 6, the compound of Example 8, the compound of Example 10, the compound of Example 11, the compound of Example 12, the compound of Example 13, the compound of Example 15, the compound of Example 16, the compound of Example 18, the compound of Example 21, the compound of Example 25, and the compound of Example 30 were determined.

2.2 Preparation of Compounds

A certain amount of the compound was weighed, dissolved in 0.10% tween for vortex and ultrasound, and then 0.5% sodium carboxymethyl cellulose (CMC-Na) solution was added to prepare a uniform solution.

2.3 Plasma Collection and Processing

The above-mentioned compounds were applied intravenously and orally to rats at a dose of 4 mg/kg and a dose of 20 mg/kg, respectively. At 0.083 h, 0.25 h, 0.5 h, 1.0 h, 2.0 h, 4.0 h, 6.0 h, 8.0 h, 12.0 h, and 24.0 h after application, 0.2 mL of blood was collected from the orbit, and placed in an anticoagulant tube, which was centrifuged at 6000 rpm for 10 minutes at 4° C. The plasma was separated and stored at −80° C.

2.4 Experimental Results and Conclusions

The pharmacokinetic parameters of the compound of the present invention after application are shown in Table 3 below. As shown in Table 3, the compounds of the present invention have better metabolic characteristics and better bioavailability.

TABLE 3

Pharmacokinetic parameters of the compounds of the invention

| | Intravenous dosing (4 mg/kg) | | Oral dosing (20 mg/kg) | | |
|---|---|---|---|---|---|
| Compound | Area under the curve (AUC, ng/mL · h) | Half life ($T_{1/2}$, h) | Blood drug level (Cmax, ng/mL) | Area under the curve (AUC, ng/mL · h) | Bioavailability (F %) |
| 6 | 966.24 | 1.12 | 455.5 | 1607.34 | 33.27 |
| 8 | 965.72 | 1.32 | 594.23 | 1754.23 | 36.33 |
| 10 | 937.25 | 1.64 | 405.1 | 1435.87 | 30.64 |
| 11 | 954.12 | 1.34 | 489.07 | 1270.89 | 26.64 |
| 12 | 956.23 | 1.42 | 480 | 1308.6 | 27.37 |
| 13 | 977.13 | 1.34 | 402.8 | 1687.5 | 34.54 |
| 15 | 893.24 | 1.42 | 499.88 | 1541.29 | 34.51 |
| 16 | 975.12 | 1.87 | 433.33 | 1188.18 | 24.37 |
| 18 | 968.95 | 1.57 | 457.03 | 1663.2 | 34.33 |
| 21 | 932.41 | 1.72 | 426.3 | 1248.96 | 26.79 |
| 25 | 933.12 | 1.38 | 501.41 | 1186.93 | 25.44 |
| 30 | 878.95 | 1.24 | 442.53 | 1257.34 | 28.61 |

Experiment 7. Acute Toxicity Experiment of the Compound of the Present Invention 1. Experiment Purpose and Method The purpose of this experiment is to test the acute toxicity effect of the compound on mice.

The mice were administrated different doses of the compound of Example 6, the compound of Example 8, the compound of Example 10, and the compound of Example 11, and observed for 14 days. The death, toxic reaction, weight change, diet, appearance, behavior, etc. of the animal were recorded. The animals were dissected at the end point, and organs were taken for histopathological examination.

2. Experimental Results and Conclusions

The median lethal dose (LD50) of the compound of the present invention was more than 1000 mg/kg, and the safety was good. Compared with the mice in the control group, the mice in the application group showed no abnormal body weight and behavior within 14 days from the application day, and the compound of the present invention did not show obvious toxicity.

Experiment 8. Pharmacodynamic Experiment of the Compound of Example 8, the Compound of Example 12, the Compound of Example 21, and the Compound of Example 29 of the Present Invention in Human Diffuse Large B-Cell Lymphoma Cell (WSU-DLCL2 Cell) Mouse Xenograft Tumor Model 1. Abstract 8-week-old female mice weighing 18 g-20 g with combined severe immunodeficiency (CB17/SCID) were used as experimental animals, and the results of drug efficacy on mouse tumors after intragastric application of SCID transplanted tumor mice were determined. The effect of the compound of the invention on tumor growth was explored.

2. Experimental Scheme 2.1 Experimental Compound

The compound of Example 8

2.2 Preparation of Compounds

A certain amount of the compound was weighed, dissolved in 0.1% tween for vortex and ultrasound, and then 0.5% sodium carboxymethyl cellulose (CMC-Na) solution was added to prepare a uniform solution.

2.3 Cell Culture

Human diffuse large B-cell lymphoma cells (WSU-DLCL2 cells) were ordered from Nanjing Kebai. RPMI1640 (Corning, 35417005) with 10% fetal bovine serum (Ausbina, 0986180) and 1% penicillin/streptomycin double antibody (Corning, 30002297) were used for culture. By observing under a microscope, it was confirmed that the cells are in good condition. The cells were transferred to a 15 mL centrifuge tube, which was centrifuged at 1000 rpm for 5 minutes. The supernatant was discarded, the complete medium was added, and the single cell suspension was pipetted into a single cell suspension and placed in a 37° C., 5% $CO_2$ incubator (Thermo, 311) for culture.

2.4 Experiment Process

Under aseptic conditions, the diffuse large B-cell lymphoma cells (WSU-DLCL2 cells) in logarithmic growth phase were digested, mixed with Matrigel, and then transplanted into the mice with combined severe immunodeficiency (CB17/SCID) under the skin on the right side of the back. Each mouse was inoculated with $1*10^7$ cells in a volume of 100 μL. After the inoculation, the mice were randomly divided into 12 groups according to the size of the tumor, and 6 mice in each group were tested in vivo. The positive control group was EPZ-6438 and GSK126, and the negative control group was given the same amount of solvent. The specific design is shown in Table 4.

TABLE 4

In vivo efficacy experiments of the compounds

| Group | Animal Number | Test drug | Dose (mg/kg) | Application Volume (ml/kg) | Application route | Dosing schedule |
|---|---|---|---|---|---|---|
| 1 | 6 | vehicle | NA | 10 | Gastric Irrigation | Twice a day for 21 days |

TABLE 4-continued

In vivo efficacy experiments of the compounds

| Group | Animal Number | Test drug | Dose (mg/kg) | Application Volume (ml/kg) | Application route | Dosing schedule |
|---|---|---|---|---|---|---|
| 2 | 6 | EPZ-6438 | 150 | 10 | Gastric Irrigation | Twice a day for 21 days |
| 3 | 6 | GSK126 | 50 | 10 | Abdominal | Once a day for 21 days |
| 4 | 6 | Example 8 | 150 | 10 | Gastric Irrigation | Twice a day for 21 days |
| 5 | 6 | Example 12 | 150 | 10 | Gastric Irrigation | Twice a day for 21 days |
| 6 | 6 | Example 21 | 150 | 10 | Gastric Irrigation | Once a day for 21 days |
| 7 | 6 | Example 29 | 150 | 10 | Gastric Irrigation | Twice a day for 21 days |

2.5 Experimental Results and Conclusions

EPZ-6438 inhibits tumor growth by 59% at a dose concentration of 150 mg/kg, while GSK126 inhibits tumor growth by only 61% at a dose concentration of 50 mg/kg. The compound of Example 8, the compound of Example 12, the compound of Example 21, and the compound of Example 29 inhibits tumor growth inhibitory ratio of 82%, 85%, 90%, and 78% at a dose concentration of 150 mg/kg. The above showed that the compound of Example 8 of the present invention has a stronger tumor growth inhibitory effect than EPZ-6438 and GSK126 in a xenograft model of diffuse large B-cell lymphoma cells (WSU-DLCL2 cell line).

These examples are only preferred examples of the invention, and the scope of the invention is not limited to these examples. Any changes or substitutions that can be easily conceived by those skilled in the art within the technical scope disclosed by the present invention should be covered by the scope of the present invention.

The invention claimed is:

1. A compound represented by general formula (I), or a tautomer, a mesomer, a racemate, an enantiomer, a diastereomer or a mixture thereof, a pharmaceutically acceptable salt, a polymorph, a solvate or an isotopic derivative thereof, (I)

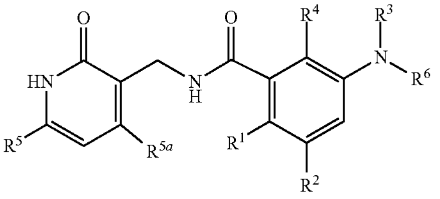

wherein, $R^1$ is hydrogen, —F or —Cl;

$R^2$ is selected from the group consisting of

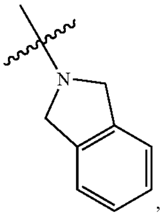 ,
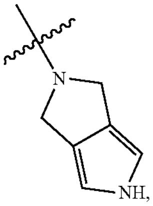
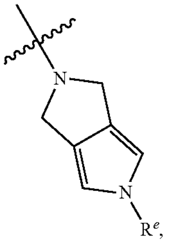
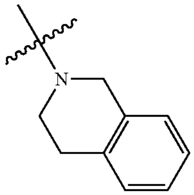 ,
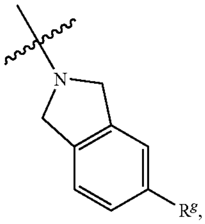
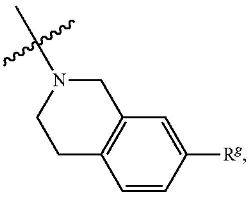
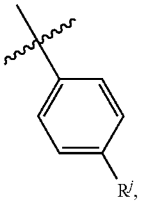
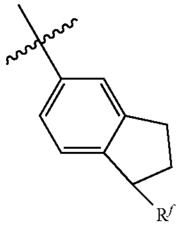 and
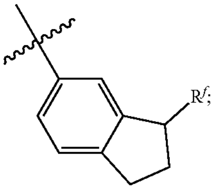

$R^e$ is selected from the group consisting of —$C_{1-4}$ alkyl, —$C_{2-4}$ alkyl substituted by —$C_{1-3}$ alkyl, —$C_{2-4}$ alkyl substituted by hydroxyl, —$C_{1-4}$ alkylene-OH, -$T^0$, —$C_{1-4}$ alkylene-$T^0$, —$(CH_2)_n$—$CF_3$, —$(CH_2)_n$—$CF_2$—$CF_3$, —$(CH_2)_n$—$CHF_2$, —$(CH_2)_n$—$CH_2F$, —$(CH_2)_n$—O—$C_{1-3}$ alkyl, —C(O)—$C_{1-3}$ alkyl, —$(CH_2)_n$—C(O)—$C_{1-3}$ alkyl, —C(O)—$C_{2-4}$ alkenyl, —C(O)—$CF_3$, —C(O)—$(CH_2)_n$—$CF_3$, —C(O)—$(CH_2)_n$—$CF_2$—$CF_3$, —C(O)—$(CH_2)_n$—$CHF_2$, —C(O)—$(CH_2)_n$—$CH_2F$, —C(O)-$T^0$, —C(O)—$C_{1-3}$ alkylene-$T^0$, tert-butoxycarbonyl, —C(O)—O—$C_{1-3}$ alkyl, —C(O)—O—$(CH_2)_n$—$CF_3$, —C(O)—O—$(CH_2)_n$—$CHF_2$, —C(O)—O—$(CH_2)_n$—$CH_2F$, —C(O)—O-$T^0$, —C(O)—O—$C_{1-3}$ alkylene-$T^0$, —$S(O)_2$—$C_{1-3}$ alkyl, —$S(O)_2$—$(CH_2)_n$—$CF_3$, —$S(O)_2$—$(CH_2)_n$—$CHF_2$, —$S(O)_2$—$(CH_2)_n$—$CH_2F$, —$S(O)_2$-$T^0$, and —$S(O)_2$—$C_{1-3}$ alkylene-$T^0$;

$R^f$ and $R^g$ are each independently selected from the group consisting of halogen, —OH, —$C_{1-4}$ alkylene-OH, —$CF_3$, —$CHF_2$, —$CH_2F$, —$C_{1-4}$ alkyl, —$C_{2-4}$ alkyl substituted by —$C_{1-3}$ alkyl, —$(CH_2)_n$—$CF_3$, —$(CH_2)_n$—$CHF_2$, —$(CH_2)_n$—$CH_2F$, -$T^0$, —$C_{1-3}$ alkylene-$T^0$, —$NR^aR^b$, —$C_{1-3}$ alkylene-$NR^aR^b$, —O—$C_{1-4}$ alkyl, —O—$C_{2-4}$ alkenyl, —O—$C_{1-4}$ alkylene-OH, —O—$(CH_2)_n$—$CF_3$, —O—$(CH_2)_n$—$CHF_2$, —O—$(CH_2)_n$—$CH_2F$, —O-$T^0$, —O—$C_{1-3}$ alkylene-$T^0$, —NH—C(O)—$C_{2-4}$ alkenyl, C(O)—$C_{1-3}$ alkyl, —$(CH_2)_n$—C(O)—$C_{1-3}$ alkyl, —C(O)—$C_{2-4}$ alkenyl, —C(O)—$(CH_2)_n$—$CF_3$, —C(O)—$(CH_2)_n$—$CHF_2$, —C(O)—$(CH_2)_n$—$CH_2F$, —C(O)-$T^0$, —C(O)—$C_{1-3}$ alkylene-$T^0$, tert-butoxycarbonyl, —C(O)—O—$C_{1-3}$ alkyl, —C(O)—O—$(CH_2)_n$—$CF_3$, —C(O)—O—$(CH_2)_n$—$CHF_2$, —C(O)—O—$(CH_2)_n$—$CH_2F$, —C(O)—O-$T^0$, —C(O)—O—$C_{1-3}$ alkylene-$T^0$, —$S(O)_2$—$C_{1-3}$ alkyl, —$S(O)_2$—$(CH_2)_n$—$CF_3$, —$S(O)_2$—$(CH_2)_n$—$CHF_2$, —$S(O)_2$—$(CH_2)_n$—$CH_2F$, —$S(O)_2$-$T^0$, and —$S(O)_2$—$C_{1-3}$ alkylene-$T^0$;

$R^j$ is

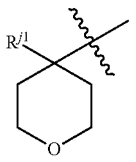
or
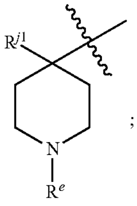
;

$R^{j1}$ is —CN, —COOH, —C(O)O—$C_{1-3}$ alkyl, —$(CH_2)_n$—OH, or —$(CH_2)_n$—O—$C_{1-3}$ alkyl;

$R^a$ and $R^b$ are each independently selected from the group consisting of hydrogen, —$C_{1-3}$ alkyl, —$C_{1-4}$ alkylene-OH, -$T^0$, —$C_{1-3}$ alkylene-$T^0$, —$(CH_2)_n$—$CF_3$, —$(CH_2)_n$—$CHF_2$, —$(CH_2)_n$—$CH_2F$, —C(O)—$C_{1-3}$ alkyl, —C(O)—$C_{2-4}$ alkenyl, —C(O)—$(CH_2)_n$—$CF_3$, —C(O)—$(CH_2)_n$—$CHF_2$, —C(O)—$(CH_2)_n$—$CH_2F$, —C(O)-$T^0$, —C(O)—$C_{1-3}$ alkylene-$T^0$, —$C_{2-4}$ alkylene-$OCH_3$ and —$C_{2-6}$ alkylene-$CH_3$, wherein the $C_{2-6}$ alkylene is optionally interrupted by an oxygen atom and/or is optionally substituted by one or more $C_{1-3}$ alkyl; or $R^a$ and $R^b$ together with the nitrogen atom to which they are attached form an unsubstituted or substituted 4-6 membered heterocycloalkyl, wherein the 4-6 membered heterocycloalkyl is a heterocycloalkane with one nitrogen as heteroatom, a heterocycloalkane with two nitrogens as heteroatoms, or a heterocycloalkane with one nitrogen and one oxygen as heteroatoms;

$T^0$ is —$C_{3-8}$ cycloalkyl, 4-6 membered heterocycloalkyl, phenyl or 5-6 membered heteroaryl unsubstituted or substituted by $T^1$; when the 4-6 membered heterocycloalkyl or 5-6 membered heteroaryl comprising a nitrogen as a heteroatom, the nitrogen atom is not substituted or substituted by $T^2$;

$T^1$ is selected from the group consisting of halogen, —$C_{1-6}$ alkyl, —$C_{1-3}$ alkoxyl, —$C_{1-6}$ alkyl substituted by —$C_{1-3}$ alkyl, and —$NR^cR^d$;

$T^2$ is selected from the group consisting of —$C_{1-4}$ alkyl, —$C_{2-4}$ alkyl substituted by —$C_{1-3}$ alkyl, —$C_{1-4}$ alkylene-OH, —$C_{3-6}$ cycloalkyl, 4-6 membered heterocycloalkyl, —$(CH_2)_n$—$CF_3$, —$(CH_2)_n$—$CHF_2$, —$(CH_2)_n$—$CH_2F$, —C(O)—$C_{1-3}$ alkyl, —C(O)—$C_{2-4}$ alkenyl, —C(O)—$(CH_2)_n$—$CF_3$, —C(O)—$(CH_2)_n$—$CHF_2$, —C(O)—$(CH_2)_n$—$CH_2F$, tert-butoxycarbonyl, —$S(O)_2$—$C_{1-3}$ alkyl, —$S(O)_2$—$(CH_2)_n$—$CF_3$, and —$S(O)_2$—$(CH_2)_n$—$CHF_2$;

n is 1, 2, 3, or 4;

$R^3$ is hydrogen, —$C_{1-4}$ alkyl or substituted —$C_{1-4}$ alkyl, wherein the substituted —$C_{1-4}$ alkyl is optionally substituted by one or more of the following substituents: hydroxyl, carboxy or —C(O)O—R';

R' is selected from the group consisting of —$C_{1-6}$ alkyl, —$C_{2-6}$ alkenyl, —$C_{2-6}$ alkynyl, —$C_{3-8}$ cycloalkyl and —$C_{4-10}$ heterocycloalkyl;

$R^4$ and $R^5$ are each independently —$C_{1-6}$ alkyl;

$R^{5a}$ is —$C_{1-6}$ alkyl or —$C_{1-6}$ alkoxyl;

$R^6$ is selected from the group consisting of —$C_{1-6}$ alkyl, 4-6 membered cycloalkyl, 4-6 membered heterocycloalkyl and a bicyclic ring having 8 to 10 carbon atoms; in the 4-6 membered heterocycloalkyl, the heteroatom is nitrogen, sulfur or oxygen; both rings in the bicyclic ring are connected by fusion, and any ring of the bicyclic ring is saturated, unsaturated or aromatic; the cycloalkyl, heterocycloalkyl or bicyclic ring with 8 to 10 carbon atoms is unsubstituted or substituted by one or more $R^{6a}$, wherein $R^{6a}$ is selected from the group consisting of halogen, hydroxyl, —$C_{1-3}$ alkyl, —$C_{1-3}$ alkoxyl, 3-6 membered cycloalkyl, 4-6 membered heterocyclic group, —$NR^hR^k$, —C(O)—$C_{1-3}$ alkyl, —C(O)—$C_{3-6}$ cycloalkyl, —$S(O)_2$—$C_{1-3}$ alkyl, —$(CH_2)_n$—$CF_3$, and —$S(O)_2$—$C_{3-6}$ cycloalkyl;

when $R^6$ is a 4-6 membered heterocycloalkyl containing one sulfur atom, the sulfur heteroatom is not oxidized or is oxidized by two oxy groups to form a sulfone group; or when $R^6$ is a 4-6 membered heterocycloalkyl containing one nitrogen atom, the nitrogen atom is unsubstituted or substituted by $R^{6b}$, wherein $R^{6b}$ is selected from the group consisting of —$C_{1-4}$ alkyl, —$C_{2-4}$ alkyl substituted by —$C_{1-3}$ alkyl, —$C_{1-4}$ alkylene-OH, —$C_{3-8}$ cycloalkyl, 4-6 membered heterocycloalkyl, —C(O)—$C_{1-3}$ alkyl, —C(O)—$C_{3-6}$ cycloalkyl, —$(CH_2)_n$—$CF_3$, —$S(O)_2$—$C_{1-3}$ alkyl, and —$S(O)_2$—$C_{3-6}$ cycloalkyl;

$R^h$ and $R^k$ are each independently selected from the group consisting of hydrogen, —$C_{1-3}$ alkyl, —$C_{1-4}$ alkylene-OH, -$T^0$, —$C_{1-3}$ alkylene-$T^0$, —$(CH_2)_n$—$CF_3$, —$(CH_2)_n$—$CHF_2$, —$(CH_2)_n$—$CH_2F$, —C(O)—$C_{1-3}$ alkyl, —C(O)—$C_{2-4}$ alkenyl, —C(O)—$(CH_2)_n$—$CF_3$, —C(O)—$(CH_2)_n$—$CHF_2$, —C(O)—$(CH_2)_n$—$CH_2F$, —C(O)-$T^0$, —C(O)—$C_{1-3}$ alkylene-$T^0$, —$C_{2-4}$ alkylene-$OCH_3$ and —$C_{2-6}$ alkylene-$CH_3$, wherein the $C_{2-6}$ alkylene is optionally interrupted by an oxygen atom and/or is optionally substituted by one or more $C_{1-3}$ alkyl;

or $R^h$ and $R^k$ together with the nitrogen atom to which they are attached form a 4-6 membered heterocycloalkyl which is unsubstituted or substituted with one or two T groups, wherein T is selected from the group consisting of halogen, —$C_{1-4}$ alkyl, —$C_{2-4}$ alkyl substituted by —$C_{1-3}$ alkyl and —$NR^cR^d$; and $R^c$ and $R^d$ are each independently selected from the group consisting of hydrogen, —$C_{1-3}$ alkyl, —$C_{1-4}$ alkylene-OH, —$C_{2-4}$ alkylene-$OCH_3$ and —$C_{2-6}$ alkylene-$CH_3$, wherein the $C_{2-6}$ alkylene is optionally interrupted by an oxygen atom and/or is optionally substituted by one or more $C_{1-3}$ alkyl.

2. The compound represented by general formula (I), or the tautomer, mesomer, racemate, enantiomer, diastereomer or mixture thereof, pharmaceutically acceptable salt, polymorph, solvate or isotopic derivative thereof according to claim 1, wherein $R^4$ and $R^5$ are each independently —$C_{1-3}$ alkyl;

$R^3$ is hydrogen or —$C_{1-4}$ alkyl;

$R^{5a}$ is —$C_{1-2}$ alkyl or —$C_{1-2}$ alkoxyl;

$R^6$ is selected from the group consisting of methyl, ethyl, propyl,

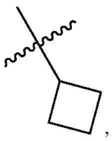,
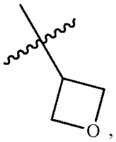,
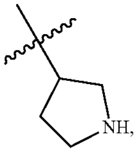,
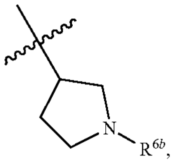,
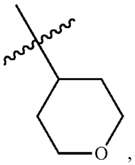,
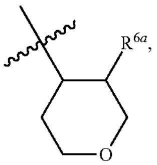,
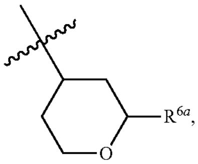,
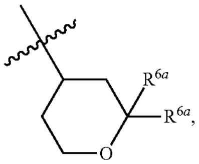,
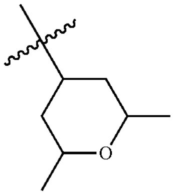,
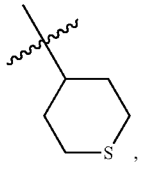,
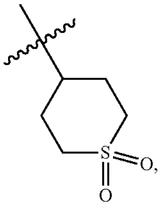,
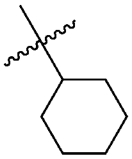,
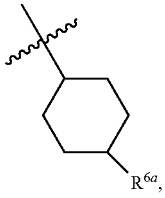,
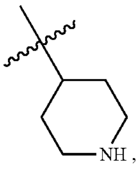,
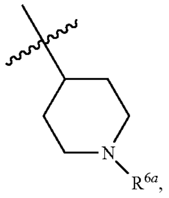,
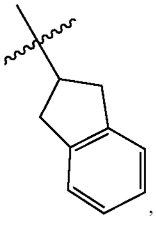,
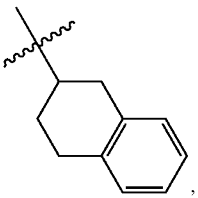,
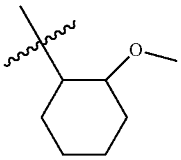
and -continued

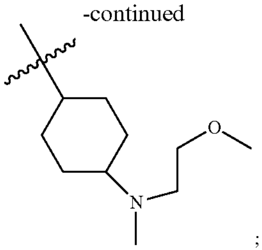
;

$R^{6b}$ is selected from the group consisting of —$C_{1-3}$ alkyl, —$C_{2-3}$ alkyl substituted by —$C_{1-2}$ alkyl, —$C_{3-6}$ cycloalkyl, 4-6 membered heterocycloalkyl, —C(O)—$C_{1-3}$ alkyl, —C(O)—$C_{3-6}$ cycloalkyl, —$(CH_2)_n$—$CF_3$, —$S(O)_2$—$C_{1-3}$ alkyl, and —$S(O)_2$—$C_{3-6}$ cycloalkyl, wherein the heteroatom in the 4-6 membered heterocycloalkyl group is nitrogen or oxygen;

$R^h$ and $R^k$ are each independently selected from the group consisting of hydrogen, —$C_{1-3}$ alkyl, —$C_{2-3}$ alkylene-$OCH_3$, and —$C_{2-6}$ alkylene-$CH_3$, wherein the $C_{2-6}$ alkylene is optionally interrupted by an oxygen atom and/or is optionally substituted by one or more $C_{1-3}$ alkyl.

3. The compound represented by general formula (I), or the tautomer, mesomer, racemate, enantiomer, diastereomer or mixture thereof, pharmaceutically acceptable salt, polymorph, solvate or isotopic derivative thereof according to claim 1, wherein $T^0$ is —$C_{3-6}$ cycloalkyl or 4-6 membered heterocycloalkyl, wherein the 4-6 membered heterocycloalkyl contains 1 or 2 heteroatoms each independently chosen from nitrogen and oxygen;

$T^1$ is selected from the group consisting of fluorine, methyl, ethyl, propyl, —$C_{1-3}$ alkoxyl, —$C_{2-3}$ alkyl substituted by —$C_{1-2}$ alkyl, and —$NR^cR^d$;

$R^e$ is selected from the group consisting of methyl, ethyl, propyl, —$C_{2-4}$ alkyl substituted by —$C_{1-2}$ alkyl, —$C_{2-4}$ alkyl substituted by hydroxyl, —$CH(CH_3)$—$CH_3$, —$CH(CH_3)$—$(CH_2)$—$CH_3$, —$CH(CH_3)$—$CH(CH_3)_2$, —$CH_2$—$C(CH_3)_3$, -$T^0$, —$C_{1-3}$alkylene-$T^0$, —$(CH_2)_n$—$CF_3$, —$(CH_2)_n$—$CF_2$—$CF_3$, —$(CH_2)_n$—O—$C_{1-3}$ alkyl, —$CH_2$—O—$C_{1-3}$ alkyl, —C(O)—$C_{1-3}$ alkyl, —$(CH_2)_n$—C(O)—$C_{1-3}$ alkyl, —C(O)—$C_{2-4}$ alkenyl, —C(O)—$CF_3$, —C(O)—$(CH_2)_n$—$CF_3$, —C(O)-$T^0$, tert-butoxycarbonyl, —C(O)—O—$C_{1-3}$ alkyl, —C(O)—O-$T^0$, —$S(O)_2$—$C_{1-3}$ alkyl and —$S(O)_2$-$T^0$;

$R^f$ and $R^g$ are each independently selected from the group consisting of fluorine, —OH, —$CF_3$, methyl, ethyl, propyl, —$C_{2-3}$ alkyl substituted by —$C_{1-2}$ alkyl, —$(CH_2)_n$—$CF_3$, -$T^0$, —$C_{1-3}$ alkylene-$T^0$, —$NR^aR^b$, —$C_{1-3}$ alkylene-$NR^aR^b$, —O—$C_{1-4}$ alkyl, —O—$C_{2-4}$ alkenyl, —O-$T^0$, —NH—C(O)—$C_{2-4}$ alkenyl, —C(O)—$C_{1-3}$ alkyl, —C(O)—$C_{2-4}$ alkenyl, —C(O)—$(CH_2)_n$—$CF_3$, —C(O)-$T^0$, tert-butoxycarbonyl, —C(O)—O—$C_{1-3}$ alkyl, and —C(O)—O-$T^0$;

$R^a$ and $R^b$ are each independently selected from the group consisting of methyl, ethyl, propyl, —$C_{1-4}$ alkylene-OH, —$C_{2-4}$ alkylene-$OCH_3$ and

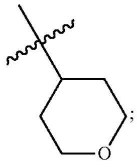 [SMILES: *C1CCOCC1]
;

or $R^a$ and $R^b$ together with the nitrogen atom to which they are attached form an unsubstituted or substituted 4-6 membered heterocycloalkyl, wherein the 4-6 membered heterocycloalkyl is a heterocycloalkane with one nitrogen as heteroatom, a heterocycloalkane with two nitrogens as heteroatoms, or a heterocycloalkane with one nitrogen and one oxygen as heteroatoms.

4. The compound represented by general formula (I), or the tautomer, mesomer, racemate, enantiomer, diastereomer or mixture thereof, pharmaceutically acceptable salt, polymorph, solvate or isotopic derivative thereof according to claim 1, wherein $R^6$ is selected from the group consisting of methyl, ethyl, propyl,

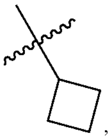, 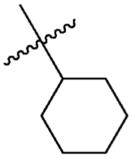, 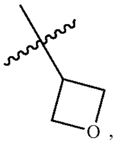,

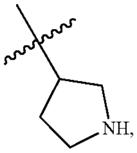 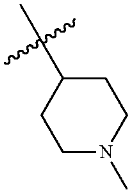, 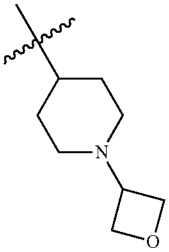,

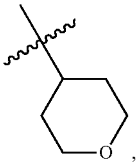, 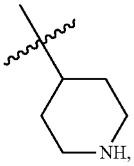

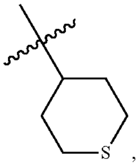, 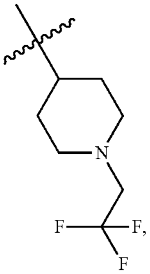

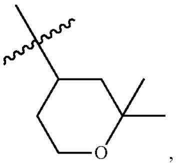, 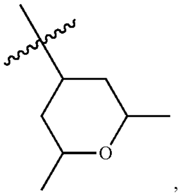,

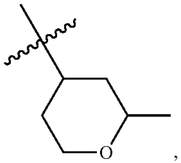, 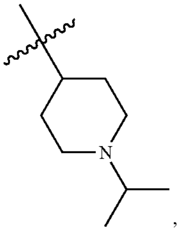,

-continued

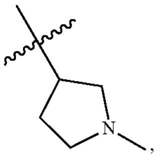, 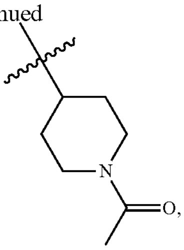

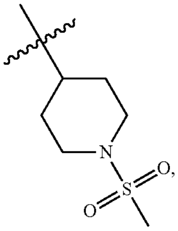 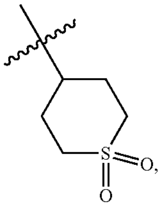

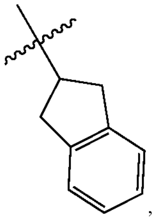, 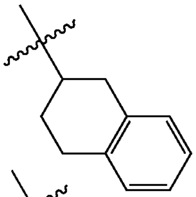,

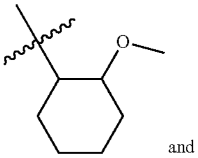 and 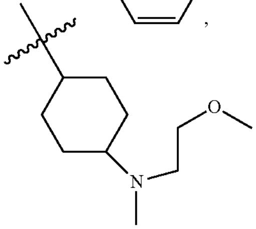;

$R^e$ is selected from the group consisting of methyl, ethyl, propyl, $-CH(CH_3)-CH_3$, $-CH(CH_3)-(CH_2)CH_3$, $-CH(CH_3)-CH(CH_3)_2$, $-CH_2-C(CH_3)_3$, $T^0$, $-(CH_2)_n$-$T^0$, $-(CH_2)_n-CF_3$, $-CH_2-CH(OH)-CH_3$, $-(CH_2)_n-CF_2-CF_3$, $-(CH_2)_2-O-C_{1-3}$ alkyl, $-C(O)-C_{1-3}$ alkyl, $-(CH_2)_n-C(O)-C_{1-3}$ alkyl, $-C(O)-C_{2-4}$ alkenyl, $-C(O)-CF_3$, $-C(O)-(CH_2)_n-CF_3$, $-C(O)$-morpholinyl, $-C(O)C_{3-6}$ cycloalkyl, tert-butoxycarbonyl, $-C(O)-O-C_{1-3}$ alkyl and $-S(O)_2-C_{1-3}$ alkyl;

$R^f$ is selected from the group consisting of methyl, ethyl, propyl, $-F$, $-Cl$, $-OH$, $T^0$, and $-C_{1-3}$ alkylene-$T^0$;

$R^g$ is selected from the group consisting of $T^0$, $-C_{1-3}$ alkylene-$T^0$, $-NH-C(O)-C_{2-3}$ alkenyl, $-NR^aR^b$ and $-F$;

$R^a$ and $R^b$ are each independently selected from the group consisting of methyl, ethyl, propyl and

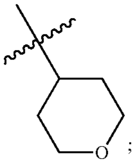 [SMILES: *C1CCOCC1];

and $T^0$ is selected from the group consisting of

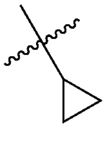, 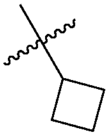, 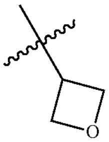, 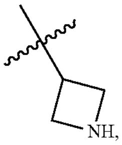

-continued
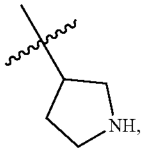
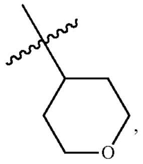
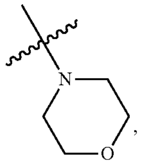
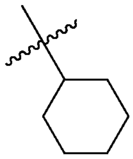
and
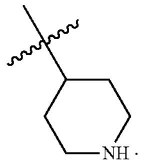
5. A compound, or a tautomer, a mesomer, a racemate, an enantiomer, a diastereomer or a mixture thereof, a pharmaceutically acceptable salt, a polymorph, a solvate or an isotopic derivative thereof wherein the compound is selected from the group consisting of:
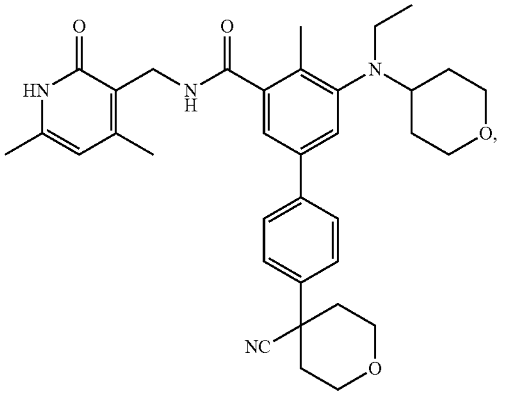
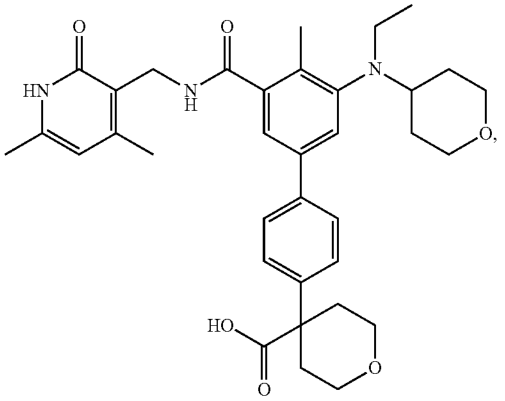
-continued
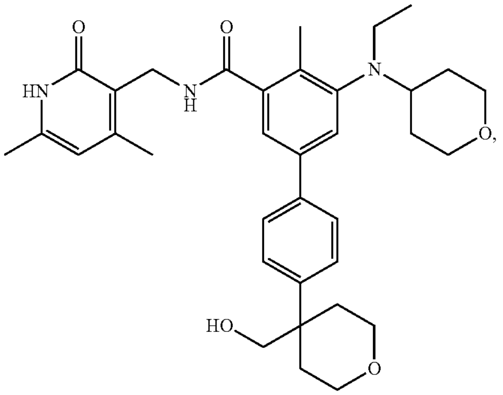
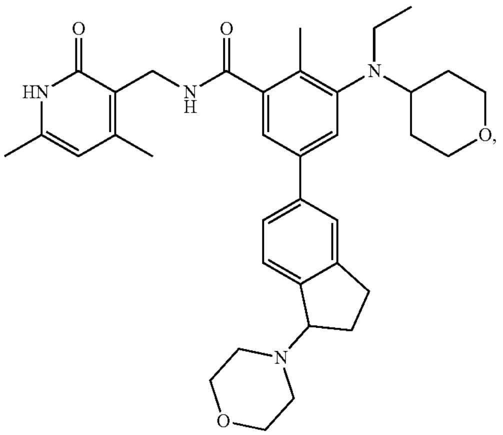
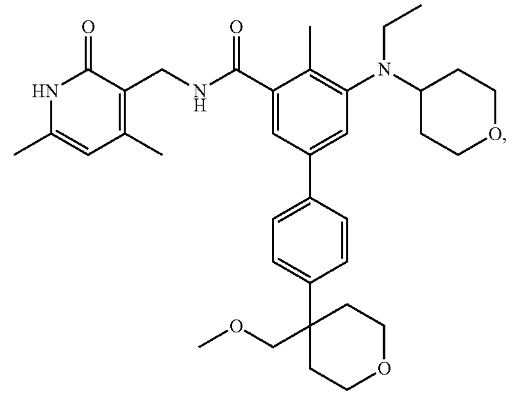
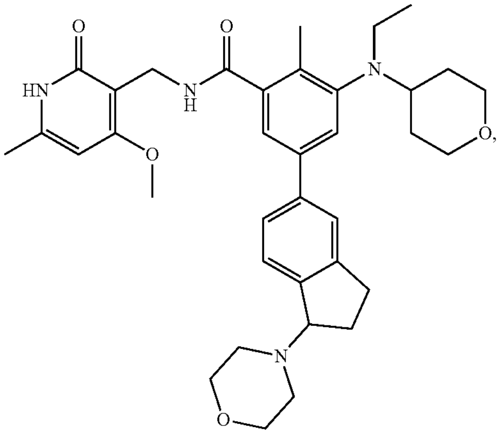

-continued
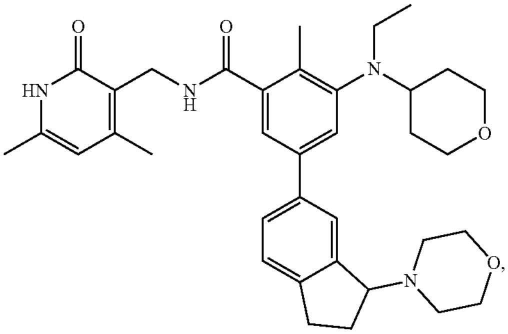
,
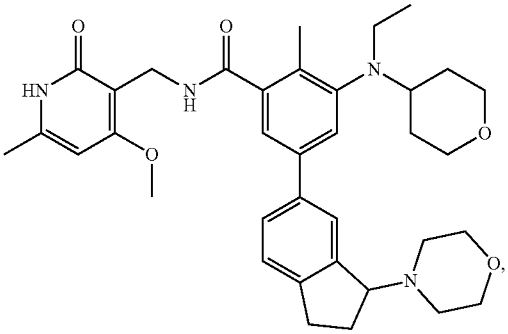
,
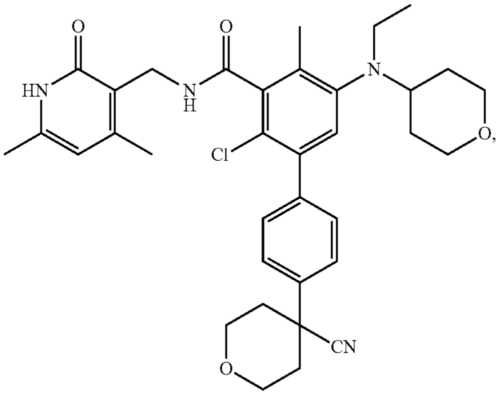
,
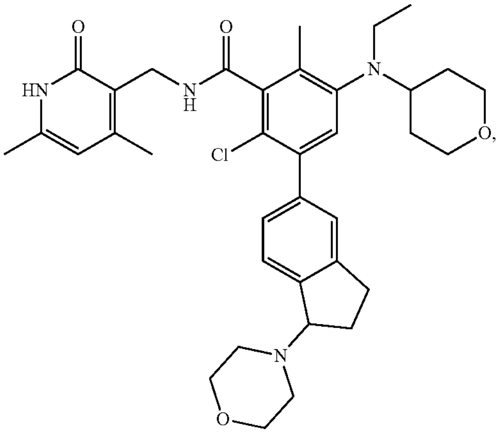
,
-continued
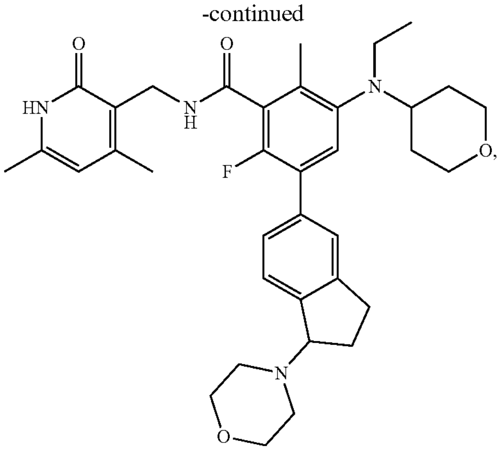
,
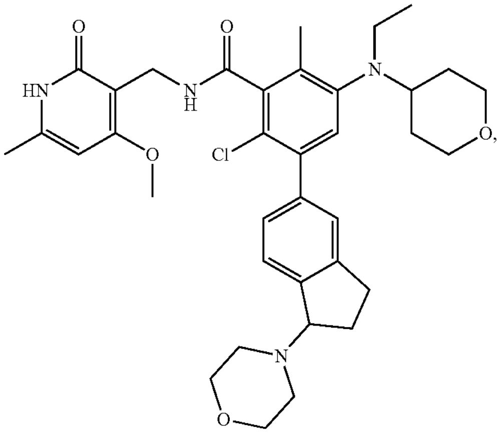
,
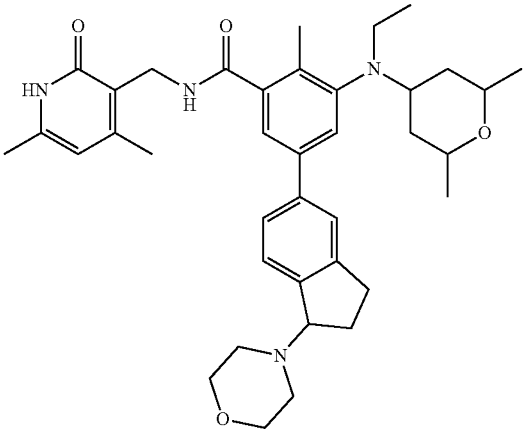
,
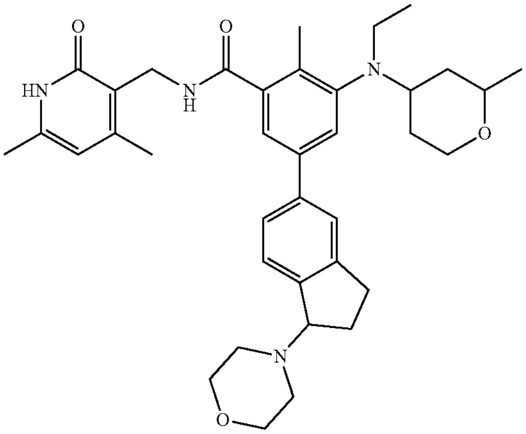
, -continued
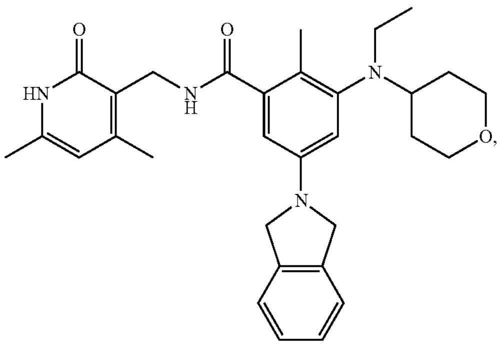
,
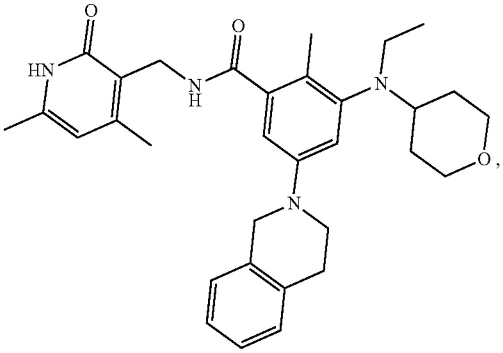
,
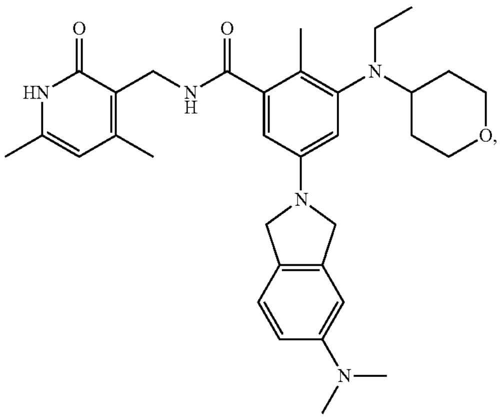
,
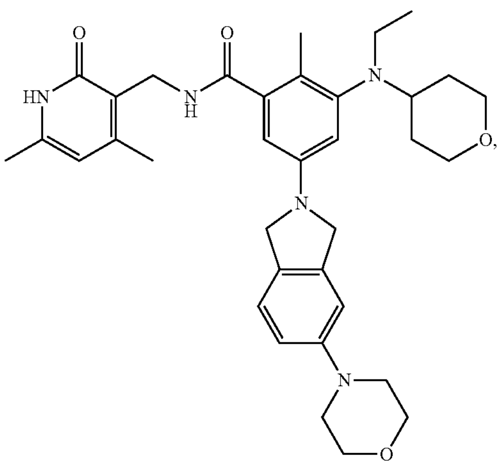
,
-continued
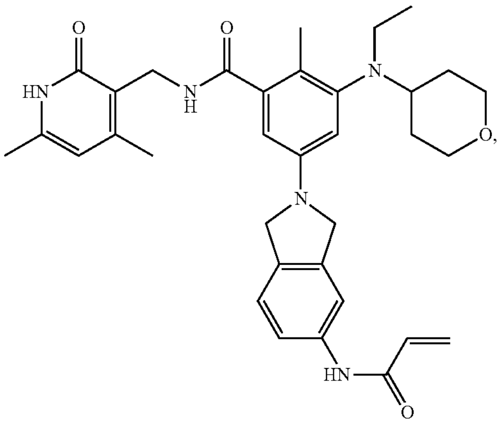
,
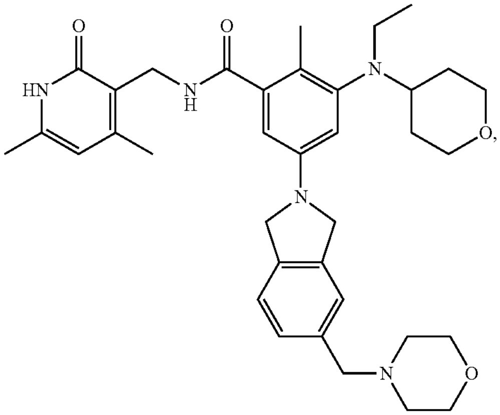
,
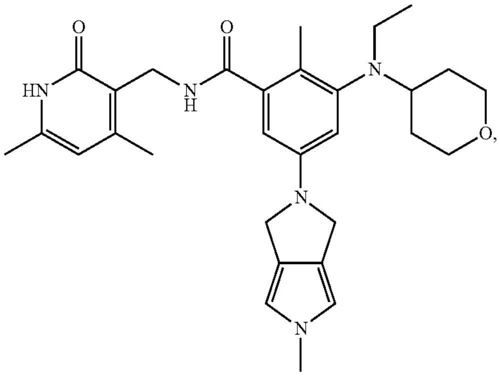
,
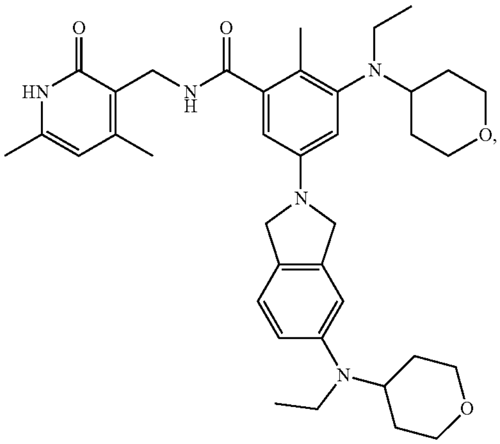
, and -continued
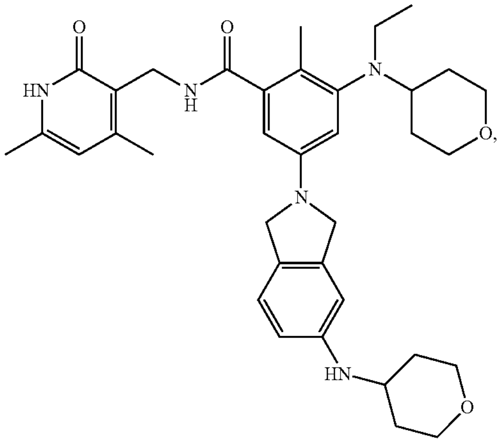
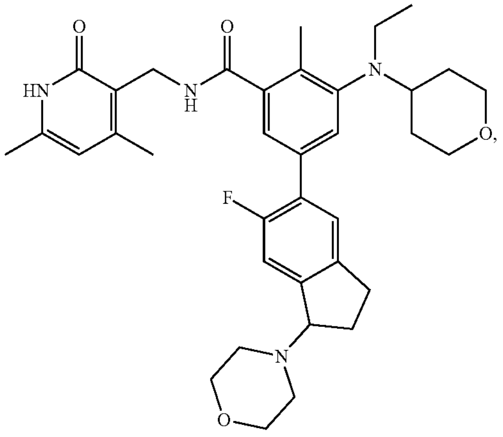
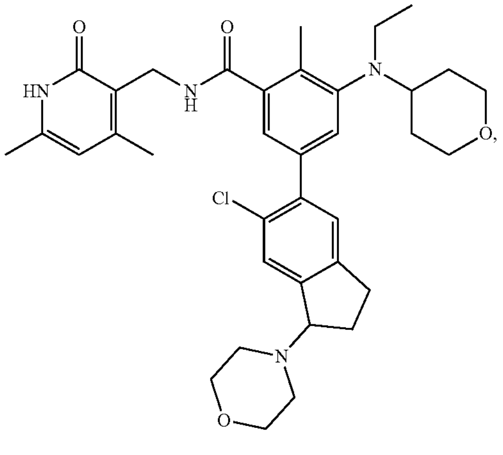
-continued
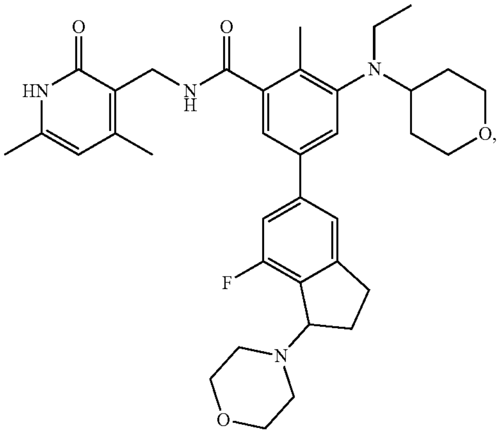
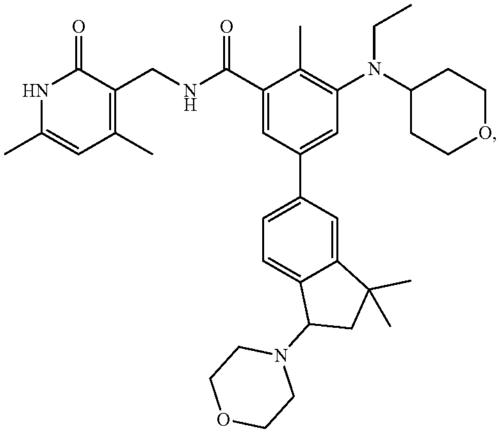
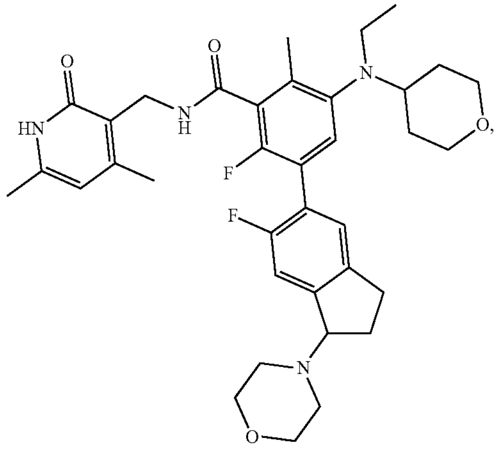

-continued

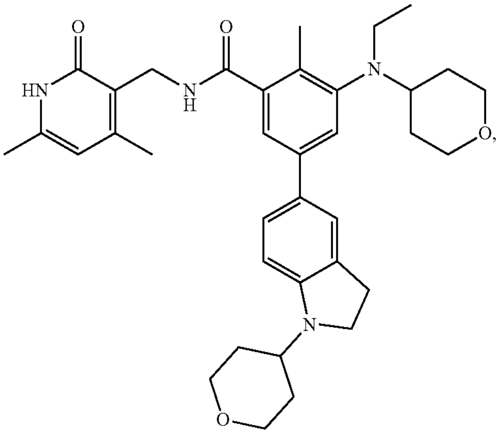

and

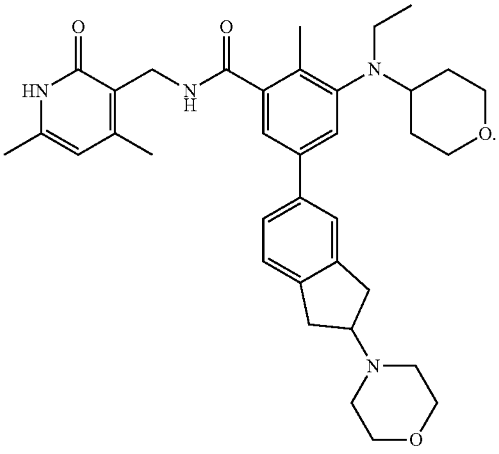

6. A method for preparing the compound represented by general formula (I) according to claim 1, wherein the compound represented by general formula (I) is prepared by the following scheme, scheme 1

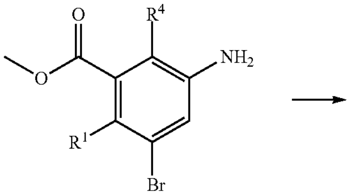

I-1

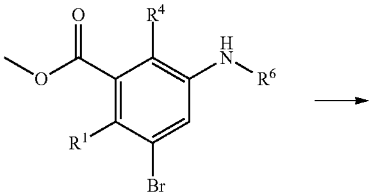

I-2

-continued

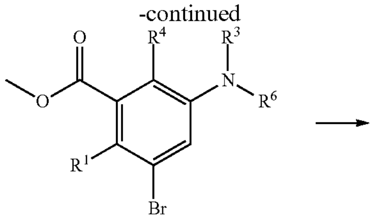

I-3

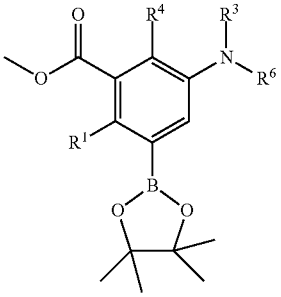

I-4

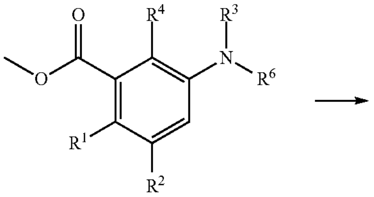

I-5

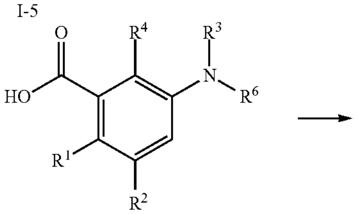

I-6

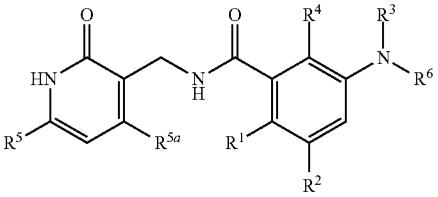

I-7 the compound of general formula I-1 and a ketone compound K1 undergoing a reductive amination reaction to obtain the compound of general formula I-2, wherein K1 is selected from the group consisting of —C(O)—$C_{1-6}$ alkyl, oxo substituted 4-6 membered cycloalkyl, oxo substituted 4-6 membered heterocycloalkyl and oxo substituted bicyclic ring having 8 to 10 carbon atoms; in the 4-6 membered heterocycloalkyl, the heteroatom is nitrogen, sulfur or oxygen; both rings in the bicyclic ring is connected by fusion, and any one ring in the bicyclic ring is saturated, unsaturated or aromatic; the oxo substituted cycloalkyl, oxo substituted heterocycloalkyl or oxo substituted bicyclic ring with 8 to 10 carbon atoms is unsubstituted or substituted by one or more $R^{6a}$, wherein $R^{6a}$ is selected from the group consisting of halogen, hydroxyl, —$C_{1-3}$ alkyl, —$C_{1-3}$ alkoxyl, 3-6 membered cycloalkyl, 4-6 membered heterocyclic group, —$NR^hR^k$, —C(O)—$C_{1-3}$ alkyl, —C(O)—$C_{3-6}$ cycloalkyl, —$S(O)_2$—$C_{1-3}$ alkyl, —$(CH_2)_n$—$CF_3$, and —$S(O)_2$—$C_{3-6}$ cycloalkyl;

the compound of general formula I-2 undergoing a reductive amination reaction with an aldehyde compound $R^7$—CHO at the presence of a reducing agent to obtain the compound of general formula I-3, wherein $R^7$ is hydrogen, —$C_{1-4}$ alkyl or substituted —$C_{1-4}$ alkyl, wherein the substituted —$C_{1-4}$ alkyl is optionally substituted by one or more of the following substituents: hydroxyl, carboxy or —C(O)O—R'; the reducing agent is optionally sodium triacetoxyborohydride;

the compound of general formula I-3 reacting with a pinacol diborate compound under heating and alkaline condition, and the presence of a catalyst to obtain the compound of the general formula I-4, wherein a reagent that provides alkaline condition is optionally potassium acetate, and the catalyst is optionally [1,1'-bis(diphenylphosphino)ferrocene]palladium dichloride;

the compound of general formula I-4 reacting with a corresponding halogenated aryl group $R^2$—Z under heating and alkaline condition, and the presence of a catalyst to obtain the compound of general formula I-5, wherein a reagent that provides alkaline condition is optionally selected from the group consisting of potassium carbonate, cesium carbonate, potassium hydroxide, sodium hydroxide, and cesium fluoride; the catalyst is optionally selected from the group consisting of [1,1'-bis(diphenylphosphino)ferrocene]palladium dichloride, palladium acetate, tetrakistriphenylphosphine palladium, and tris(dibenzylideneacetone)dipalladium, wherein Z is halogen;

hydrolyzing the compound of general formula I-5 under alkaline condition to obtain a compound of general formula I-6, wherein a reagent that provides alkaline condition is optionally sodium hydroxide;

the compound of general formula I-6 undergoing a condensation reaction with a corresponding amine

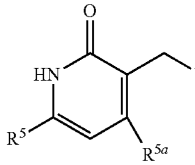

to obtain the compound of general formula (I); or scheme 2

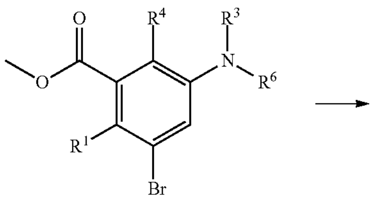

I-3

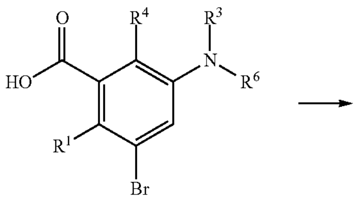

II-1

-continued

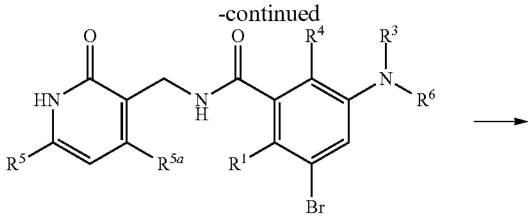

II-2

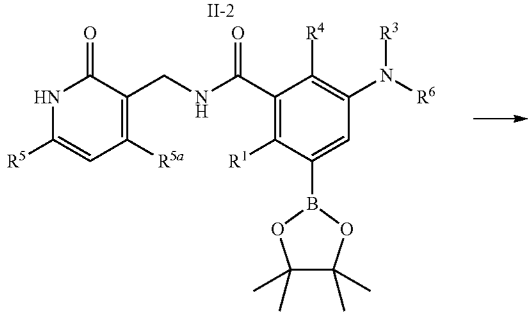

II-3

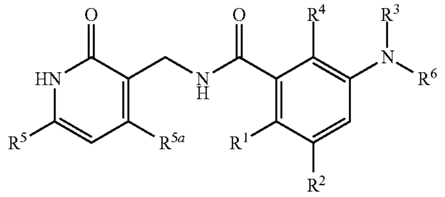

I the compound of general formula I-3 undergoing a hydrolysis reaction under heating and alkaline conditions to obtain a compound of general formula II-1, wherein a reagent that provides alkaline condition is optionally selected from the group consisting of sodium hydroxide, potassium hydroxide, potassium carbonate, sodium carbonate, and cesium carbonate; the compound of general formula II-2 is obtained by the condensation reaction of the compound of general formula II-1 with a corresponding amine

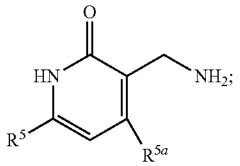

the compound of the general formula II-2 reacting with a pinacol diborate compound under heating and alkaline conditions, and the presence of a catalyst to obtain the compound of general formula II-3, wherein a reagent that provides alkaline condition is optionally potassium acetate, and the catalyst is optionally [1,1'-bis(diphenylphosphino)ferrocene]palladium dichloride;

the compound of general formula II-3 reacting with a corresponding halogenated aryl group $R^2$—Z under heating and alkaline conditions, and the presence of a catalyst to obtain the compound of general formula (I), wherein a reagent that provides alkaline condition is optionally selected from the group consisting of potassium carbonate, cesium carbonate, potassium hydroxide, sodium hydroxide, and cesium fluoride; the catalyst is optionally selected from the group consisting of

[1,1'-bis(diphenylphosphino)ferrocene]palladium dichloride, palladium acetate, tetrakistriphenylphosphine palladium, and tris(dibenzylideneacetone)dipalladium, wherein Z is halogen; or scheme 3

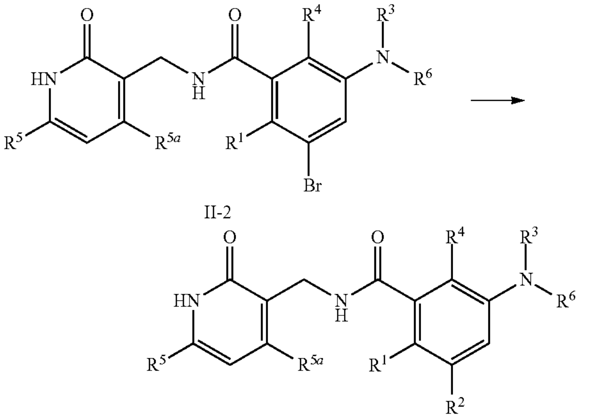

II-2

I the compound of general formula II-2 reacting with a corresponding aryl boronic ester

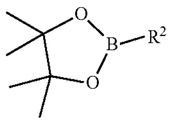

under conditions of heating, alkalinity, and the presence of a catalyst to obtain the compound of general formula (I); wherein a reagent that provides alkaline condition is optionally selected from the group consisting of potassium carbonate, cesium carbonate, potassium hydroxide, sodium hydroxide, and cesium fluoride; the catalyst is optionally selected from the group consisting of [1,1'-bis(diphenylphosphino)ferrocene]palladium dichloride, palladium acetate, tetrakistriphenylphosphine palladium, and tris(dibenzylideneacetone)dipalladium.

7. The method according to claim 6, wherein K1 is selected from the group consisting of

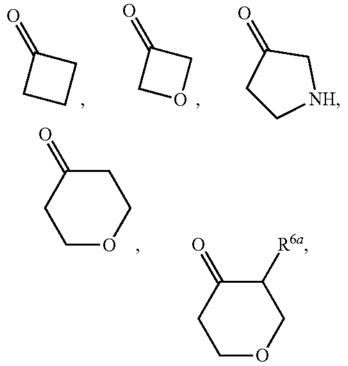

-continued

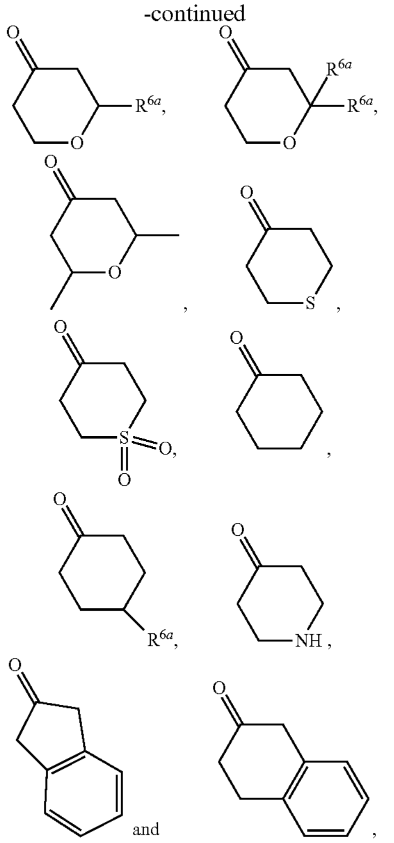

and $R^7$ is hydrogen or —$C_{1-3}$ alkyl.

8. A pharmaceutical composition comprising a therapeutically effective amount of the compound represented by general formula (I) or the tautomer, mesomer, racemate, enantiomer, diastereomer or mixture thereof, pharmaceutically acceptable salt, polymorph, solvate or isotopic derivative thereof according to claim 1 and optionally one or more pharmaceutically acceptable carriers and/or diluents.

9. A method for preventing and/or treating EZH2-mediated diseases, wherein the EZH2-mediated diseases are selected from the group consisting of tumors, myeloproliferative diseases and autoimmune diseases, and wherein the method comprises administering the compound represented by general formula (I), or the tautomer, mesomer, racemate, enantiomer, diastereomer or mixture thereof, pharmaceutically acceptable salt, polymorph, solvate or isotopic derivative thereof according to claim 1.

10. The method according to claim 9, wherein the tumor is prostate cancer, breast cancer, bladder cancer, lung cancer, rectal cancer, lymphoma or leukemia, and the autoimmune disease is inflammatory enteritis, autoimmune encephalomyelitis or multiple sclerosis.

11. A method for preventing and/or treating tumors, myeloproliferative diseases, inflammatory bowel disease, autoimmune encephalomyelitis or multiple sclerosis, wherein the method comprises administering a therapeutically effective amount of the compound represented by general formula (I), or the tautomer, mesomer, racemate, enantiomer, diastereomer or mixture thereof, pharmaceutically acceptable salt, polymorph, solvate or isotopic derivative thereof according to claim 1 to a subject in need.

* * * * *